United States Patent
Stellwagen et al.

(10) Patent No.: US 10,328,092 B2
(45) Date of Patent: Jun. 25, 2019

(54) METHODS AND COMPOSITIONS FOR TREATMENT OF DRUG ADDICTION

(71) Applicant: The Royal Institution for the Advancement of Learning / McGill University, Montreal (CA)

(72) Inventors: David Stellwagen, Montreal (CA); Gil Moshe Lewitus, Ness-Ziona (IL)

(73) Assignee: THE ROYAL INSTITUTION FOR THE ADVANCEMENT OF LEARNING / MCGILL UNIVERSITY, Montreal (CA)

( * ) Notice: Subject to any disclaimer, the term of this patent is extended or adjusted under 35 U.S.C. 154(b) by 0 days.

(21) Appl. No.: 15/178,138

(22) Filed: Jun. 9, 2016

(65) Prior Publication Data

US 2017/0027972 A1    Feb. 2, 2017

Related U.S. Application Data

(60) Provisional application No. 62/173,015, filed on Jun. 9, 2015.

(51) Int. Cl.
| | | |
|---|---|---|
| *A61K 31/7028* | (2006.01) | |
| *A61P 25/30* | (2006.01) | |
| *A61P 25/32* | (2006.01) | |
| *A61P 25/34* | (2006.01) | |
| *A61P 25/36* | (2006.01) | |

(52) U.S. Cl.
CPC .......... *A61K 31/7028* (2013.01); *A61P 25/30* (2018.01); *A61P 25/32* (2018.01); *A61P 25/34* (2018.01); *A61P 25/36* (2018.01)

(58) Field of Classification Search
CPC ...... A61K 31/7028; A61P 25/30; A61P 25/32; A61P 25/34; A61P 25/63
See application file for complete search history.

(56) References Cited

PUBLICATIONS

Carrera et al., PNAS, 2000, 97(11), p. 6202-6206. (Year: 2000).*
Baldridge et al., Methods, 1999, 19, p. 103-107. (Year: 1999).*
Aybay et al., FEMS Immunol. Med. Microbio., 1998, 22, p. 263-273. (Year: 1998).*
Theberge et al., Biol. Psychiatry, 2013, 73, p. 729-737. (Year: 2013).*
Northcutt et al., Mol. Psychiatry, 2015, 20, p. 1525-1537, published online Feb. 3, 2015. (Year: 2015).*
Lewitus GM, Pribiag H, Duseja R, St-Hilaire M, Stellwagen D. An adaptive role of TNFα in the regulation of striatal synapses. J Neurosci. Apr. 30, 2014;34(18):6146-55.
Lewitus GM, Konefal SC, Greenhalgh AD, Pribiag H, Augereau K, Stellwagen D. Microglial TNF-α Suppresses Cocaine-Induced Plasticity and Behavioral Sensitization. Neuron. May 4, 2016;90(3):483-91.
Stellwagen D, Malenka RC. Synaptic scaling mediated by glial TNF-alpha. Nature. Apr. 20, 2006;440(7087)1054-9.

* cited by examiner

*Primary Examiner* — Jonathan S Lau
(74) *Attorney, Agent, or Firm* — Bereskin & Parr LLP; Carmela De Luca; Amy Dam

(57) ABSTRACT

Methods of reducing AMPA/NMDA ratio in D1-type medium spiny neurons (MSN) and/or reducing development of behavioral sensitization or suppressing drug induced behavioral sensitization in a subject, optionally a subject that is afflicted with an addiction, the method comprising administering to the subject in need thereof an effective amount of a Toll-like receptor 4 (TLR4) agonist or a composition comprising said TLR4 agonist, preferably wherein the TLR4 agonist is a monophosphoryl lipid A (MPLA).

21 Claims, 36 Drawing Sheets
Specification includes a Sequence Listing.

F

G

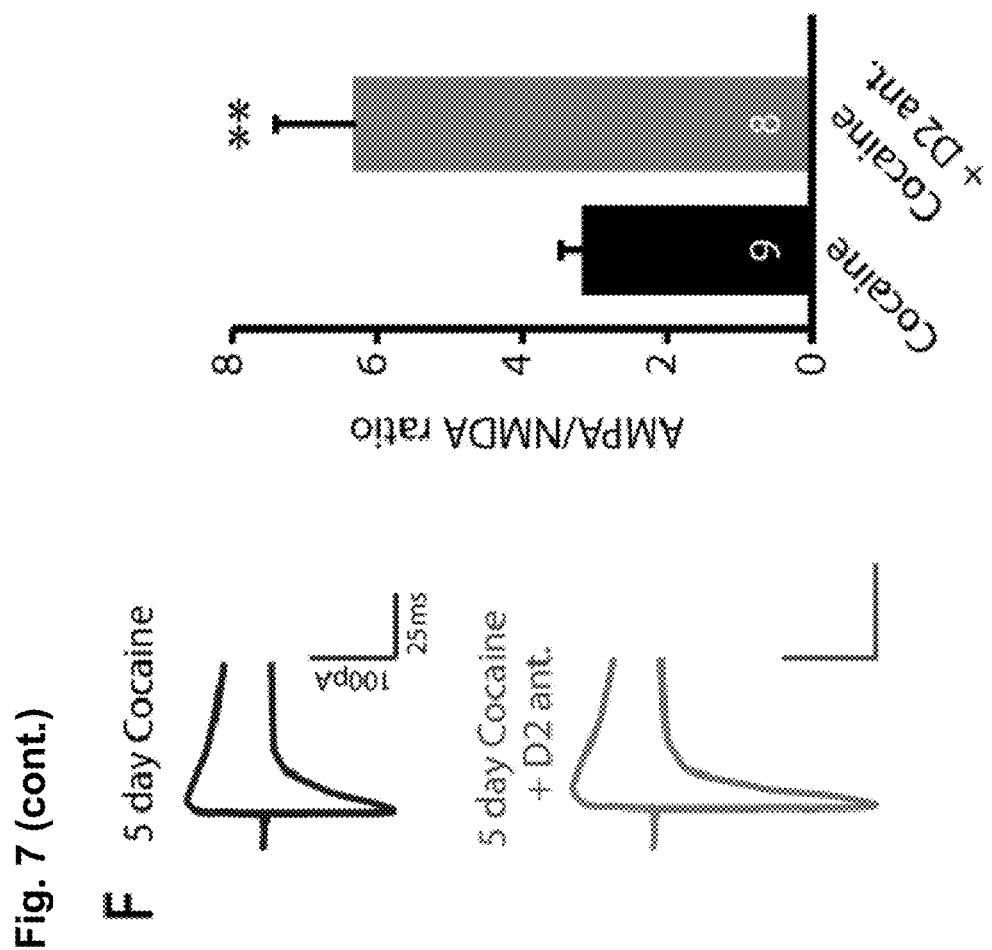

F

```
                        SEQUENCE LISTING

<160> NUMBER OF SEQ ID NOS: 7

<210> SEQ ID NO 1
<211> LENGTH: 20
<212> TYPE: DNA
<213> ORGANISM: Mus musculus x Rattus norvegicus

<400> SEQUENCE: 1
ccagtgtggg aagctgtctt                                              20

<210> SEQ ID NO 2
<211> LENGTH: 20
<212> TYPE: DNA
<213> ORGANISM: Mus musculus

<400> SEQUENCE: 2
aagcaaaaga ggaggcaaca                                              20

<210> SEQ ID NO 3
<211> LENGTH: 21
<212> TYPE: DNA
<213> ORGANISM: Mus musculus

<400> SEQUENCE: 3
atgtgtccgt cgtggatctg a                                            21

<210> SEQ ID NO 4
<211> LENGTH: 22
<212> TYPE: DNA
<213> ORGANISM: Rattus norvegicus

<400> SEQUENCE: 4
ttgaagtcgc aggagacaac ct                                           22

<210> SEQ ID NO 5
<211> LENGTH: 20
<212> TYPE: DNA
<213> ORGANISM: Rattus norvegicus

<400> SEQUENCE: 5
tgggagttgc tgttgaagtc                                              20

<210> SEQ ID NO 6
```

```
<211> LENGTH: 18
<212> TYPE: DNA
<213> ORGANISM: Rattus norvegicus

<400> SEQUENCE: 6
ccgctgtctc ttttcgcc                                                   18

<210> SEQ ID NO 7
<211> LENGTH: 22
<212> TYPE: DNA
<213> ORGANISM: Rattus norvegicus

<400> SEQUENCE: 7
gctgtctttg gaactttgtc tg                                              22
```

METHODS AND COMPOSITIONS FOR TREATMENT OF DRUG ADDICTION

FIELD

The disclosure relates to methods and compositions for reducing AMPA/NMDA ratio in D1-type medium spiny neurons (MSN) and/or reducing likelihood of developing or redeveloping and/or treating drug addiction, and particularly to TLR4 agonists such as MPLA for reducing AMPA/NMDA ratio in D1-type MSNs and/or reducing likelihood of developing or redeveloping and/or treating drug addictions such as cocaine addiction.

BACKGROUND

Substance abuse accounts for a high number of preventable illnesses and deaths each year and places a significant social and financial toll on individuals and society. Presently, for example, there are no FDA-approved medications to treat cocaine addiction. Drugs of abuse produce their reinforcing effect through actions in the limbic component of the basal ganglia. With repeated use, drugs of abuse can cause long term changes in the brain's reward circuit. Specifically repeated exposure leads to profound changes in glutamate transmission in limbic nuclei, particularly the nucleus accumbens.

TNFα has been associated with the rewarding effects of methamphetamine. Exposure to methamphetamines results in glial activation and increases in TNFα level[9-11]. Cocaine administration results in upregulation of inflammatory signals, including TNFα[12]. Morphine and ethanol activate glia directly via the Toll-Like Receptor 4 (TLR4) and increase inflammatory signals including TNFα[13,14]. There are conflicting data on the role of TNFα in addiction-related behaviors. Narita et al. suggest that TNFα contributes to the rewarding effect of these drugs[15], while the Nabeshima group suggests that TNFα administration suppresses the rewarding effects of either drug[9,16,17].

Monophosphoryl lipid A (MPLA) is a Toll-like receptor 4 agonist commonly used as a nontoxic, FDA-approved adjuvant in vaccines. Also liposomes containing MPLA have been reported as a potent adjuvant system for inducing antibodies to heroin hapten analogs[22].

SUMMARY

An aspect includes a method of reducing AMPA/NMDA ratio in D1-type medium spiny neurons (MSN) and/or reducing development of behavioural sensitization or suppressing drug induced behavioural sensitization in a subject, optionally a subject that is afflicted with an addiction, comprising administering to the subject in need thereof an effective amount of a Toll-like receptor 4 (TLR4) agonist or a composition comprising said TLR4 agonist, optionally wherein the method is for reducing the likelihood of a subject developing or redeveloping a drug addiction and/or treating a subject afflicted with a drug addiction.

In an embodiment, the TLR4 agonist is monophosphoryl lipid A (MPLA), a derivative thereof and/or a mixture thereof.

In an embodiment, the drug is cocaine.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 5A is a diagram of the time points used for experiments: 24 hours after a single injection of saline or cocaine (i.p. 15 mg/kg), 24 hours after 5 daily injections of saline or cocaine, and 10 d after 5 daily injections of saline or cocaine. FIG. 5B is a representative confocal projection images of NAc immunostained for Iba1 (top) and TNFα (bottom) injected for 5 days with saline or cocaine (scale bar=20 μm). FIG. 5C is a graph showing that 5 daily injections of cocaine increases TNFα protein in the NAc (n=6 mice for 1 day saline, 6 for 1 day cocaine, 5 for 5 days saline, 6 for 5 days cocaine, 4 for withdrawal saline, 4 for withdrawal cocaine; Student's t-test, p<0.05). FIG. 5D is a graph showing that 5 daily injections of cocaine increases TNFα mRNA in the ventral striatum (n=5 (1 day), 4 (5 days), 5 (withdrawal) mice; Steel multiple comparison test, z=−2.774, p=0.0163 (5 days)). FIG. 5E shows a representative recording of EPSCs at −70 mV and +40 mV and mean AMPA/NMDA ratios from control slices and slices treated with 10 or 100 ng/ml TNFα in D1 and D2 MSNs in the NAc core. AMPA/NMDA ratios were calculated using the peak amplitude at −70 mV for AMPA and the amplitude at +40 mV taken 40 msec after the peak at −70 mV. One-way ANOVA: $F_{(5,74)}$=2.84, p<0.021. (D1: 3.75±0.43; n=22 cells (from 11 mice); $D1_{(10\ ug\ TNF)}$: 3.1±0.52; n=9 (3); $D1_{(100\ ug\ TNF)}$: 2.42±0.23; n=13 (7); D2: 2.69±0.288; n=17 (9); $D2_{(10\ ug\ TNF)}$: 2.78±0.34; n=8 (3); $D2_{(100\ ug\ TNF)}$: 2.02±0.18; n=11 (5)). FIG. 5F shows representative traces and mean AMPA/NMDA ratios in the NAc core, after 1 day and 5 days of cocaine (15 mg/kg) in WT or TNFα-KO mice. 5 days cocaine significantly decreased AMPA/NMDA ratios in D1 cells in WT mice but significantly increased ratios in TNFα−/− mice compared to saline injected control mice (ratios from mice injected with one or five daily doses of saline were not significantly different, and were combined). (One way ANOVA: $F_{(5,66)}$=2.83, p=0.022; WT: $D1_{(saline)}$: 4.18±0.55; n=12 cells (from 7 mice); $D1_{(1\ day\ cocaine)}$: 3.38±0.57; n=10 (4); $D1_{(5\ days\ cocaine)}$: 2.73±0.35; n=10 (3); TNFα−/−: D1: 3.03±0.34; n=17 (8); $D1_{(1\ day\ cocaine)}$: 4.28±0.35; n=15 (6); $D1_{(5\ days\ cocaine)}$: 4.97±083; n=8 (3)). FIG. 5G shows representative traces and mean AMPA/NMDA ratios from D1-MSNs in the NAc core from control slices or slices treated ex-vivo with TNFα. Treatment with a low dose of TNFα (10 ng/ml) significantly reduced AMPA/NMDA ratios on D1-MSNs from TNFα−/− mice treated 24 hours prior with cocaine (Student's t-test, $t_{(24)}$=2.16, p=0.042; control: 4.28±0.35; n=15 cells (from 6 mice); TNFα: 3.08±0.42; n=11 (4)). However, 100 ng/ml TNFα did not further decrease AMPA/NMDA ratios on D1-MSN from wildtype mice when the animals were previously exposed to 5 daily cocaine injections (Student's t-test, $t_{(16)}$=2.12, p=0.127; control: 3.17±0.30; n=9; TNFα: 4.06±0.46; n=9). FIG. 5H shows mean locomotor activity in response to cocaine injections in TNFα$^{-/-}$ and WT mice. Locomotor activity was monitored for 15 min immediately following each injection. TNFα$^{-/-}$ mice showed higher sensitization than WT mice during cocaine administration. (n=12 WT, 17 TNFα$^{-/-}$ animals). Two way-repeated-measures ANOVA; (treatment, $F_{(1,23)}$=0.38, p=0.0068; days, $F_{(4,20)}$=6.01, p<0.0001; treatment×days, $F_{(4,20)}$=0.07, p=0.83). TNFα$^{-/-}$ mice have significantly higher locomotion in response to the test dose than WT mice (Student's t-test, $t_{(27)}$=3.77, p<0.001). FIG. 5I shows that blocking soluble TNFα signaling only during the sensitization protocol (DN-TNF sensi) with DN-TNF is sufficient to sustain the elevation of the cocaine response to the challenge dose on day 15, while blocking TNFα signaling during the withdrawal period (DN-TNF withd) had no effect on the response to the challenge dose after withdrawal. (n=16 DN-TNF sensi, 8 DN-TNF withd, 12 Control). Two way-repeated-measures ANOVA (treatment, $F_{(2,34)}$=0.26, p=0.018; days, $F_{(4,31)}$=3.22, p<0.0001; treatment×days, $F_{(4,32)}$=0.31, p=0.05). Results are expressed as means (±S.E.M.). * p<0.05,  p<0.01, * p<0.001.

FIG. 6A is a graph showing mean locomotor activity in response to cocaine in mice that lack microglial TNFα (CX3CR1-Cre$^+$; TNFα$^{flox/flox}$) and littermate controls (CX3CR1-cre negative or TNFα$^{+/flox}$). (n=16 control; 12 microglia deletion; two way-repeated-measures ANOVA: genotype, $F_{(1,26)}$=0.33, p=0.006; days, $F_{(4,23)}$=7.8, p<0.0001; genotype×days, $F_{(4,23)}$=0.52, p=0.03). The elevation was sustained for a test dose of cocaine following withdrawal (Student's t-test, $t_{(26)}$=2.10, p<0.04). FIG. 6B is a graph showing mean locomotor activity in response to cocaine injections in mice that lack astrocytic TNFα (GFAP-Cre$^+$; TNFα$^{flox/flox}$ and littermate controls (GFAP-cre$^-$; TNFα$^{flox/flox}$). GFAP-Cre mice did not display altered behavioural sensitization (n=25 per condition; two way-repeated-measures ANOVA: genotype $F_{(1,38)}$=0.0048, p=0.67; days, $F_{(7,32)}$=5.8, p<0.0001; genotype×days, $F_{(7,32)}$=0.035, p=0.99). GFAP-Cre mice showed normal behavioral sensitization to cocaine on the test day (Student's t-test, $t_{(48)}$=0.83, p=0.41). FIG. 6C is a chart showing that purified microglia (CD11b+ fraction of cells) from whole striatum tissue express significantly more TNFα mRNA compared to other cell types (CD11b− fraction) (n=6 experiments, 5 mice pooled per group in each experiment; Steel multiple comparison test, z=2.99, p=0.0028). FIG. 6D is a chart showing that 5 daily injections of cocaine increase TNFα mRNA in microglia (n=4 experiments, 5 mice pooled per group in each experiment; Steel multiple comparison test, z=−2.31, p=0.0211). FIG. 6E shows representative confocal projection images of Iba1-labeled microglia in the nucleus accumbens from adult mice 24 hours after a single cocaine injection, 5 days daily injections or 10 days withdrawal (scale bar=20 µm). FIG. 6F is a chart showing a semi-quantitative analysis of Iba1 immunoreactivity in the nucleus accumbens. Values are normalized to the mean saline intensity for each time point. (n=3, 4, 7, 7, 4 mice (respectively); Student's one-tailed t-test, p=0.46, 0.038, and 0.029, respectively). FIG. 6G is a chart showing quantitation of microglia cell body size (µm$^2$) measured by Iba1 immunoreactivity and normalized to the mean saline value for each time point. (n=100 cells, 4 animals; Student's t-test, p=0.047). FIG. 6H displays representative examples of microglia processes, after 5 days of cocaine or saline. FIG. 6I is a chart showing total length of microglia processes, which is decreased after 5 days cocaine by 20%, but is not significantly altered after withdrawal (n=47 microglia (from 4 animals) and 41 (4) for 5 days cocaine and saline, 38 (4) and 39 (4) for cocaine and saline withdrawal; two-way ANOVA: time, $F_{(1,164)}$=2.663, p=0.105; drug, $F_{(1,164)}$=4.64, p=0.0327; time×drug, $F_{(1,164)}$=11.02, p=0.0011). Results are expressed as means (±S.E.M.). * p<0.05, ** p<0.01.

FIG. 7A shows primary rat microglia cultures treated with vehicle or dopamine (0.01 µm or 0.1 µm) for 3 h. (n=12, 6, and 13 biological replicates (respectively) from 4 independent cultures, ANOVA: $F_{(2,30)}$=3.6496, p=0.0390). FIG. 7B shows that treatment with cocaine (1 µm, 3 h) did not alter TNFα mRNA levels in microglia cultures (n=6 replicates from 3 cultures; Steel multiple comparison test, z=−0.194, p=0.847). FIG. 7C is a chart showing normalized change in TNFα mRNA in primary rat microglia cultures treated for 3 h with vehicle (Control), D1-receptor agonist (SKF-38393, 1 µm), D2-receptor agonist (quinpirole, 1 µm) or D3-agonist (pramipexole dihyrdochloride, 1 µm). (n=24 Control, 11 SKF, 13 quinpirole, 7 pramipexole replicates from 6 cultures, ANOVA: $F_{(3,51)}$=4.67; p=0.0061). FIG. 7D shows that 2 injections (i.p. 0.5 mg/kg) 24 hours and 1 hour before harvesting striatum tissue significantly increases TNFα mRNA specifically in microglia, compared to saline treatment (n=3 experiments, 4 mice pooled per group in each experiment; Wilcoxon Rank sum test, 1-way, p=0.037). FIG. 7E shows that co-administration of the D2-receptor antagonist L741,626 (i.p. 3 mg/kg) with daily cocaine injections over 5 days (D2 antagonist injected 15 min before cocaine) significantly decreases TNFα mRNA in ventral striatum tissue in adult mice (n=5 mice per group; Wilcoxon Rank sum test, 1-way, p=0.0075). FIG. 7F shows that co-administration of L741,626 with cocaine results in an increase in AMPA/NMDA ratio on D1-MSNs compared with cocaine alone treated animals (n=8-9 cells per condition; Student's t-test, $t_{(15)}$=2.72, p=0.026). Results are expressed as means (±S.E.M.). * p<0.05,  p<0.01, * p<0.001.

FIG. 8A shows on the left-hand side representative confocal projection images of Iba1 immunostaining in the nucleus accumbens obtained after 10 day withdrawal period of mice injected with cocaine for 5 days. One day prior to harvesting, mice were injected with either saline or MPLA (10 µg). Scale bar 20 µm. Semi-quantification of immunoreactivity reveals that Iba1 intensity was significantly increased 24 hours after a single MPLA injection as shown on the bar chart on the right-hand side. (n=5 mice control, 4 mice MPLA; Student's t-test, $t_m$=−4.09, p=0.006). FIG. 8B shows that a single injection of MPLA (10 µg) significantly increases TNFα mRNA in the ventral striatum after both 4 hours and 24 hours (n=4-5 mice per group, Steel multiple comparison test, z=−2.165, p=0.030 (4 hrs), z=−1.984, p=0.047 (24 hrs)). FIG. 8C shows representative traces and AMPA/NMDA ratios from D1-MSNs in the NAc core 24 hours after MPLA (10 µg) or saline injection in mice after 10 days withdrawal. (n=13 cells (from 2 mice) saline; 12 (2) MPLA; Student's t-test, $t_{(23)}$=2.04, p=0.05). FIG. 8D displays locomotor response to cocaine in wildtype mice. After withdrawal, mice were injected with MPLA (10 µg or 50 µg), and tested 24 hours later with a challenge dose of cocaine (15 mg/kg). MPLA dose dependently reduced the behavioral response to cocaine. (One-way ANOVA: $F_{(2,39)}$=32.96, p<0.0001; n=20 for control, 12 for 10 µg MPLA, and 10 for 50 µg MPLA). FIG. 8E shows that MPLA treatment had no effect on sensitization in TNFα$^{-/-}$ mice. An injection of MPLA (10 µg) did not reduce the locomotor response to a challenge dose of cocaine in TNFα$^{-/-}$ mice (Student's t-test, p>0.683; n=10 saline, 11 MPLA). FIG. 8F shows that MPLA does not reduce the initial response to cocaine. Animals were given 7 daily saline injections, then after 9 days of abstinence given an injection of saline or MPLA (10 µg), followed the next day by a challenge dose of 15 mg/kg cocaine. MPLA did not alter the response to the challenge dose (p=0.64). Further, this response is clearly lower than the sensitized response in control animals given cocaine during training. (One-way ANOVA: $F_{(2,19)}$=14.18, p<0.001; n=8 sal/sal, 7 sal/MPLA, 6 coc/sal). Results are expressed as means (±S.E.M.).* p<0.05,  p<0.01, * p<0.001.

Figure 11:
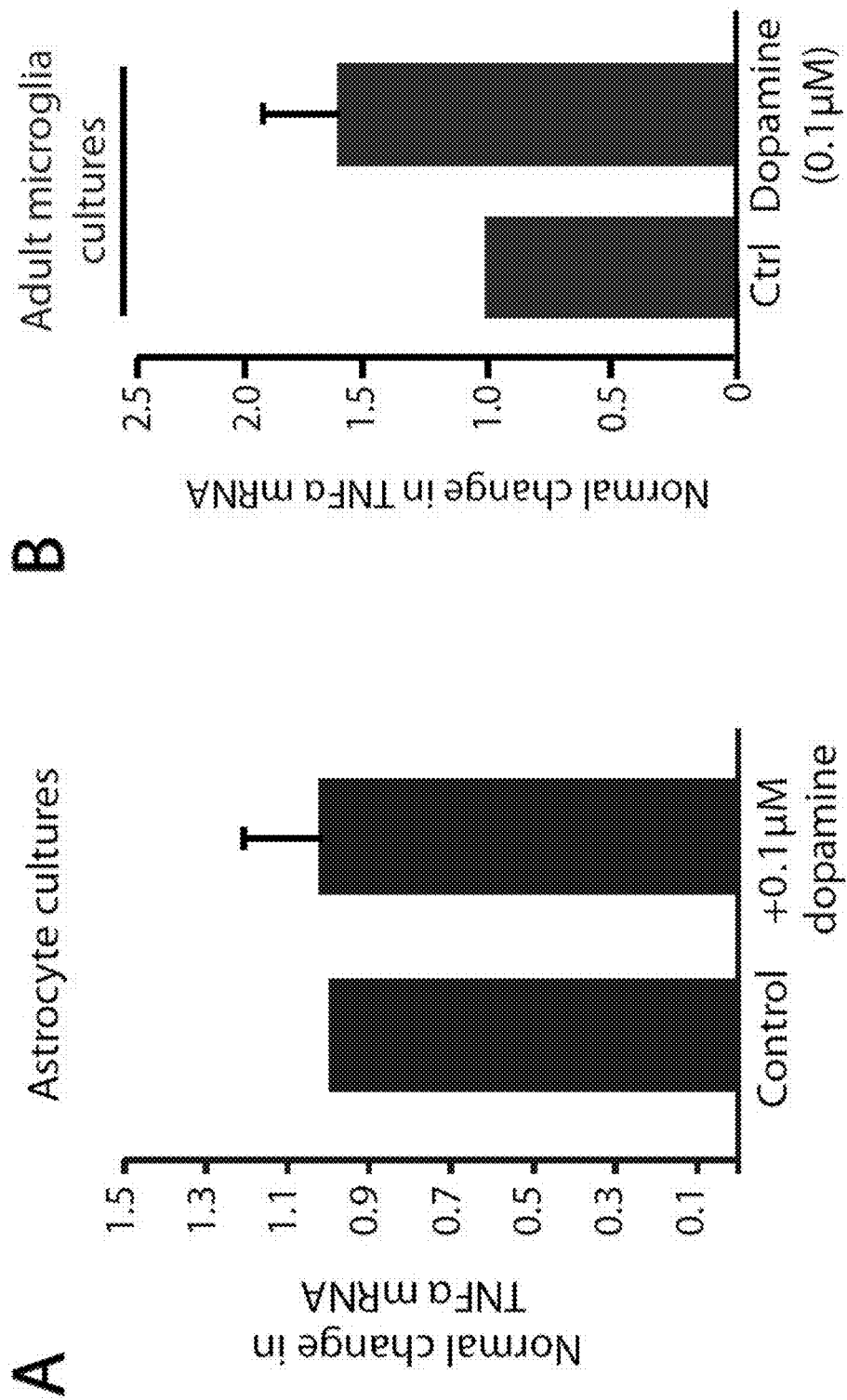
Figure 11:
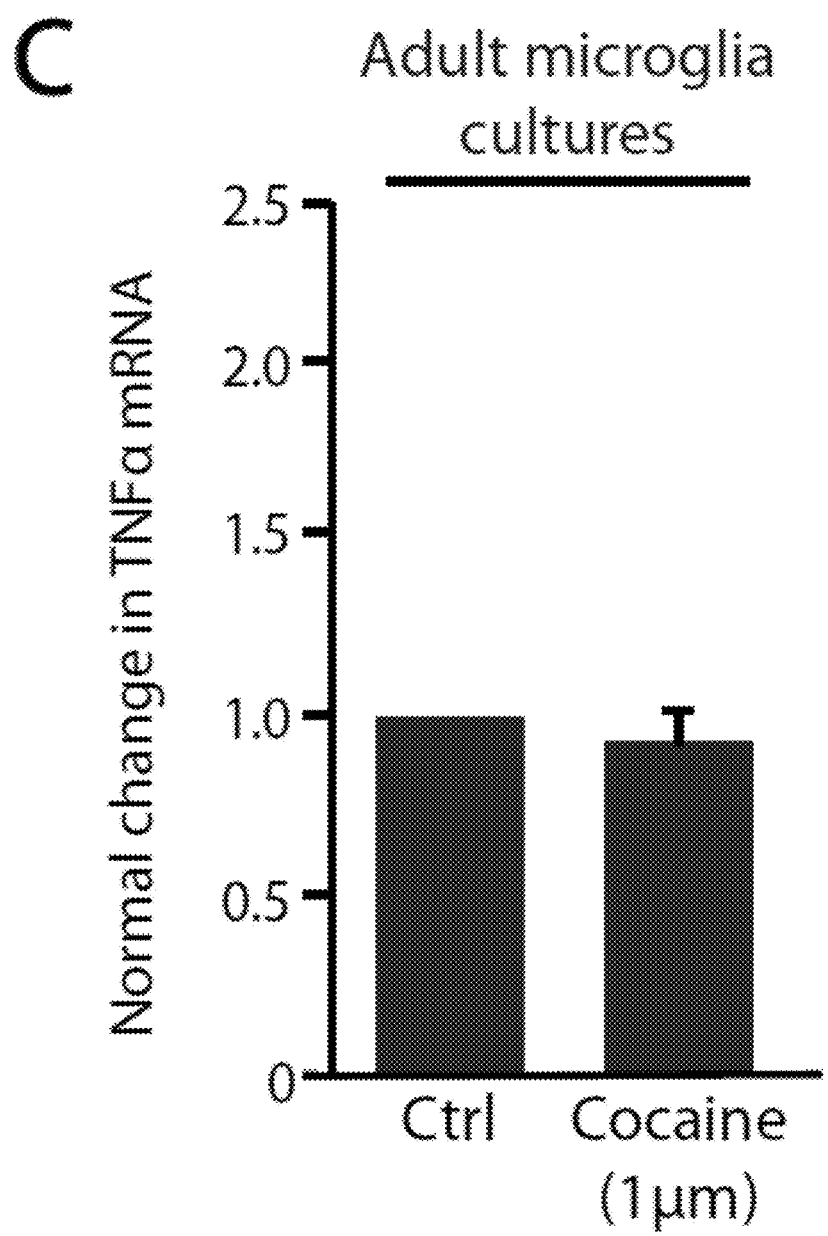

FIG. 11A is a bar chart showing that dopamine does not alter TNFα production in astrocytes. Primary rat astrocyte cultures treated with ascorbic acid alone (Control, 0.05 mg/mL), or with ascorbic acid and dopamine (0.1 μm) for 3 hours (n=6 biological replicates from 2 independent cultures; Steel multiple comparison rank sum test, p=0.81).

FIGS. 11B and 11C show cultures of adult microglial cells respond similarly to cultured neonatal microglia. Microglia were isolated from adult mice (see methods) and cultured for 7 days before being treated for 3 hours with either dopamine (0.1 μm) (FIG. 11B) or cocaine (1 μm) (FIG. 11C). Dopamine treatment had a trend for increasing TNFα mRNA to a similar magnitude to what was observed in microglial cultures from neonatal animals, although this effect was not significant (160% of control; n=6 animals per group; one-tailed paired t-test, p=0.057). Cocaine treatment did not alter TNFα mRNA (95% of control; n=3 animals per group; one-tailed paired t-test, p=0.33).

Figure 12:
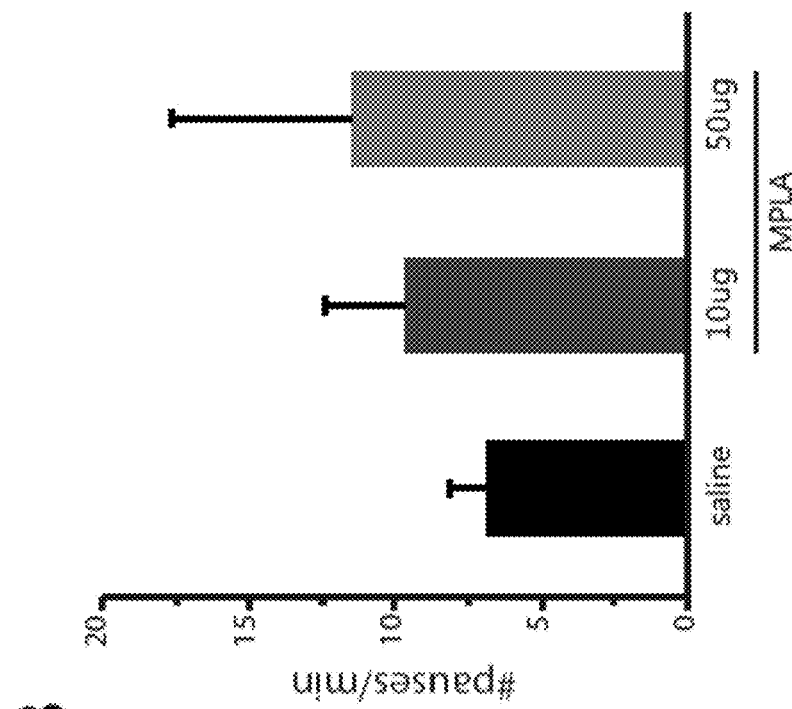
Figure 12:
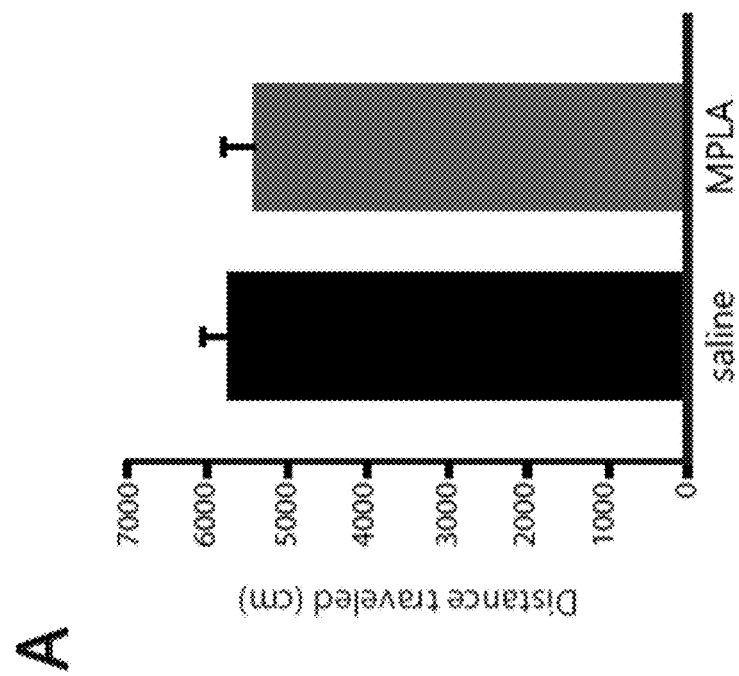
Figure 12:
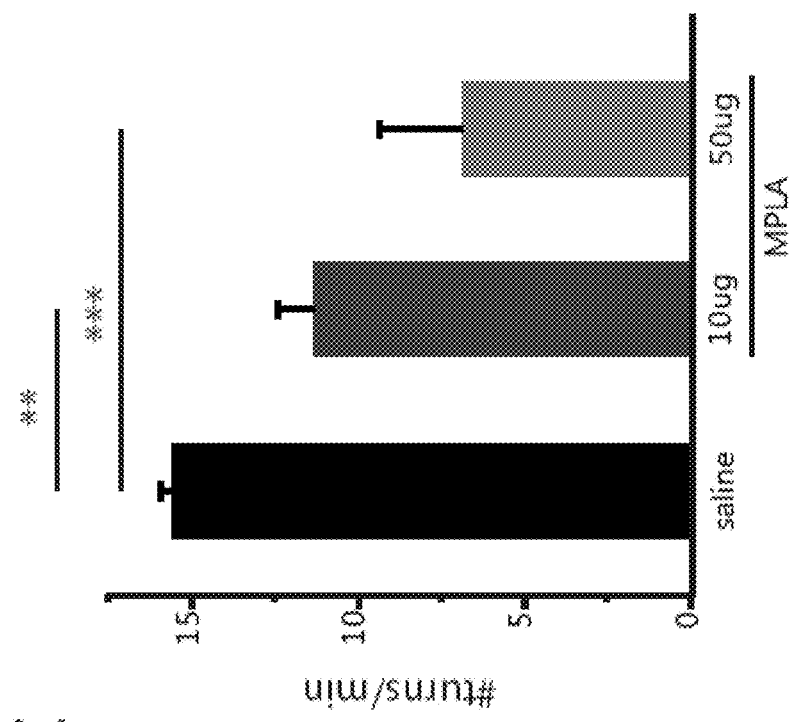
Figure 12:
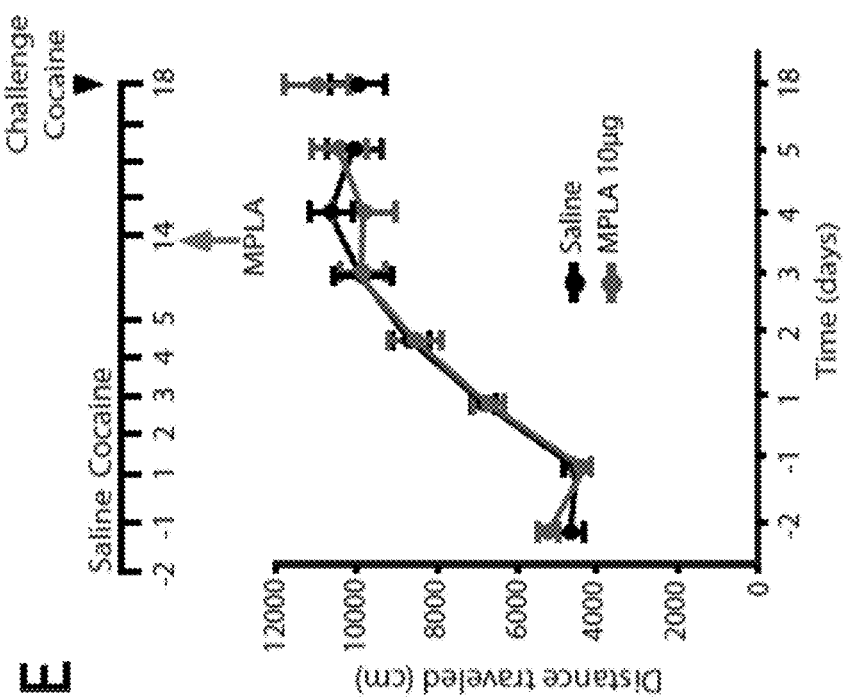
Figure 12:
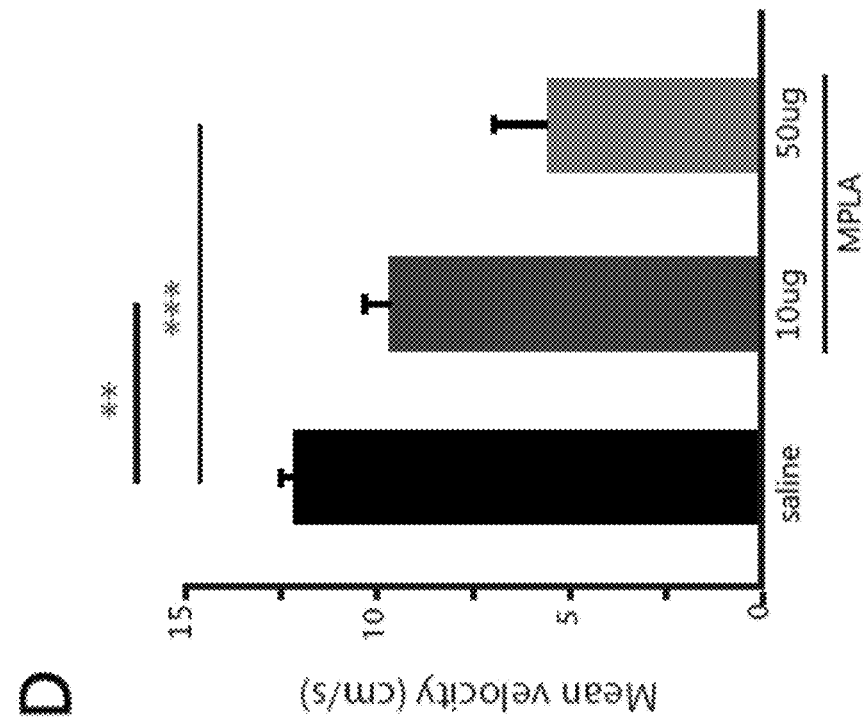

FIG. 12A is a bar chart showing that MPLA does not alter basal locomotion. No significant differences in locomotion were seen in mice tested 24 hours after an i.p. injection of 10 μg MPLA compared with saline injected mice (n=4 animals per group; Student's t-test, t(6)=0.067, p>0.52). FIG. 12B-D are bar charts showing that MPLA does not increase stereotypic responses to cocaine. For the locomotor response following MPLA injection in FIG. 8E, the behavioural response to cocaine for stereotypic behaviours was analyzed. MPLA treated animals (10 μg or 50 μg) had a slight increase in pausing (FIG. 12B), and significant decreases in turning behaviour (FIG. 12C) and in mean velocity (FIG. 12D) compared with saline injected controls. No evidence for an increase in stereotypic behaviours was seen, which suggests that the decrease in locomotor response to cocaine observed following MPLA is not due to increased sensitivity to cocaine and a corresponding increase in stereotypic behaviours. (Pausing: one-way ANOVA; F(2, 27)=0.667, p=0.521; n=14 for saline, 12 for 10 μg MPLA, and 4 for 50 μg MPLA. Turning: one-way ANOVA; F(2, 30)=12.566, p<0.0001; n=14 for saline, 15 for 10 μg MPLA, and 4 for 50 μg MPLA. Velocity: one-way ANOVA; F(2, 29)=17.729, p<0.0001; n=14 for saline, 15 for 10 μg MPLA, and 4 for 50 μg MPLA). FIG. 12E is a graph showing that MPLA suppression of sensitization is temporary. The delayed effect of a single MPLA injection (10 μg) on established behavioral sensitization in WT mice. After 10 days withdrawal, mice were injected with MPLA and were then tested for their cocaine response 4 days later. MPLA did not reduce the behavioral response to cocaine after 4 days (Student's t-test, p>0.336; n=15 for saline, 12 for 10 μg MPLA).  p<0.01, * p<0.0001.

Figure 13:
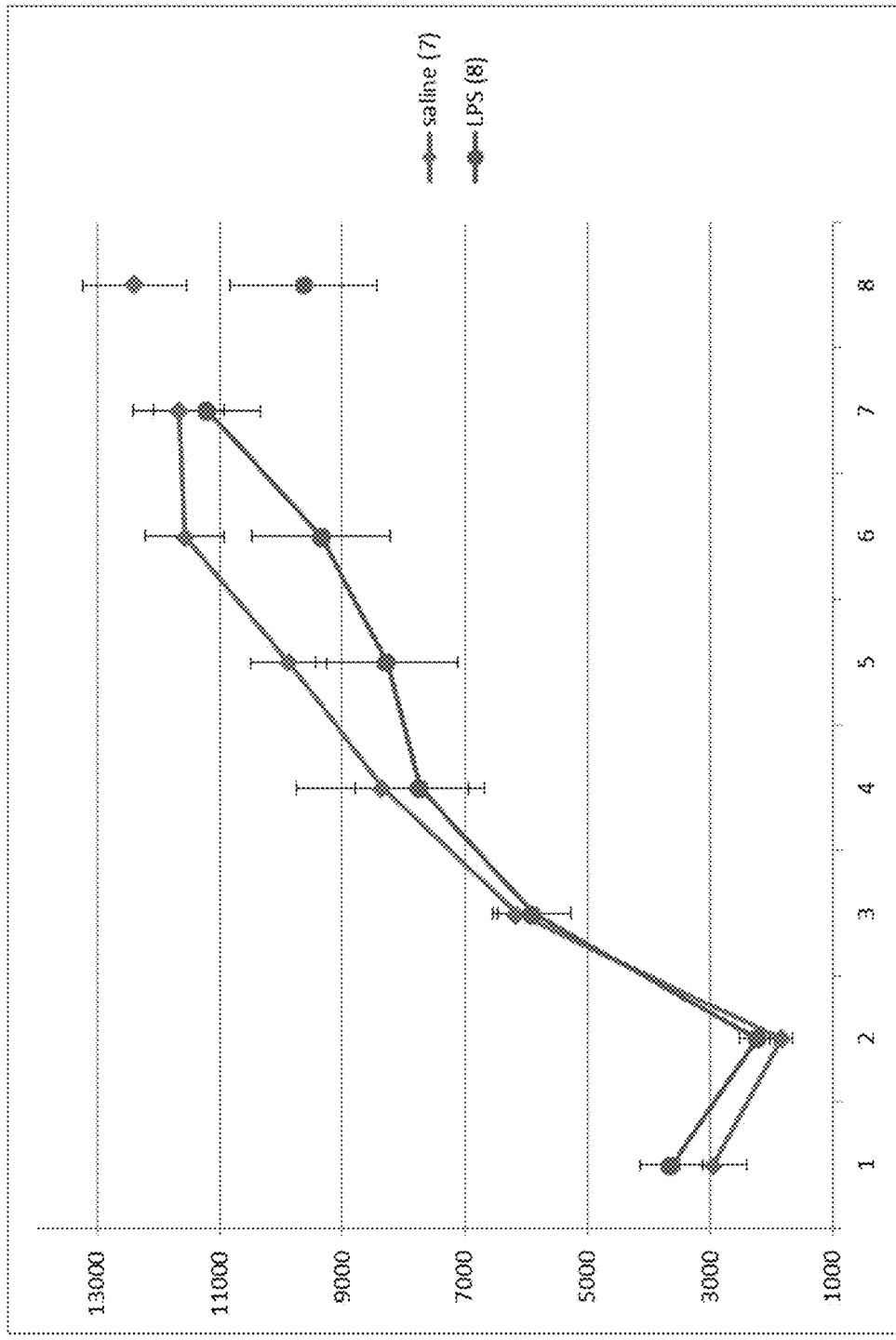

FIG. 13 is a graph showing that LPS reduced the sensitized response to cocaine. The average locomotor response (distance traveled (cm) in 15 minutes) was tested in mice treated with cocaine for 5 days, following a 9 day withdrawal period from cocaine, followed by an injection on day 9 of saline or LPS. 24 hours later the mice received a cocaine challenge dose.

DETAILED DESCRIPTION OF THE DISCLOSURE

1. Definitions

As used herein, the term "dosage form" refers to the physical form of a dose for example comprising a compound of the disclosure, and includes without limitation liquid and solid dosage forms including, for example tablets, including enteric coated tablets, caplets, gelcaps, capsules, ingestible tablets, buccal tablets, troches, elixirs, suspensions, syrups, wafers, resuspendable powders, liquids, solutions as well as injectable dosage forms, including, for example, sterile solutions and sterile powders for reconstitution, and the like, that are suitably formulated for injection.

The term "drug" in the context of "drug addiction" means a drug of abuse and includes for example cocaine, crack, morphine and morphine-like compounds, opioids, heroin, ecstasy, LSD, ketamine, tobacco, alcohol, caffeine, nicotine, *cannabis* and *cannabis* derivatives, phencyclidine and phencyclidine-like compounds, sedative hypnotics, pain-killers, psychostimulants, amphetamines and amphetamine-related drug or mixtures thereof.

As used herein, the term "effective amount" or "therapeutically effective amount" means an amount effective, at dosages and for periods of time necessary to achieve the desired result. For example, the effective amount is an amount that increases TNFα mRNA and/or protein levels, for example by at least 1.5 fold, optionally less than 10 fold, compared to untreated levels, for example in a NAc brain cell and/or decreases AMPA/NMDA ratios in D1-type medium spiny neurons, optionally by at least 15% compared to untreated D1-MSNs, optionally without inducing sickness behavior. Effective amounts may vary according to factors such as the disease state, age, sex, weight of the subject. The amount of a given compound that will correspond to such an amount will vary depending upon various factors, such as the given drug or compound, the pharmaceutical formulation, the route of administration, the type of disease or disorder, the identity of the subject or host being treated, and the like.

The term "lipopolysaccharide (LPS)" means purified and/or synthetic LPS. LPS is an constituent of the outer membrane of the wall of Gram-negative bacteria such as *Neisseria* spp. And *Haemophilus* spp. LPS comprises a lipid portion (lipid A) which is covalently bonded to a polysaccharide portion. Lipid A consists of two glucosamine units with attached acyl chains, for example 3, 4, 5, 6, 7, 8 or 10 acyl chains. LPS is also known as lipoglycans and includes low-molecular weight forms of bacterial LPS referred to as lipooligosaccharide (LOS). For example, LPS can be obtained from Sigma (cat# L4516; e-coli 0127:B8).

The term "detoxified LPS" means a modified form of LPS that has reduced pyrogenic activity compared to LPS. For example, detoxified LPS is at least 30 fold, 40 fold or 50 fold less pyrogenic than LPS at a similar molar concentration. Various methods of detoxifying LPS can be used to reduce toxicity and side effects of LPS. For example, US Pat. App. No. 20100291192 describes a detoxification method, which is incorporated by reference in its entirety, for LPS comprising mixing LPS with a cationic lipid to form a LPS-cationic lipid complex. LPS used herein refers to detoxified LPS that is suitable for administration in a subject, for example a human. For example, detoxified LPS includes derivatives thereof such as MPLA.

The term "monophosphoryl lipid A (MPLA)" also referred to as "MPL" or "MPL-A" means purified and/or synthetic MPLA, and can comprise for example MPLA with 3, 4, 5, 6, or 7 acyl groups or mixtures thereof, and be purified for example from *E. coli* and *Salmonella* species. MPLA is a TLR4 agonist and can for example induce TNFα mRNA and/or protein levels in a NAc cell by at least 1.5 fold and up to 50 fold compared to an untreated NAc cell. MPLA induces TNFα mRNA and/or protein levels in a NAc cell optionally 5 fold less than an equivalent molar amount of LPS, and with less pyrogenicity. MPLA is a detoxified derivative of Lipid A and can be obtained by removal of the core carbohydrate group and the phosphate from the reducing-end glucosamine for example by acid hydrolysis from R-form LPS. MPLA is sold for example by InvivoGen, San Diego Calif., USA which sells a synthetic lipid A from *E. coli*, serotype R515 (MPLAs) as a pure monophosphoryl lipid; and Corixa, Seattle Wash., USA which sells MPL derived from detoxified lipopolysaccharide (LPS), originating from the gram negative bacterium *Salmonella minnesota* R595 and is a mixture of congeners containing a β-1',6-linked disaccharide of 2 deoxy-2 aminoglucose, phosphorylated at the 4' position. For example, MPLA is also available from Adipogen, Sigma and GlaxoSmithKline. Fatty hydroxyacyl or acyloxyacyl groups are variously substituted at the 2,2', and 3' positions resulting in the total number of fatty acyl groups varying between 3 and 6. U.S. Pat. No. 4,436,727 discloses monophosphoryl lipid A (MPLA) molecules and their manufacture and is herein incorporated by reference in its entirety. The salt can for example be a pharmaceutically acceptable salt. MPLA as used herein includes but is not limited to MPLA and structurally related detoxified lipid A molecules such as 3-O-desacyl-4'-monophosphoryl lipid A (3D-MPLA), synthetic disaccharide molecules, similar in structure to MPLA and 3D-MPLA, glucopyranosyl lipid (GPL) molecules and the like as well as salts and solvates thereof. U.S. Pat. No. 4,912,094 and reexamination certificate B1 U.S. Pat. No. 4,912,094 discloses 3-O-deacylated monophosphoryl lipid A (3D MPLA) and EP 2437753 A1 discloses synthetic glucopyranosyl lipid adjuvants and their method of manufacture a method for its manufacture each of which are incorporated by reference.

The term "mixture" as used herein, means a composition comprising two or more compounds. In an embodiment, a mixture is a mixture of two or more distinct compounds. In a further embodiment, when a compound is referred to as a "mixture", this means that it can comprise two or more "forms" of the compounds, such as, salts, solvates, or, where applicable, stereoisomers of the compound in any ratio. A person of skill in the art would understand that a compound in a mixture can also exist as a mixture of forms. For example, a compound may exist as a hydrate of a salt. All forms of the compounds disclosed herein are within the scope of the present disclosure.

Where the compounds according to the disclosure possess one or more than one asymmetric centres, they may exist as "stereoisomers", such as enantiomers and diastereomers. It is to be understood that all such stereoisomers and mixtures thereof in any proportion are encompassed within the scope of the present disclosure. It is to be understood that, while the stereochemistry of the compounds of the disclosure may be as provided for in any given compound shown herein, such compounds may also contain certain amounts (e.g. less than 20%, less than 10%, less than 5%) of compounds having alternate stereochemistry.

The term "pharmaceutically acceptable" means compatible with the treatment of animals, in particular humans.

The term "pharmaceutically acceptable salt" means an acid addition salt or a basic addition salt which is suitable for, or compatible with, the treatment of patients.

The term "pharmaceutically acceptable acid addition salt" as used herein means any non-toxic organic or inorganic salt of any basic compound. Basic compounds that form an acid addition salt include, for example, compounds comprising an amine group. Illustrative inorganic acids which form suitable salts include hydrochloric, hydrobromic, sulfuric and phosphoric acids, as well as metal salts such as sodium monohydrogen, orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to one skilled in the art.

The term "pharmaceutically acceptable basic addition salt" as used herein means any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. The selection of the appropriate salt will be known to a person skilled in the art.

The formation of a desired compound salt is achieved using standard techniques. For example, the neutral compound is treated with an acid or base in a suitable solvent and the formed salt is isolated by filtration, extraction or any other suitable method.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

The term "subject" as used herein includes all members of the animal kingdom including mammals, and suitably refers to humans.

The term "Toll-like receptor 4 (TLR4) agonist" as used herein means any molecule that activates TLR4 and which increases TNFα mRNA and/or protein levels in a responsive cell (e.g. a NAc cell) by about or at least 1.5 fold, about or at least 2 fold, about or at least 3 fold, about or at least 4 fold, about or at least 5 fold, about or at least 6 fold, or about or at least 7 fold, and optionally less than for example 10 fold, less than for example 9 fold, less than for example 8 fold, less than for example 7 fold, less than for example 6 fold, less than for example 5 fold, less than for example 4 fold or less than for example 3.5 fold or a combination thereof, and which has a favourable safety profile, for example has a safety profile similar to MPLA. Examples of TLR4 agonists include but are not limited to a monophosphoryl lipid A or derivative thereof; amphotericin B; a lipopeptidophosphoglycan; fetuin A; Hsp60; a synthetic disaccharide molecule, similar in structure to MPL and 3D-MPL or a synthetic monosaccharide molecule, such as an aminoalkyl glucosaminide phosphate (AGP) and/or or derivative of any of the foregoing and/or mixtures thereof. The TLR4 agonist can be in an embodiment (+)morphine isomer which binds TLR4 but does not substantially bind the opioid receptor. For example, a TLR4 agonist increases TNFα levels in a responsive cell, for example 3 fold less, 5 fold less or 10 fold less than LPS for equivalent molar amounts.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of addiction, stabilized (i.e. not worsening) state of addiction, delay or slowing of addiction progression, amelioration, diminishment of the reoccurrence of the addiction, and remission (whether partial or total), whether detectable or undetectable. "Treating" and "Treatment" can also mean prolonging survival as compared to expected survival if not receiving treatment. "Treating" and "treatment" as used herein also include prophylactic treatment. In an embodiment, the compounds may be administered to the subject from about one time per three weeks, or about one time per week to about once daily for a given treatment. The length of the treatment period depends on a variety of factors, such as the severity of the addiction, the age of the patient, the concentration, the activity of the compounds described herein, and/or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required. For example, the compounds are administered to the subject in an amount and for a duration sufficient to treat the patient.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed ended terms that specify the presence of stated features, elements, components, groups, integers, and/or steps, and also exclude the presence of other unstated features, elements, components, groups, integers and/or steps.

Further, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

More specifically, the term "about" means plus or minus 0.1 to 50%, 5-50%, or 10-40%, 10-20%, 10%-15%, preferably 5-10%, most preferably about 5% of the number to which reference is being made As used in this specification and the appended claims, the singular forms "a", "an" and "the" include plural references unless the content clearly dictates otherwise. Thus for example, a composition containing "a compound" includes a mixture of two or more compounds. It should also be noted that the term "or" is generally employed in its sense including "and/or" unless the content clearly dictates otherwise.

The definitions and embodiments described in particular sections are intended to be applicable to other embodiments herein described for which they are suitable as would be understood by a person skilled in the art.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

Further, the definitions and embodiments described are intended to be applicable to other embodiments herein described for which they are suitable as would be understood by a person skilled in the art. For example, in the above passages, different aspects of the invention are defined in more detail. Each aspect so defined can be combined with any other aspect or aspects unless clearly indicated to the contrary. In particular, any feature indicated as being preferred or advantageous can be combined with any other feature or features indicated as being preferred or advantageous.

II. Methods and Compositions

Figure 3:
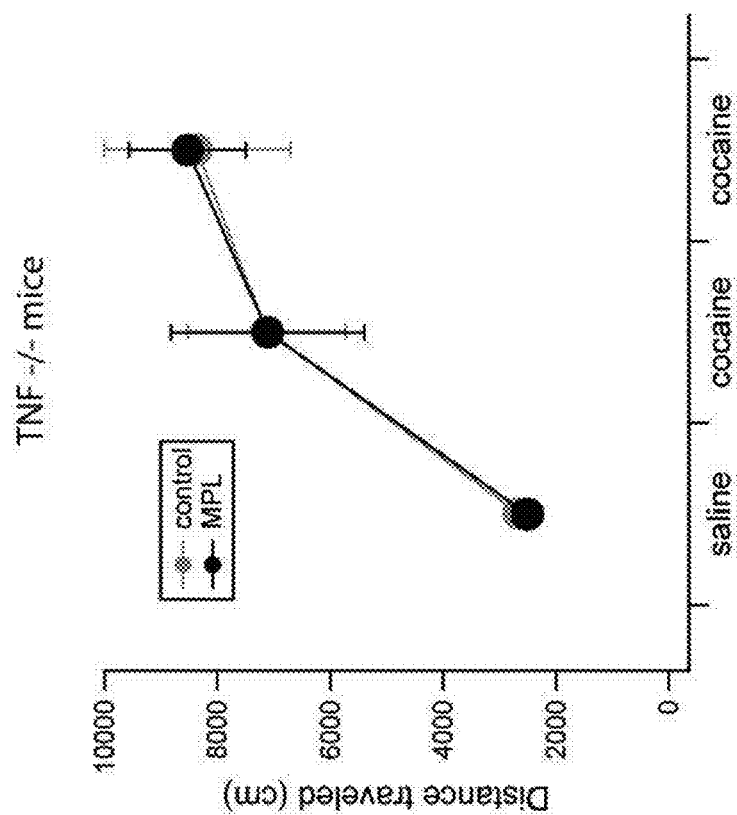
FIG. 3 is a series of graphs showing effects of MPLA in development of behavioural sensitization in wildtype mice (FIG. 3A) and in TNF−/− mice (FIG. 3B).
Figure 3:
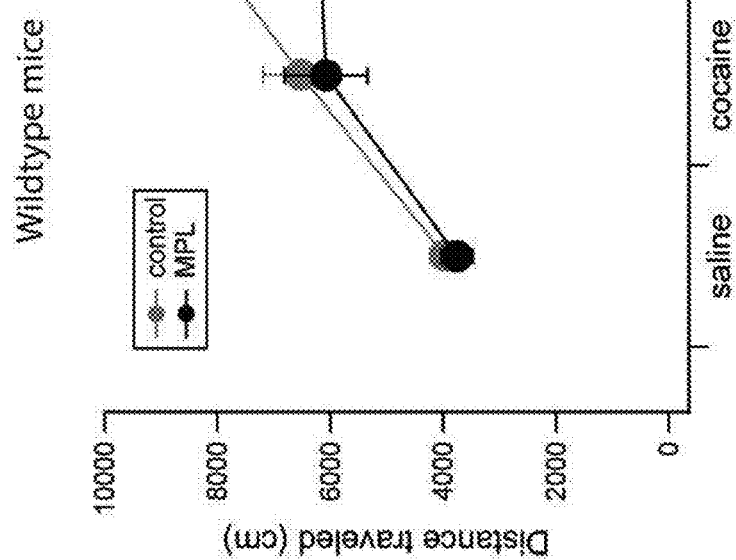
Figure 5:
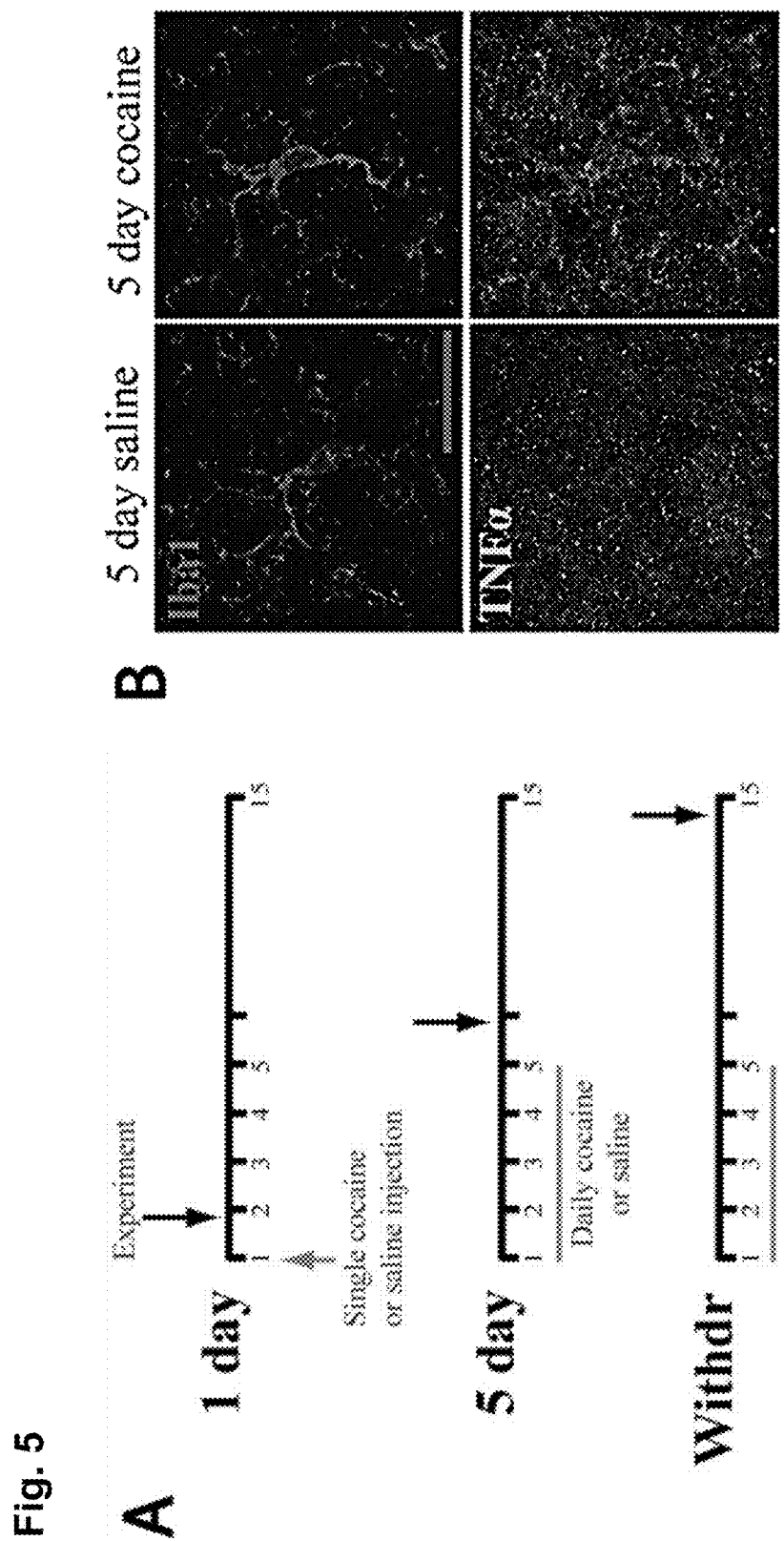
FIG. 5 is a series of charts, graphs and images showing that cocaine increases TNFα levels in the nucleus accumbens (NAc), which causes synaptic depression on D1-MSNs and antagonizes cocaine-induced behavioral sensitization.
Figure 5:
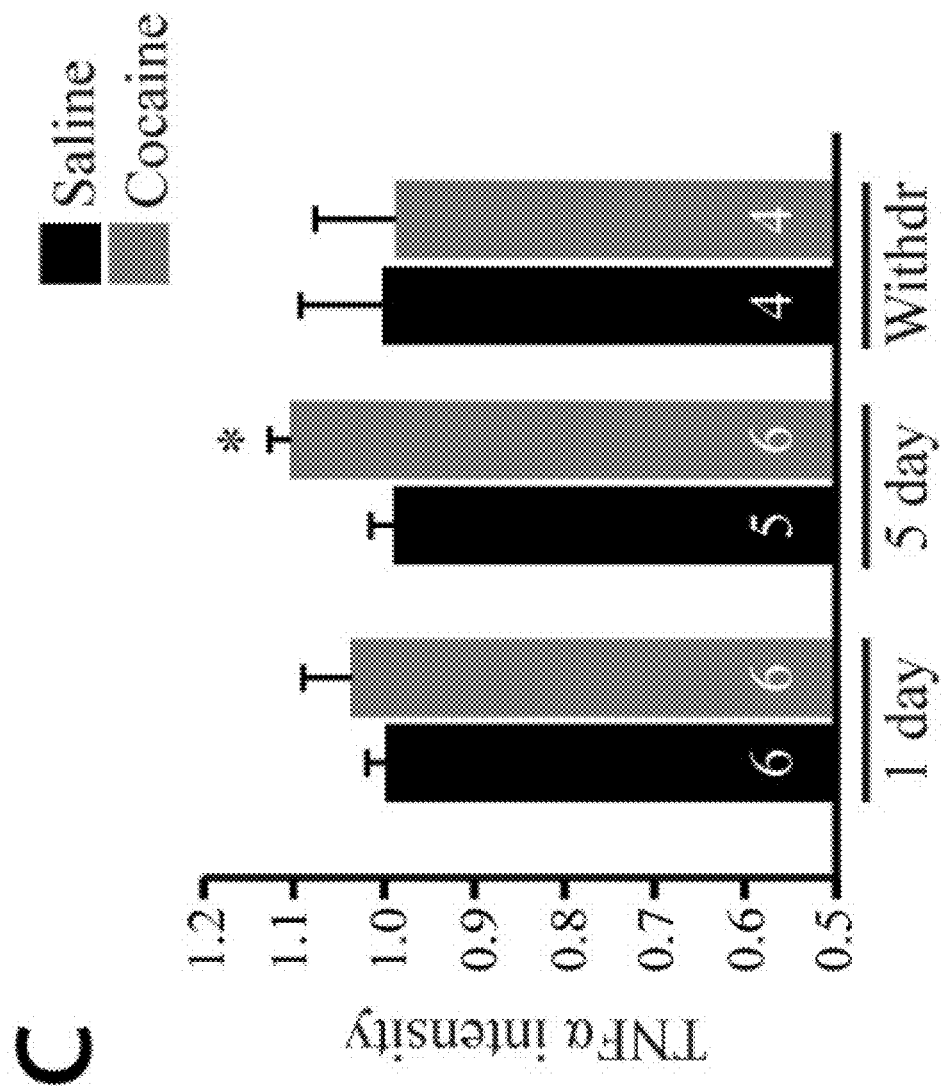
Figure 5:
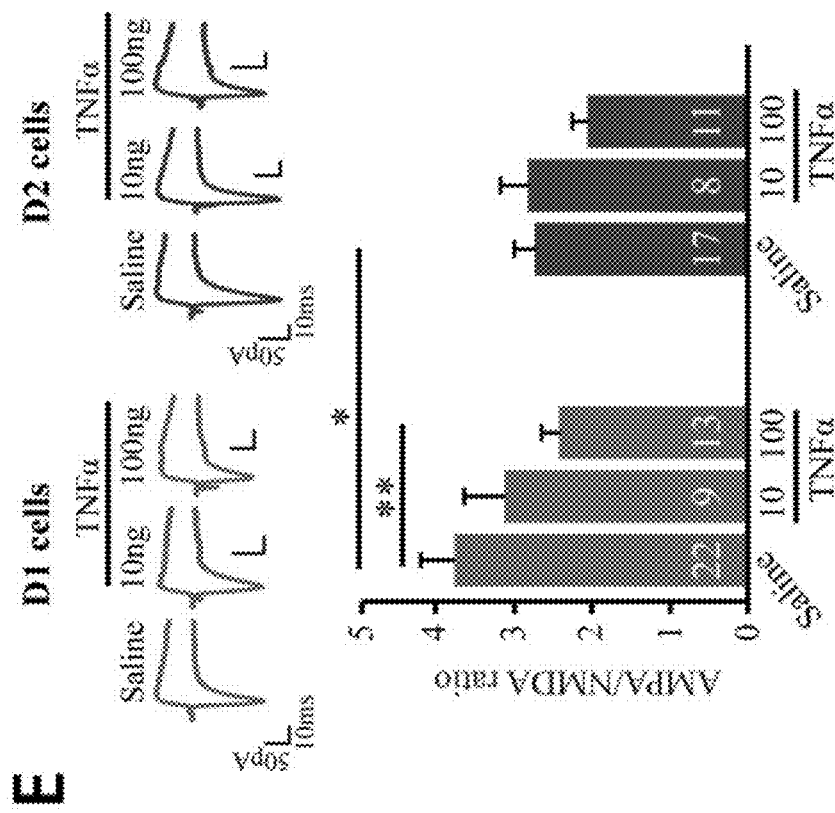
Figure 5:
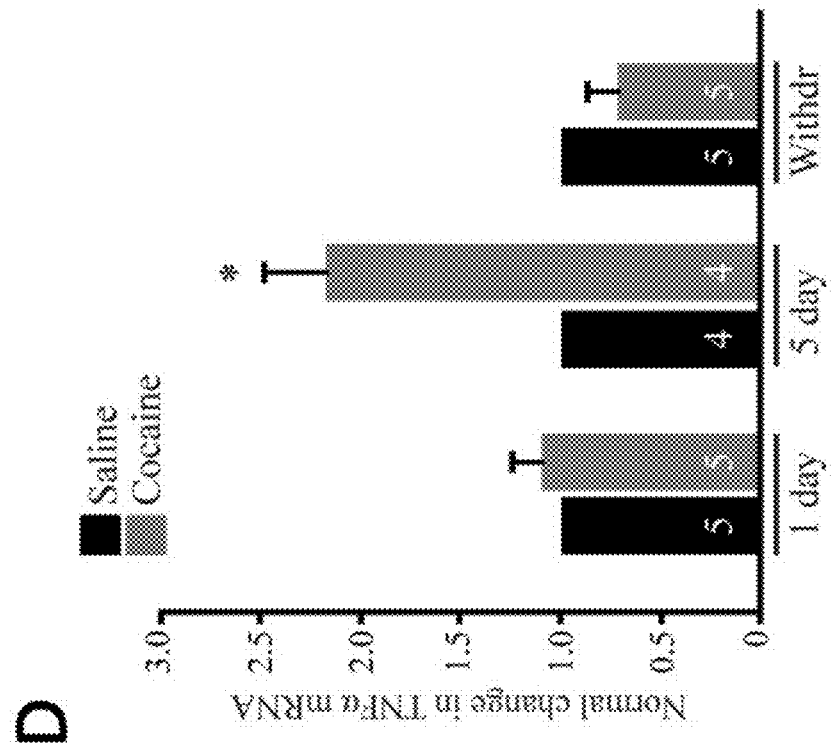
Figure 5:
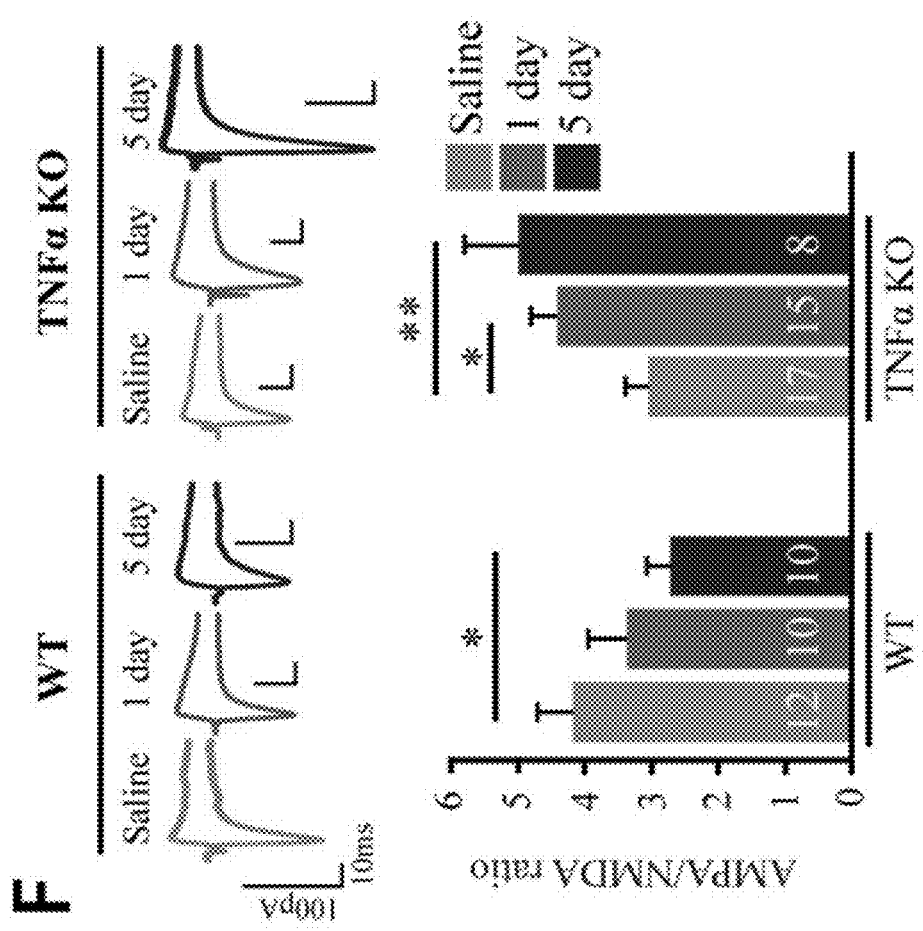
Figure 5:
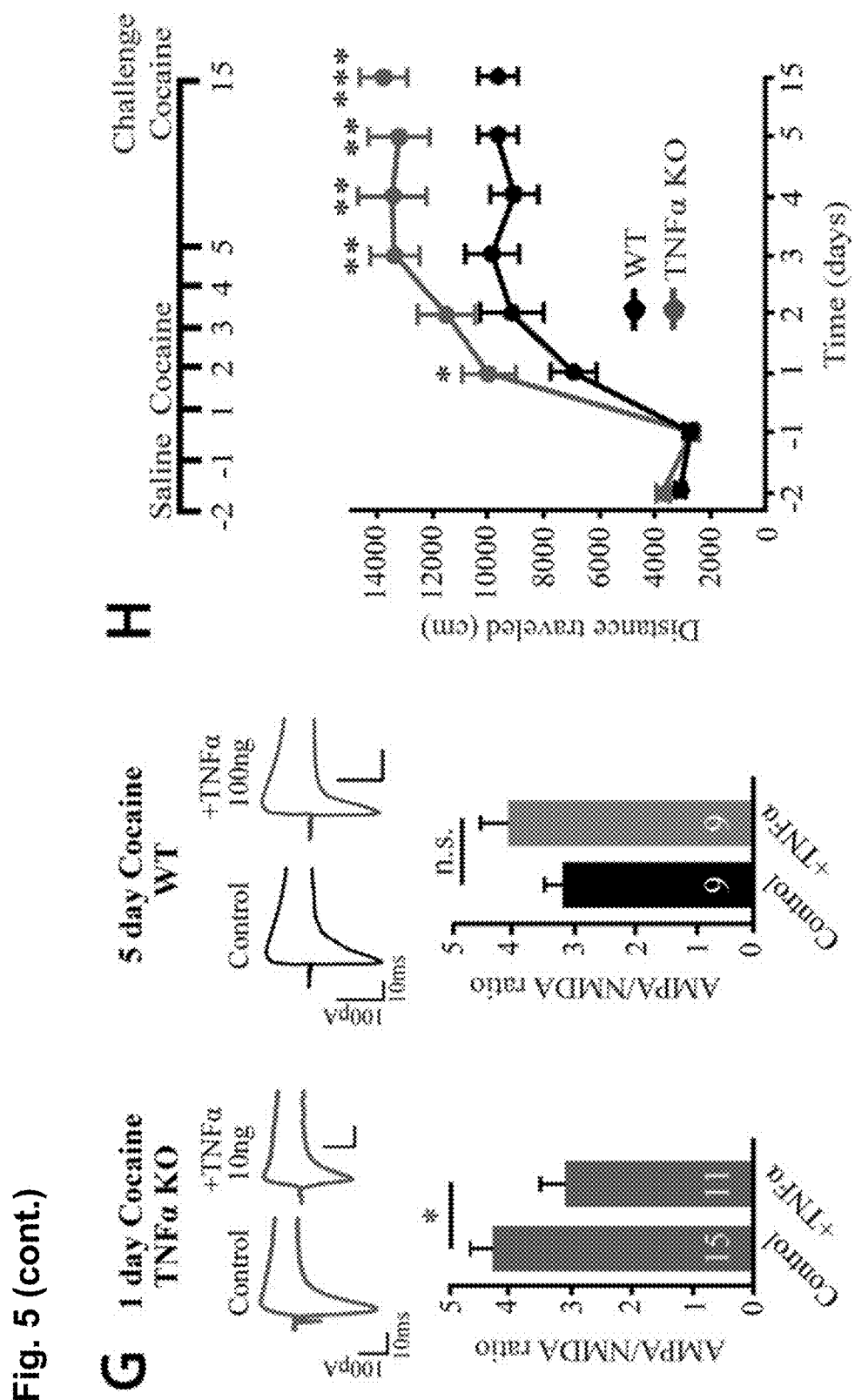
Figure 5:
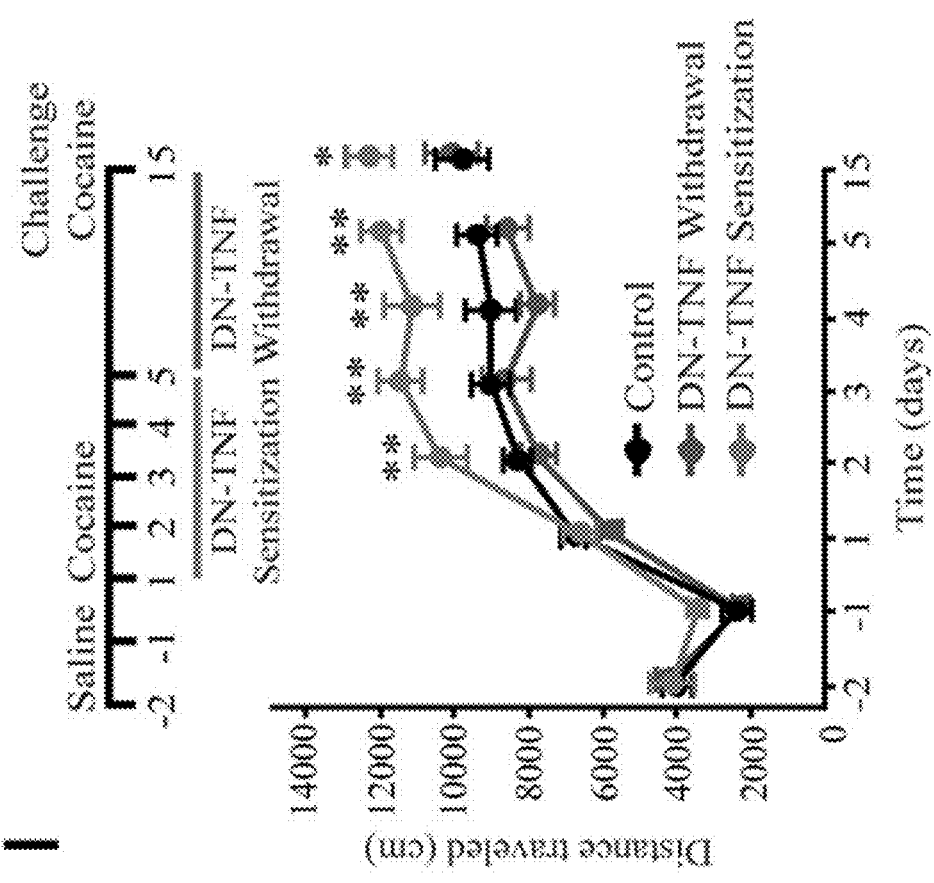

It is demonstrated herein that monophosphoryl lipid A (MPLA) reduces the development and expression of behavioural sensitization to cocaine. MPLA is a Toll-like receptor 4 (TLR4) agonist and is demonstrated herein to weakly increase TNFα levels (FIG. 5D). Removal of TNFα from the brain is demonstrated to increase behavioural sensitization to cocaine and the effect of MPLA is not seen in TNFα knockout mice (FIG. 3). Administering TNFα can induce neurotoxicity. MPLA has been used as a vaccine adjuvant and has a favourable toxicity profile. It is also demonstrated herein that MPLA reduces AMPA/NMDA ratios in D1-type medium spiny neurons.

Accordingly an aspect includes a method of reducing AMPA/NMDA ratio in D1-type medium spiny neurons (MSN) and/or reducing development of behavioural sensitization or suppressing drug induced behavioural sensitization in a subject optionally a subject that is afflicted with an addiction, comprising administering to the subject in need thereof an effective amount of a Toll-like receptor 4 (TLR4) agonist or a composition comprising said TLR4 agonist, optionally wherein the method is for reducing the likelihood of a subject developing or redeveloping a drug addiction and/or treating a subject afflicted with a drug addiction.

Also provided in another aspect is use of a TLR4 agonist or a composition comprising said TLR4 agonist reducing the likelihood of a subject developing or redeveloping a drug addiction and/or treating a subject afflicted with a drug addiction.

A further aspect includes a TLR4 agonist or a composition comprising said TLR4 agonist for use in a reducing the likelihood of a subject developing or redeveloping a drug addiction and/or treating a subject afflicted with a drug addiction and/or drug overdose.

In an embodiment, the amount administered and/or for use is an effective amount. For example, the amount administered is sufficient to increase TNFα levels in the subject. As described herein the levels activated in a mouse model were 10 fold less than activated with a similar dose of LPS. For example, the amount administered is sufficient to increase TNFα levels in a responsive cell by about or at least 1.5 fold, about or at least 2 fold, about or at least 3 fold, about or at least 4 fold, about or at least 5 fold, about or at least 6 fold, about or at least 7 fold and optionally less than for example 10 fold, less than for example 9 fold, less than for example 8 fold, less than for example 7 fold, less than for example 6 fold, less than for example 5 fold, less than for example 4 fold or less than for example 3.5 fold and/or a combination thereof.

In an embodiment the TLR4 agonist is a molecule that activates TLR4 signaling (and thereby activates TNFα levels), for example at a similar level to MPLA, and has a favourable toxicity profile, for example similar to MPLA. In an embodiment, the TLR4 agonist is selected from the group consisting of a monophosphoryl lipid A or derivative thereof; amphotericin B; a lipopeptidophosphoglycan; fetuinA; Hsp60; a synthetic disaccharide molecule, similar in structure to MPL and 3D-MPL or a synthetic monosaccharide molecule, such as an aminoalkyl glucosaminide phosphate (AGP) and/or or derivative of any of the foregoing and/or mixtures thereof. In an embodiment, the TLR4 agonist is the (+) morphine isomer.

As mentioned, it is demonstrated herein that MPLA is able to modulate the behavioural sensitization in a cocaine drug addiction model. Accordingly, in an embodiment, the TLR4 agonist comprises a monophosphoryl lipid A or derivative thereof and/or mixtures thereof.

The monophosphoryl lipid A or derivative thereof can be purified from a gram negative bacteria or be a synthetic monophosphoryl lipid, or derivative thereof. For example, MPLA and derivatives thereof can be purified from *E. coli* and *Salmonella* species, particularly from rough (R) bacteria (mutant/rough).

MPLA and its variants can be purified and processed from bacterial sources, or alternatively they may be synthetic.

Several patents have described MPLAs and derivatives thereof including for example U.S. Pat. No. 4,436,727 which discloses monophosphoryl lipid A (MPLA) and its manufacture; U.S. Pat. No. 4,912,094 and reexamination certificate B1 U.S. Pat. No. 4,912,094 discloses 3-O-deacylated monophosphoryl lipid A (3D MPLA). 3-O-deacylated monophosphoryl lipid A (3D-MPLA) is a further detoxified version of MPLA and can be produced by removal of the acyl chain from the 3-position of the disaccharide backbone, (3D-MPL). It can be purified and prepared by the methods taught for example in GB 2122204B, which reference also discloses the preparation of diphosphoryl lipid A, and 3-O-deacylated variants thereof. Purified monophosphoryl lipid A and 3-O-deacylated monophosphoryl or diphosphoryl lipid A derived from *Salmonella* sp. is also described in U.S. Pat. No. 4,912,094. 3D-MPL and the β(1-6) glucosamine disaccharides as well as other purified and synthetic lipopolysaccharides have been described (WO 98/01139; U.S. Pat. No. 6,005,099 and EP 0 729 473 B1, Hilgers et al., 1986 Int. Arch. Allergy Immunol., 79(4):392-6; Hilgers et al., 1987, Immunology, 60(1); 141-6; and EP 0 549 074 B1). Each of the foregoing references disclosing MPLAs and derivatives are herein incorporated by reference.

In an embodiment, the amount of MPLA administered is insufficient to induce sickness behavior, for example more than a 0.5° C. increase in body temperature.

In an embodiment, the amount of MPLA administered increases TNF-α levels in NAc cells by at least 1.5 fold, at least 2 fold, at least 3 fold, at least 4 fold, at least 5 fold, at least 10 fold, and less than 50 fold compared to untreated NAc cells.

In an embodiment, the amount of MPLA increases TNF-α levels in NAc cells at least 5 fold, at least 8 fold, at least 9 fold or at least 10 fold lower levels than LPS treated NAc cells.

In an embodiment, detoxified LPS is at least 10-fold, 50-fold, at least 60-fold, at least 70-fold, at least 80-fold, at least 90-fold or at least 100-fold less pyrogenic than LPS for equivalent molar amounts.

In an embodiment, the MPLA derivative a glucopyranosyl lipid (GPL). EP 2437753 A1 which discloses synthetic glucopyranosyl lipid adjuvants and their method of manufacture and is herein incorporated by reference.

In an embodiment, the GPL is compound IX disclosed in EP2437753 A1 and has the structure:

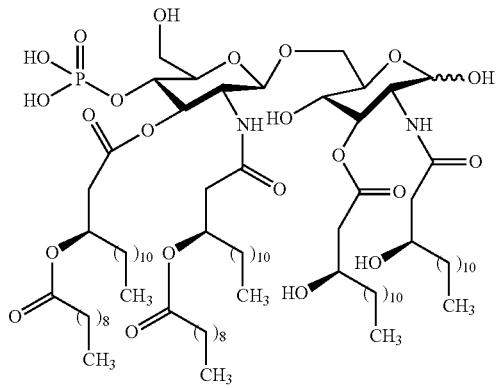

In another embodiment, the monophosphoryl lipid A, derivative and/or mixture thereof is MPLA or 3 de-acylated MPL (3D-MPL).

It is also demonstrated herein the LPS reduces behavioural sensitization to cocaine in mice.

In an embodiment, the LPS is purified or synthetic LPS.

Several patents describe methods for detoxifying LPS. For example, US Pat. App. No. 20100291192 describes a detoxification method for LPS comprising mixing LPS with a cationic lipid to form a LPS-cationic lipid complex. PCT Pat. App. No. WO1993013797 also describes methods for detoxifying LPS.

In one embodiment, the LPS is detoxified LPS.

In an embodiment, detoxified LPS is at least 50-fold, at least 60-fold, at least 70-fold, at least 80-fold, at least 90-fold or at least 100-fold less pyrogenic than LPS for equivalent molar amounts.

In another embodiment, the drug is selected from group consisting of cocaine, crack, morphine and morphine-like compounds, opioids, heroin, ecstasy, LSD, ketamine, tobacco, alcohol, caffeine, nicotine, *cannabis* and *cannabis* derivatives, phencyclidine and phencyclidine-like compounds, sedative hypnotics, pain-killers, psychostimulants, amphetamines and amphetamine-related drug or combinations thereof.

In another embodiment, the drug is selected from amphetamine, methamphetamine, opioids, alcohol, and nicotine.

In yet another embodiment, the drug is cocaine.

In a further embodiment, the drug is alcohol.

In yet another embodiment, the drug is methamphetamine.

For example, TLR4 agonist may be useful in treating addiction or preventing or reducing addiction to other addictive substances that elevate dopamine levels in the brain, for example in the reward pathway area. For example, the TL4 agonist may be useful in treating alcohol addiction.

TLR4 agonists and particularly MPLA, derivatives and/or mixtures thereof may be used to treat a variety of drug addictions and may be useful in suppressing relapse into addiction in subjects susceptible to regressing back to addictive state.

Accordingly, in an embodiment the method or use is for treating a subject with a drug addiction. In another embodiment, the method or use is for reducing the likelihood of the subject developing or redeveloping a drug addiction.

Figure 8:
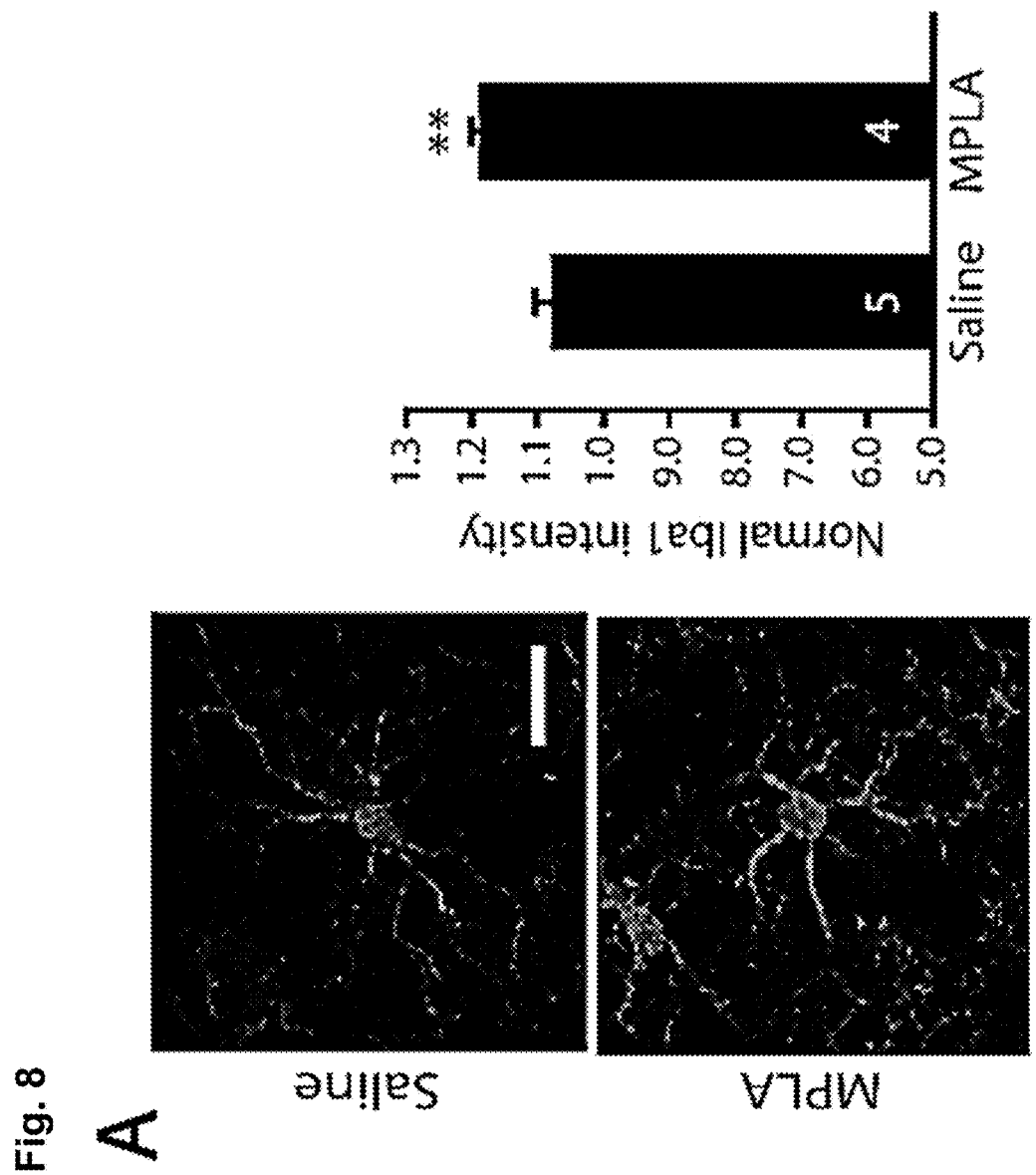
FIG. 8 is a series of charts, graphs and images showing that MPLA activates microglia in the nucleus accumbens and decreases behavioral sensitization to cocaine via TNFα.
Figure 8:
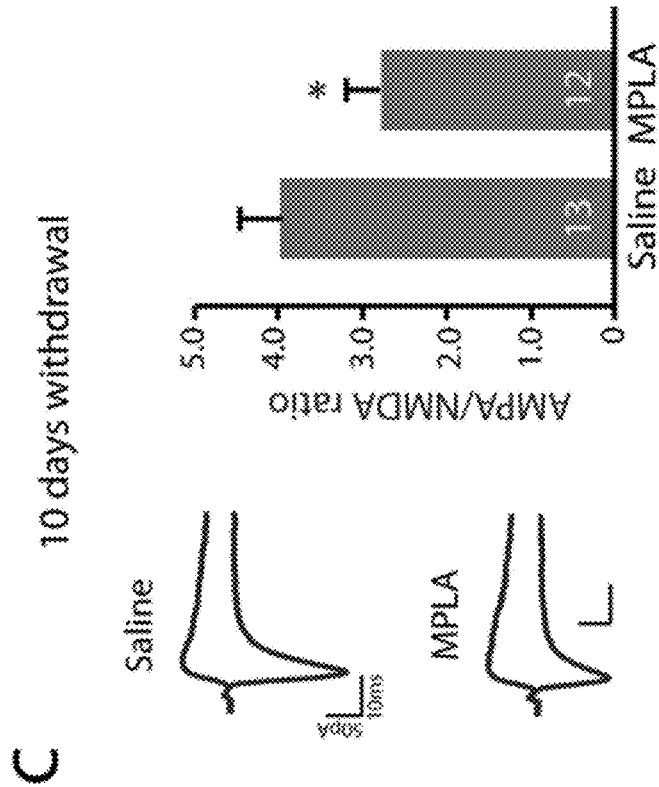
Figure 8:
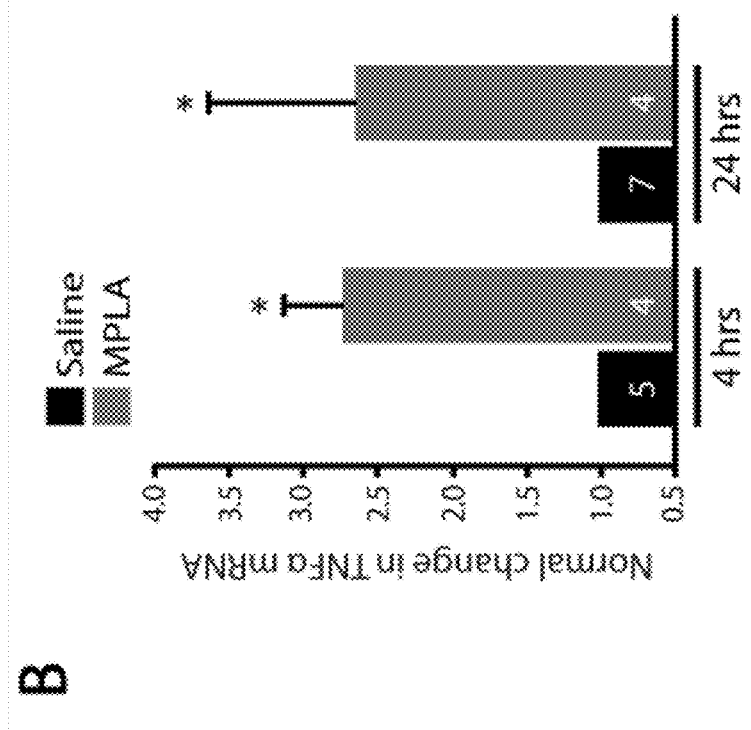
Figure 8:
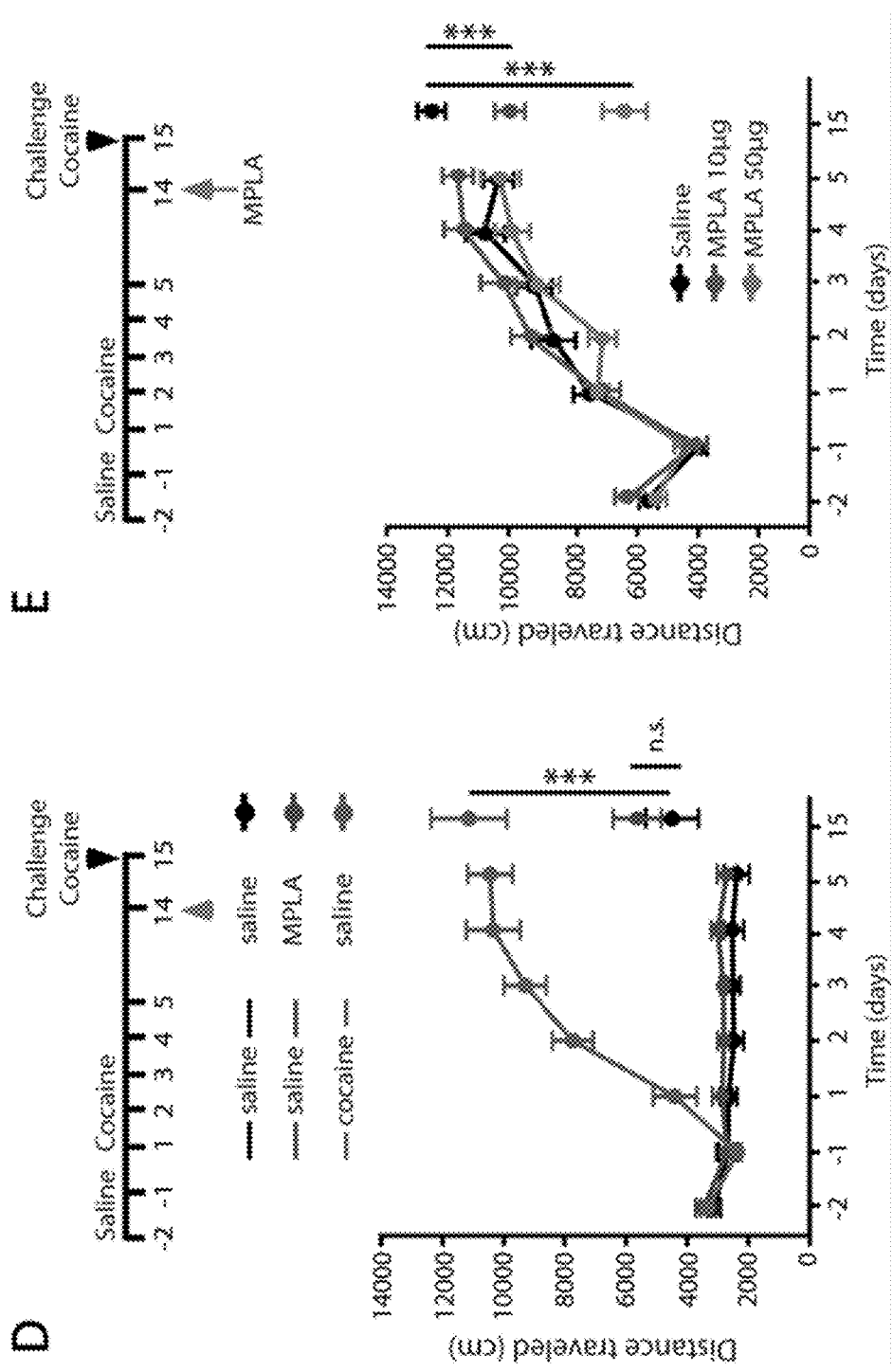
Figure 8:
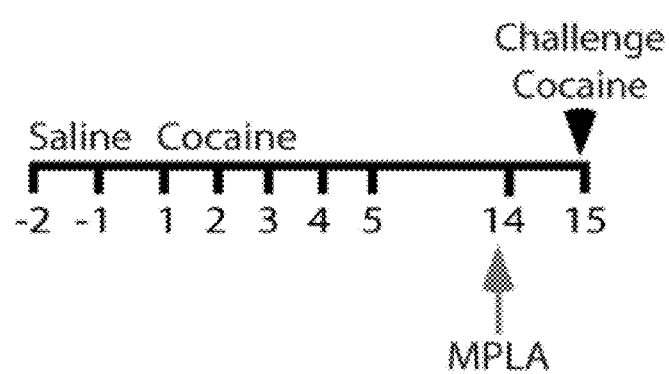
Figure 8:
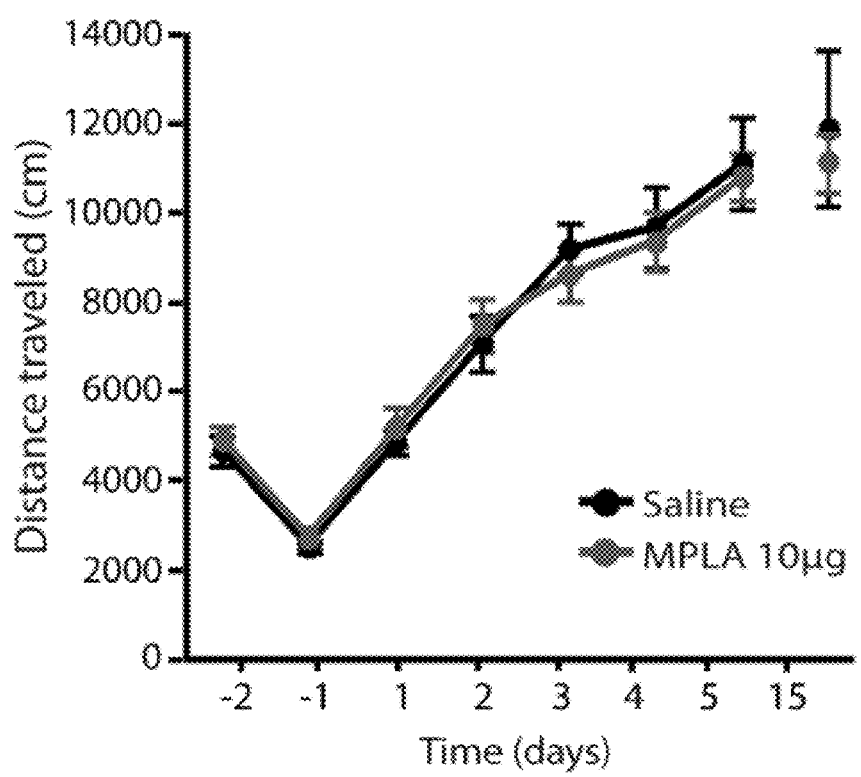

It is further demonstrated herein that MPLA treatment reduces AMPA/NMDA ratios in D1-type medium spiny neurons compared to saline treatment (FIG. 8C).

In an embodiment, the AMPA/NMDA ratio is reduced by at least 15%, at least 20%, at least 25%, at least 30%, at least 35% or at least 40% in D1-type MSNs compared to untreated D1-type MSNs.

Another aspect is a method for reducing AMPA/NMDA ratios in D1-type medium spiny neurons (MSN) comprising administering to a subject in need thereof a Toll-like receptor 4 (TLR4) agonist or a composition comprising said TLR4 agonist.

In an embodiment, the subject has a substance use disorder. For example, the substance use disorder is a drug addiction.

In another embodiment, the subject has a striatel based motor dysfunction. For example, the striatal-based motor dysfunction is dyskinesia or dystonia.

In another embodiment, the subject is afflicted by repetitive uncontrolled movements cause by striatal-based neuropsychiatric disorders for example obsessive compulsive disorder (OCD), autism and Tourette' syndrome.

In a further aspect, there is provided a method of reducing development of behavioural sensitization comprising administering to the subject in need thereof an effective amount of a Toll-like receptor 4 (TLR4) agonist or a composition comprising said TLR4 agonist.

Yet another aspect described herein is a method of suppressing drug induced behavioural sensitization comprising administering to the subject in need thereof an effective amount of a Toll-like receptor 4 (TLR4) agonist or a composition comprising said TLR4 agonist.

In a further aspect there is provided a method of reducing the likelihood of a subject developing or redeveloping a drug addiction and/or treating a subject afflicted with a drug addiction comprising administering to the subject in need thereof an effective amount of a Toll-like receptor 4 (TLR4) agonist or a composition comprising said TLR4 agonist in combination with other methods for treating, reducing or preventing drug addiction, including detoxification, behavioural counseling, behavioural therapy, rehabilitation and pharmacological treatment.

The TLR4 agonist, for example the MPLA, a derivative and/or mixture thereof is suitably formulated into pharmaceutical compositions for administration to human subjects in a biologically compatible form suitable for administration in vivo.

A further aspect provides a dosage form comprising a TLR4 agonist and/or a pharmaceutical composition comprising said TLR4 agonist. The pharmaceutical compositions and dosage forms can be used in the methods and uses described. In an embodiment, the dosage form is for use in treating a subject with a drug addiction. In another embodiment, the dosage form is for use in reducing the likelihood of the subject developing or redeveloping a drug addiction.

In an embodiment, the composition or dosage form comprises TLR-4 agonist and liposome, for example the TLR-4 agonist is liposome encapsulated.

The compositions described herein can be prepared by per se known methods for the preparation of pharmaceutically acceptable compositions that can be administered to subjects, such that an effective quantity of the active substance is combined in a mixture with a pharmaceutically acceptable vehicle.

Suitable vehicles are described, for example, in Remington's Pharmaceutical Sciences (2003—20$^{th}$ edition). On this basis, the compositions include, albeit not exclusively, solutions of the substances in association with one or more than one pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which optionally further contain antioxidants, buffers, bacteriostats and solutes that render the compositions substantially compatible with the tissues or the blood of an intended recipient. Other components that are optionally present in such compositions include, for example, water, surfactants (such as Tween™), alcohols, polyols, glycerin and vegetable oils. Extemporaneous injection solutions and suspensions may be prepared from sterile powders, granules, tablets, or concentrated solutions or suspensions. The composition can be supplied, for example, but not by way of limitation, as a lyophilized powder which is reconstituted with sterile water or saline prior to administration to the subject.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), diolesyl-phosphotidyl-ethanolamine (DOPE), and liposomes. Such compositions should contain a therapeutically effective amount of the compound(s), together with a suitable amount of carrier so as to provide the form for direct administration to the subject.

In an embodiment, the compounds and compositions described herein are administered, for example, by parenteral, intravenous, subcutaneous, intramuscular, intracranial, intraorbital, ophthalmic, intraventricular, intracapsular, intraspinal, intracisternal, intraperitoneal, intranasal, aerosol or oral administration.

In an embodiment, the compound or composition is administered by intravenous infusion.

Wherein the route of administration is oral, the dosage form may be, for example, incorporated with excipient and used in the form of enteric coated tablets, caplets, gelcaps, capsules, ingestible tablets, buccal tablets, troches, elixirs, suspensions, syrups, wafers, and the like. The oral dosage form may be solid or liquid.

In an embodiment, the disclosure describes a pharmaceutical composition wherein the dosage form is a solid dosage form. A solid dosage form refers to individually coated tablets, capsules, granules or other non-liquid dosage forms suitable for oral administration. It is to be understood that the solid dosage form includes, but is not limited to, modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions can be formulated, e.g. liposomes or those wherein the active compound is protected with differentially degradable coatings, such as by microencapsulation, multiple coatings, etc. It is also possible to freeze-dry the compounds described herein and use the lyophilizates obtained, for example, for the preparation of products for injection.

In another embodiment, the disclosure describes a pharmaceutical composition wherein the dosage form is a liquid dosage form. A person skilled in the art would know how to prepare suitable formulations. Conventional procedures and ingredients for the selection and preparation of suitable formulations are described, for example, in Remington's Pharmaceutical Sciences (2003—20$^{th}$ edition) and in The United States Pharmacopeia: The National Formulary (USP 24 NF19) published in 1999.

In another embodiment, the disclosure describes a pharmaceutical composition wherein the dosage form is an injectable dosage form. An injectable dosage form is to be understood to refer to liquid dosage forms suitable for, but not limited to, intravenous, subcutaneous, intramuscular, or intraperitoneal administration. Solutions of compounds described herein can be prepared in water suitably mixed with a surfactant such as hydroxypropylcellulose. Or for example, can be prepared in a sodium chloride solution, for example a 0.9% sodium chloride solution or a dextrose solution for example a 5% dextrose solution.

Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2003—20$^{th}$ edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

In an embodiment, the dosage form comprises from about 1 mg to about 1000 mg of a MPLA, derivative thereof and/or mixture thereof. For example, the amount of MPLA, derivative or mixture thereof administered is about 10 mg/dose to about 500 mg/dose. In another specific embodiment, the amount of administered is about 10 mg/dose to about 250 mg/dose. In another specific embodiment, the amount administered is about 10 mg/dose to about 150 mg/dose. In another embodiment, the amount administered is about 10 mg/dose to about 100 mg/dose. In an embodiment, the dosage form comprises about or at least 10 mg, about or at least 20 mg, about or at least 30 mg, about or at least 40 mg, about or at least 50 mg, about or at least 60 mg, about or at least 70 mg, about or at least 80 mg, about or at least 90 mg, about or at least 100 mg, about or at least 125 mg about or at least 150 mg about or at least 175 mg, about or at least 200 mg, about or at least 225 mg, about or at least 250 mg of MPLA, a derivative thereof and/or a mixture thereof. It will be evident to those skilled in the art that the number and frequency of administration will be dependent upon the response of the host.

In an embodiment, the dosage comprises about 0.05 µg/kg to about 100 mg/kg TLR4 agonist, optionally MPLA, a derivative thereof and/or a mixture thereof. In another specific embodiment, the dosage is about 0.05 to about 50 mg/kg. In another embodiment, the dosage is about 0.05 to about 25 mg/kg. In an embodiment, the dosage is about 0.05 µg/kg to about 10 mg/kg. In another embodiment, the dosage is about 0.05 to about 5 mg/kg. In another specific embodiment, the dosage is about 0.05 to about 1 mg/kg.

In an embodiment, the TLR4 agonist, optionally MPLA is administered after a period of withdrawal from drug consumption can decrease sensitization to cocaine.

In one embodiment, the TLR4-agonist, optionally MPLA or LPS, is administered to the subject in need thereof after a drug withdrawal period. For example, the drug is administered to the subject after a period of 1, 2, 3, 4, 5, 6, 7, 8, 9 or 10 days after last drug use.

In another embodiment, the TLR4-agonist, optionally MPLA or LPS, is administered to the subject in need thereof during the time the drug is used.

The duration of administration of a TLR4-agonist may vary according to the type of TLR4-agonist, the subject and according to the drug substance but may vary from at least 1 day, at least 2 days, at last 3 days, at least 4 days, at least 5 days, up to 10 days, up toll days or up to 12 days.

Frequency of TLR4-agonist may vary according to the TLR4-agonist dosage, the type of TLR4-agonist, the subject and according to the drug substance but can be administered for example once a day, every other day, every three days or every four days.

A further aspect is a kit comprising a TLR4 agonist and/or a composition comprising said TLR4 agonist and instructions for use to reduce the likelihood of a subject developing or redeveloping a drug addiction and/or treating a subject afflicted with a drug addiction and/or drug overdose.

In an embodiment, the kit comprises a dosage form comprising a TLR4 agonist and/or a composition comprising such TLR4 agonist. In an embodiment, the dosage form or kit comprises a TLR4 agonist selected from the group consisting of a monophosphoryl lipid A or derivative thereof; amphotericin B; a lipopeptidophosphoglycan; fetuin A; Hsp60: a synthetic disaccharide molecule, similar in structure to MPL and 3D-MPL or a synthetic monosaccharide molecule, such as an aminoalkyl glucosaminide phosphate (AGP) and/or derivative of any of the foregoing and/or mixtures thereof.

In an embodiment, the composition comprises a pharmaceutically acceptable carrier.

In an embodiment, the dosage form or kit comprises a TLR4 agonist wherein the TLR4 agonist comprises a monophosphoryl lipid A, derivative thereof and/or mixtures thereof.

In an embodiment, the monophosphoryl lipid A, derivative thereof and/or mixture thereof in the dosage form or kit is purified from a bacteria or is synthetic monophosphoryl lipid. In an embodiment the bacteria is *Salmonella*.

In another embodiment, the kit or dosage form comprises a glucopyranosyl lipid (GPL).

In another embodiment, the kit or dosage form comprises MPLA.

In yet another embodiment, the kit or dosage form comprises 3 de-acylated MPL (3D-MPL) and/or mixture thereof.

In another embodiment, the kit comprises instructions-and/or the dosage form is for use in reducing the likelihood of developing or redeveloping or for use in treating a drug addiction wherein the drug is selected from group consisting of cocaine, crack, morphine and morphine-like compounds, opioids, heroin, ecstasy, LSD, ketamine, tobacco, alcohol, caffeine, nicotine, *cannabis* and *cannabis* derivatives, phencyclidine and phencyclidine-like compounds, sedative hypnotics, pain-killers, psychostimulants, amphetamines and amphetamine-related drug or mixtures thereof. In an embodiment, drug is selected from amphetamine, methamphetamine, opioids, alcohol, and nicotine. In yet another embodiment, the drug is cocaine or alcohol.

In another embodiment, the kit further comprises and/or the dosage form is for use with an additional compound for preventing or treating an addiction or withdrawal from drug consumption.

In a further embodiment, the dosage form is contained in a vial.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Blocking of TNF-α signaling both using genetic and pharmacological means augments cocaine behavioral sensitization. This suggests that TNF-α signaling is a physiological adaptive process that antagonizes cocaine-induced changes in behavior and synaptic plasticity. However, increasing TNF-α might come with risk of inducing Neuroinflammation.

MPL, a TLR4 ligand that is at least 100-fold less pyrogenic than LPS was tested. MPL was shown to increase TNF-α levels in vivo, but at 10 fold lower levels than LPS and without inducing sickness behavior. Therefore, MPL was used to moderately increase TNF-α to reduced behavioral sensitization to cocaine.

A cocaine induced behavioral sensitization animal model of drug addiction was used. Sensitization refers to the augmentation of behavioral responses to drugs of abuse that occurs during their repeated administration and persists long after drug exposure is discontinued. In this paradigm mice are injected with 15 mg/kg cocaine and put in an open field box and measure the cocaine stimulatory effects on locomotor for 15 min. After the first run mice are injected with 10 ug of MPL and returned to their home cage.

Figure 1:
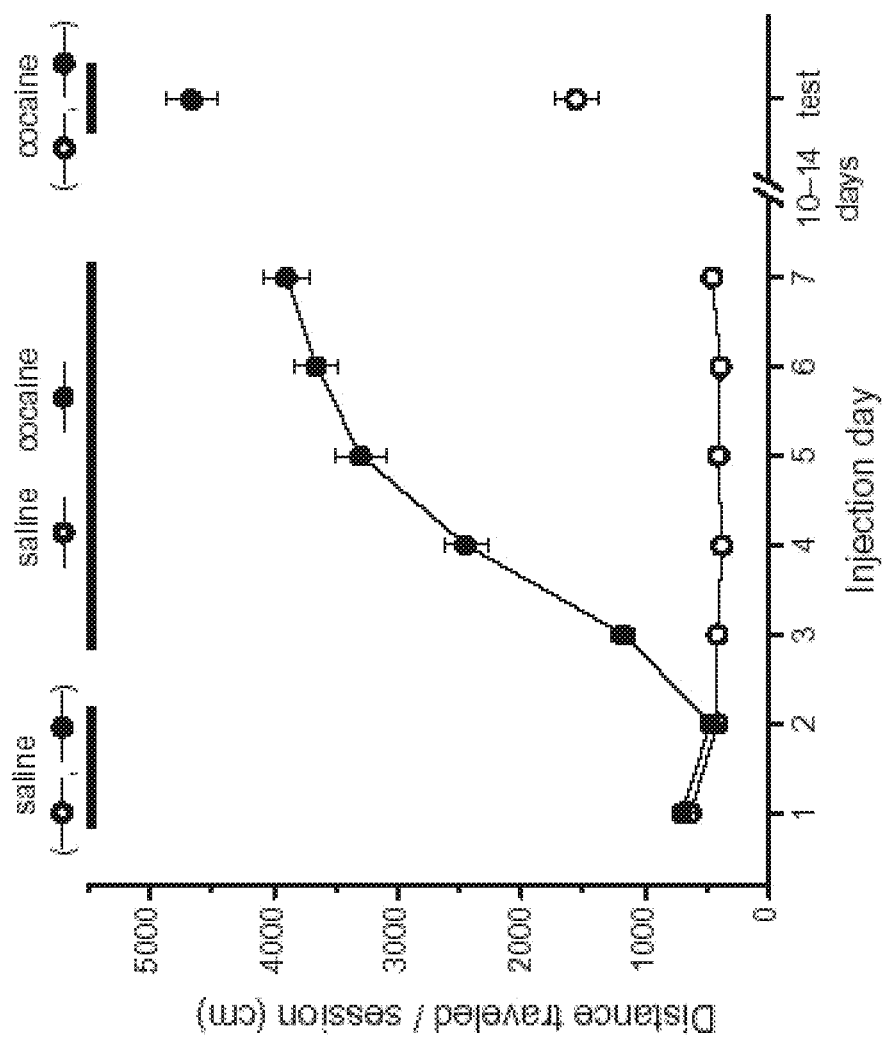
FIG. 1 is a graph showing effects of cocaine on locomotor response.

Behavioural Sensitization is a simple model of drug-induced behavioural change, which measures the progressive increase in the locomotor response to psychostimulants such as cocaine. Wildtype mice were injected daily with 15 mg/kg cocaine for 5 days (following two days of saline). After 10 days of withdrawal from the drug, the locomotor response to a test dose of cocaine was elevated (FIG. 1).

Removing the signaling molecule TNFα from the brain greatly increases the amount of behavioural sensitization. Wildtype mice were injected daily with 15 mg/kg cocaine for 5 days (following two days of saline). After 10 days of withdrawal from the drug, the locomotor response to a test dose of cocaine was elevated in TNFα KO mice compared to wildtype mice.

Figure 2:
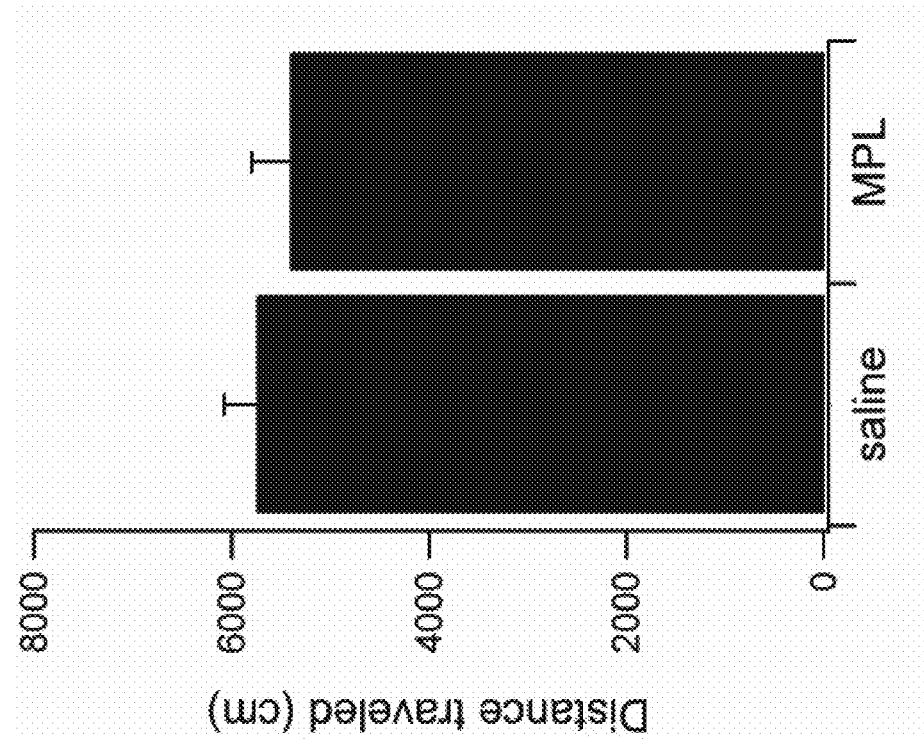
FIG. 2 is a graph showing effects of MPL on locomotor activity.

To determine whether the low TNFα response induced by MPLA can affect the behavioural response to cocaine, it was first assessed if MPLA can alter the basal locomotion of mice. Mice were injected with 10 ug of MPLA, and tested 24 hrs later. No difference in basal locomotion was observed (n=4), compared with saline injected control mice (FIG. 2).

MPLA was next tested in a simple test of drug-induced behavioural sensitization. In this test, mice display an increase in the locomotor response to repeated cocaine administration. The basal locomotor response was assessed, and the following day, the locomotor response to cocaine (15 mg/kg) was measured. MPLA (10 ug) was injected IP to wildtype or TNFα$^{-/-}$ mice and re-tested the locomotor response to cocaine one day later. MPLA reduced behavioral sensitization to cocaine 24 hours after the MPLA injection compared to saline treated mice. However, no effect of MPLA was observed in TNFα$^{-/-}$ mice, suggesting that MPLA is acting through an elevation of TNFα and not other cytokines. The These observations suggest that MPLA can transiently antagonize cocaine induced locomotor sensitization (FIG. 3).

Increasing the production of TNFα using MPL-A reduces the development of behavioural sensitization.

To evaluate whether MPLA can reduced the behavioral sensitization following prolonged withdrawal from cocaine, wildtype mice were injected daily with 15 mg/kg cocaine for 5 days. Even after 10 days of withdrawal from the drug, the locomotor response to a test dose of cocaine was elevated. Prior to the test dose of cocaine, mice were injected with either MPLA (10 ug or 50 ug) or saline and 24 hours later were tested for cocaine sensitization. Mice treated with MPLA had significantly reduced locomotor response in a dosage dependent manner. These observations suggest that even after a prolonged period of withdrawal from cocaine MPLA can still be effective in reducing behavioral response to cocaine. It also suggests that MPLA may help blunt craving in established addicts (FIG. 8E). Increasing the production of TNFα using MPLA also reduces the expression of behavioural sensitization.

The results show that MPL can reduce cocaine induced behavioral sensitization.

Example 2

Figure 4:
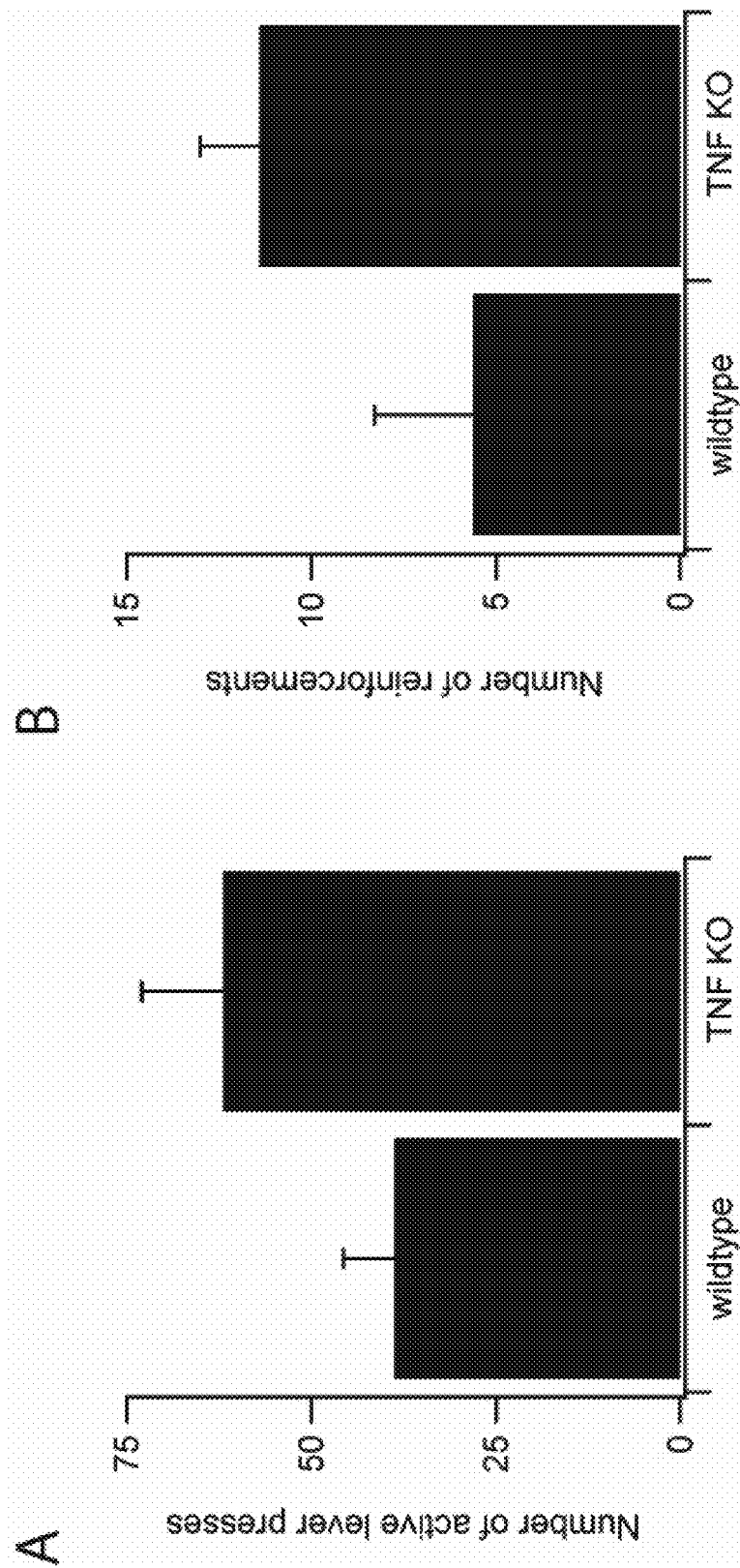
FIG. 4 is a series of graphs demonstrating self-administration of cocaine is regulated by TNFα as measured by the number of active level presses (FIG. 4A) and the number of reinforcements (FIG. 4B).

Self-administration of cocaine is also regulated by TNFα (FIG. 4). Accordingly, a mouse model of self-administration is used and mice are tested in the presence or absence of MPLA injection. A model of conditioned place preference is also tested. The self-administration model will measure the motivation to take cocaine (lever-pressing to receive a dose of drug), and the reinstatement of drug-taking in animals that have stopped (a model for relapse). CPP measures the associations formed between cocaine and a location.

Example 3

The striatum is a major constituent of the basal ganglia, and is a key structure for both motor output and reward processing[1]. Altered striatel functioning is thought to contribute to dysfunctions of the reward pathway, including addiction[2].

Striatel Function and Plasticity

The striatum consists of the putamen and caudate, and serves as the information processing hub of the basal ganglia, integrating sensorimotor, cognitive, and motivation-related information. The GABAergic medium spiny neurons (MSNs) comprise >90% of neurons and are the sole output of the striatum[3].

MSNs integrate glutamatergic input from cortex and thalamus, dopaminergic input from the substantia nigra and ventral tegmentum area, as well as GABAergic input from the external pallidum. MSNs are broadly classified as direct pathway neurons (projecting to the internal globus pallidus, and primarily expressing D1 receptors) or indirect pathway neurons (projecting to the external globus pallidus, and primarily expressing D2 receptors). Direct pathway neurons are important for the initiation of voluntary movements, while indirect pathway neurons help suppress undesired movement. The striatum can be loosely divided into a dorsal motor region and a ventral reward pathway area (often called the nucleus accumbens, subdivided into a core and shell region). Both regions receive extensive dopaminergic innervation: the dorsal striatum primarily from the substantia nigra and the ventral striatum primarily from the ventral tegmentum area (VTA). The glutamatergic synapses to MSNs are known to be quite plastic and are altered in movement disorders[1] and during chronic exposure to drugs of abuse[2].

Changes in corticostriatal synapses contribute to extrapyramidal movement disorders[4,5], a class of basal ganglia dyfunctions ranging from the inability to initiate movements to the inability to prevent movement. Corticostriatal synapses are also modified by drugs of abuse, and directly control some drug induced behaviours[6].

Inflammation is part of the observed response to drugs of abuse, but its role in addiction is not understood. The chronic administration of cocaine leads to changes in glutamatergic synaptic strength in the striatum, which correlate with changes in the behavioural response to cocaine. A model of addiction using the chronic administration of cocaine, known to induce synaptic changes in striatel reward circuits was employed. The contribution of TNF signaling to these drug-induced changes was assessed. Data suggest that TNF has an adaptive role in the response to chronic cocaine.

The response to TNFα appears to be fundamentally different in the major cell type in the striatum, a critical structure for reward and motor output. Here, the basic response to TNFα is inverted: acute TNFα treatment results in AMPAR endocytosis, not exocytosis[24]. The mechanism for TNFα-mediated AMPAR endocytosis was investigated, which is likely due to DARPP-32 dependent activation of PP1, resulting in AMPAR dephosphorylation and endocytosis. Further, using an in vivo manipulation of striatal function, it has been demonstrated that despite having an inverted effect on receptor trafficking TNFα is still normalizing circuit function for the motor pathway.

MSNs in the striatum are GABAergic and respond to TNFα quite differently from pyramidal cells in the cortex or hippocampus. Instead, MSNs respond in a manner similar to the response of GABAergic hippocampal interneurons[7]. Exogenous TNFα application results in the endocytosis of AMPA receptors and a decrease in excitatory synaptic strength (as measured by AMPA/NMDA current ratios and mEPSC amplitudes;). There also is a preferential removal of calcium-permeable AMPA receptors, as judged by a decrease in AMPA rectification. Conversely, blocking TNFα signaling in acute striatal slices results in an increase synaptic strength and an increase in calcium-permeable AMPARs. This suggests that there is on-going TNFα signaling in the striatum, and the results show that the average excitatory synaptic strength in striatel cells from TNFα knockout animals is higher than in wildtype animals. These data indicate that TNFα is an endogenous regulator of glutamatergic synaptic function in the striatum, and that TNFα signaling at synapses will impact the development or expression of striatal dysfunctions.

Mechanisms that suppress drug-induced increases in synaptic strength could potentially diminish the symptoms of addiction. TNFα may play such a role in addiction, with the homeostatic response reducing the rewarding effects of drugs of abuse. The results described suggest TNFα deficient mice display a greater behavioural response to cocaine.

Experiments

Behavioural sensitization is a common readout for effects of the chronic exposure to drugs[6,8,18,19]. It is a gradual increase in behavioral response to repeated exposure to drugs of abuse, and most often assessed as the increase in locomotor response to drug administration[20]. This behavioural paradigm in mice deficient in TNFα signaling was examined.

Animals: Wildtype and TNFα −/− mice, or wildtype mice were compared to littermates treated with DN-TNF[21], which is effective in vivo. DN-TNF is an engineered version of the TNFα protein that intercalates into native TNFα trimers but cannot bind TNFα receptors. DN-TNF was be administered (15 mg/kg IP every 2 days) in three regimens: a) throughout the experiment (to block all TNFα signaling), b) only during conditioning (to block TNFα signaling during learning and behavioural acquisition), or c) only during withdrawal phase (to test the role of TNFα to the expression of the behaviours). The mice are on the C57Bl6/J background, and male mice, 2-4 months of age (matched with controls for each experiment) were used.

Experimental Strategy

The response of mice to repeated doses of cocaine was compared. After habituating animals to handling, the animals receive an IP injection and have their locomotor activity monitored in open-field chambers using Ethovision software for 15 min. After two days of saline injections, mice received five daily injections of cocaine (15 mg/kg) and assayed for locomotion. Following 7-10 days without injections (withdrawal), mice receive a challenge dose of cocaine (also 15 mg/kg) and locomotor activity again assessed (see Examples 1 and 2). A minimum of three separate cohorts have been run.

Data:

Administration of cocaine following this protocol increases TNFα mRNA in the ventral striatum (FIG. 5D), consistent with a role for TNFα in behavioural sensitization. The TNFα −/− mice display increased locomotor sensitization following this protocol, compared to wildtype mice (FIG. 5I).

Preliminary analysis suggests that this is due to both an increased locomotor response to cocaine (evident on the first day of administration) and an increased level of sensitization. Further, experiments using DN-TNF to acutely block TNFα signaling in various phases of the protocol suggest that TNFα is required during the training itself, and not during the withdrawal phase (FIG. 5I). Here there is no increase in sensitivity to cocaine, as the first day response is identical comparing DN-TNF treated and untreated mice. This implies that the increased sensitivity observed in the TNFα −/− mice is not due to an acute loss of TNFα signaling and is unrelated to the increase in behavioural sensitization.

Example 4

Similar experiments as described in Example 1 where MPLA is administered with longer delays before the test dose of cocaine. For example, the test dose of cocaine will be administered at days 2, 4 or 7.

Example 5

Repeated administration of cocaine results in the development of behavioral sensitization, accompanied by a decrease in excitatory synaptic strength in the nucleus accumbens (NAc) through an unknown mechanism. Furthermore, glial cells in the NAc are activated by drugs of abuse, but the contribution of glia to the development of addictive behaviors is unknown. Tumor necrosis factor alpha (TNFα), a cytokine released by activated glia, can drive the internalization of synaptic AMPA receptors on striatel medium spiny neurons. Here it is shown that repeated administration of cocaine activates striatal microglia and induces TNFα production, which in turn depresses glutamatergic synaptic strength in the NAc core and limits the development of behavioral sensitization. Critically, following a period of abstinence, a weak TLR4 agonist can re-activate microglia, increase TNFα production, depress striatel synaptic strength and suppress cocaine-induced sensitization, without inducing sickness behaviour. Thus, cytokine signaling from microglia can regulate both the induction and expression of drug-induced behaviours.

Activation of Striatel Microglia by Cocaine

Substance abuse is a serious societal problem with a large economic burden, poor treatment options, and high relapse rate. Changes in striatal processing, particularly in the NAc, are thought to be necessary for the maintenance of addictive behaviours, and repeated exposure to drugs of abuse leads to predictable changes in synaptic strength in the NAc (Luscher and Malenka, 2011). Cocaine elevates dopamine levels and acute treatment of striatal neurons with D1 dopamine receptor agonists or with cocaine increases the phosphorylation and insertion of AMPA receptors (Chao et al., 2002; Mangiavacchi and Wolf, 2004; Snyder et al., 2000).

However, repeated cocaine treatment in vivo (five days of non-contingent administration) results in an initial decrease in the AMPA/NMDA ratio on striatal medium spiny neurons (MSNs), as measured 24 hours after the last cocaine injection (Kourrich et al., 2007; Mameli et al., 2009). A period of abstinence or extended cocaine treatment results in the gradual elevation of AMPA/NMDA ratios and AMPAR surface expression (Boudreau and Wolf, 2005; Dobi et al., 2011; Schumann and Yaka, 2009), although a challenge dose of cocaine will again result in lowered ratios and receptor content (Boudreau et al., 2007; Kourrich et al., 2007; Thomas et al., 2001). Self-administration of cocaine also causes similar changes, with cocaine exposure causing a loss of AMPA receptors and depressing synaptic strength and extended abstinence resulting in synaptic strengthening and an accumulation of AMPA receptors (Conrad et al., 2008; Ghasemzadeh et al., 2009; Lu et al., 2003; Ortinski et al., 2012; Schramm-Sapyta et al., 2006). This bidirectional plasticity suggests other factors, in addition to dopamine, contribute to the synaptic changes induced by the chronic drug exposure.

Recently, it has been shown that, unlike pyramidal cells (Beattie et al., 2002), the inflammatory cytokine TNFα drives internalization of AMPARs on MSNs, reduces corticostriatal synaptic strength, and reduces the aberrant changes in striatel circuit function induced by the chronic blockade of D2 dopamine receptors (Lewitus et al., 2014). Further, glia are the main source of TNFα in the brain. Both microglia (Thomas et al., 2004) and astrocytes (Bowers and Kalives, 2003) are activated by psychostimulants and have been suggested to regulate drug-induced behaviour (Hutchinson and Watkins, 2014; Miguel-Hidalgo, 2009). Therefore, it is hypothesized that glia, through the release of TNFα, have a mitigating function on the circuit changes induced by chronic cocaine. Here it is demonstrated that striatel microglia are activated by cocaine, and mitigate the synaptic and behavioural changes induced by the repeated administration of cocaine.

Results

To determine the effect of in vivo cocaine exposure on TNFα levels in the ventral striatum, TNFα mRNA and protein levels were measured in mice given intraperitoneal injections of saline or cocaine. A single injection of cocaine had no effect on TNFα levels (measured 24 hours post-injection), but 5 days of daily cocaine treatment (measured 24 hours after the final injection) significantly increased both TNFα mRNA and protein, as measured by immunocytochemical staining intensity (FIG. 5A-D). TNFα returned to basal levels following 10 days of abstinence from cocaine. To understand the impact of TNFα on synaptic function in the NAc, AMPA/NMDA ratios were measured at glutamatergic synapses on MSNs in the NAc core. Alteration in NAc core AMPA receptors are involved in the expression of behavioral sensitization to psychostimulants (Kalives, 2009).

It has been previously shown that TNFα drives internalization of AMPARs on MSNs in the dorsal striatum (Lewitus et al., 2014). As repeated cocaine administration primarily affects direct-pathway MSNs, specific subpopulations of MSNs in the NAc core were tested for their response to TNFα. Acute NAc slices were incubated with TNFα (10 ng/ml or 100 ng/ml) and whole-cell recording were made for Drd1a-td Tomato (D1) positive and negative (D2) MSNs. Consistent with previous reports (Cepeda et al., 2008), D1-MSNs have significantly higher initial AMPA/NMDA ratios than D2-MSNs. A low dose of TNFα (10 ng/ml) had no significant effect on either cell type. However, 100 ng/ml TNFα significantly reduced the AMPA/NMDA ratio on D1-MSNs, with a non-significant reduction in the AMPA/NMDA ratio on D2-MSNs (FIG. 5E). These results suggest that D1-MSNs are more sensitive to TNFα than D2-MSNs, although D2-MSNs likely respond to a lesser degree.

Figure 9:
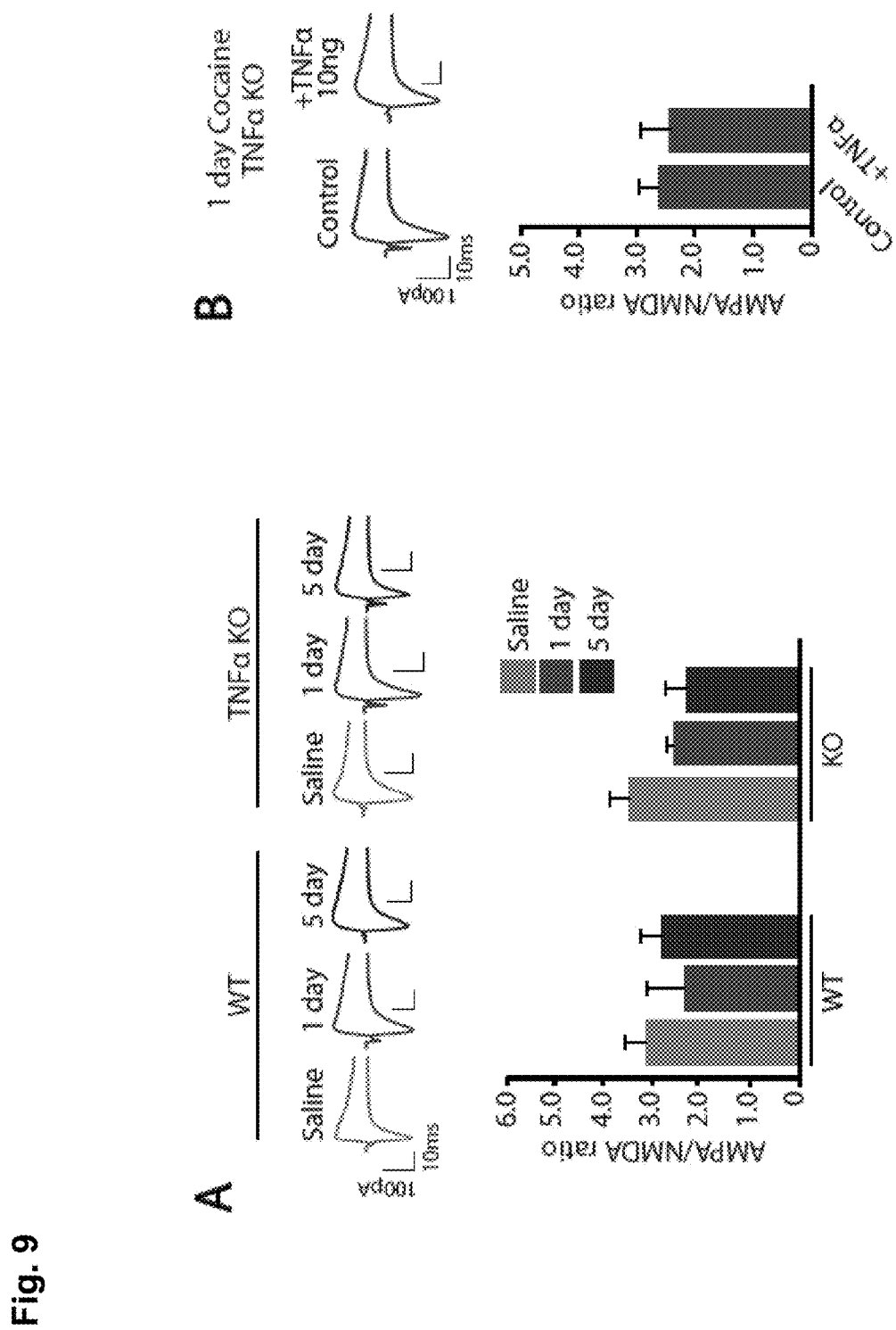
FIG. 9A is a series of graphs and traces showing that AMPA/NMDA ratios on D2-MSNs are not altered by cocaine treatment. Representative traces and mean AMPA/NMDA ratios from presumptive D2-MSNs in the NAc core. Consistent with previous reports (Cepeda et al., 2008), D2-MSNs have significantly lower basal AMPA/NMDA ratios than D1-MSNs. Treatment with 1 day or 5 days of cocaine (15 mg/kg) had no effect on AMPA/NMDA ratios in either WT or TNFα-KO mice (data from the same animals used in FIG. 1F; One way ANOVA: $F_{(5,51)}$=1.08, p=0.38; WT: D2$_{(saline)}$; n=8 cell (from 5 mice); D2 (1 day cocaine): n=6 (3); D2$_{(5\ days\ cocaine)}$: n=8 (3); TNFα-/-: D2$_{(saline)}$: n=11 (4); D2$_{(1\ day\ cocaine)}$: n=14 (6); D2$_{(5\ days\ cocaine)}$: n=10 (3)).
FIG. 9B is a series of graphs and traces showing that D2-MSNs from TNFα-KO mice are not more sensitive to TNFα after a single cocaine injection. Animals were injected with cocaine 24 hours prior to slicing, and incubated ex-vivo with 10 ng/ml TNFα (the same animals from FIG. 5G). Treatment with TNFα had no effect on AMPA/NMDA ratios in D2-MSNs (D2$_{(24\ hour\ cocaine)}$: n=14 (6 mice); D2 $_{(24\ hour\ cocaine\ with\ TNF\alpha)}$: n=7 (4); Student's t-test, $t_{(19)}$=0.32, p=0.75).

Repeated non-contingent administration of cocaine results in lower AMPA/NMDA ratios of excitatory inputs onto the NAc specifically on the D1-MSN subtype (Kim et al., 2011; Pascoli et al., 2012). To test whether the decrease in AMPA/NMDA ratios after repeated drug administration is due to the increase in TNFα expression, the AMPA/NMDA ratio was evaluated on D1 and D2 MSNs in the NAc core following cocaine or saline administration in WT and TNFα$^{-/-}$ mice. As expected for WT mice, a single injection of cocaine did not significantly reduce AMPA/NMDA ratios on D1-MSNs, but 5 daily cocaine injections did (FIG. 5F). Strikingly, in TNFα$^{-/-}$ mice, a single injection of cocaine was enough to significantly increase AMPA/NMDA ratios, which remained elevated after 5 days of cocaine administration. No significant differences were observed in D2-MSNs for either genotype (FIG. 9A). These results suggest that the reduction in AMPA/NMDA ratios observed in D1-MSNs after repeated cocaine administration is due to the increase in TNFα levels in the NAc, and that cocaine itself is acting to increase synaptic strength. This is consistent with the exocytosis of AMPARs observed with direct stimulation of D1Rs on MSNs (Mangiavacchi and Wolf, 2004). Moreover, this result suggests that during cocaine treatment D1-MSNs are more responsive to the lower endogenous level of TNFα, perhaps because newly inserted AMPARs are more labile, as has been seen at potentiated synapses in the amygdala (Clem and Huganir, 2010). To test the hypothesis that potentiated D1-MSNs are more sensitive to TNFα, TNFα mice were treated with a single injection of cocaine and the effect of a low level of TNFα (10 ng/ml) on AMPA/NMDA ratios was evaluated. Although this level of TNFα had no significant effect on MSNs from wildtype untreated animals (FIG. 5E), it significantly reduced AMPA/NMDA ratios on D1-MSNs from cocaine treated knockout animals (FIG. 5G). This treatment had no effect on D2-MSNs (FIG. 9B). To test whether cocaine-induced TNFα signaling would occlude further TNFα synaptic depression, wildtype animals were treated with cocaine for 5 days, and then treated striatel slices ex-vivo with TNFα (100 ng/ml). The AMPA/NMDA ratio on D1-MSNs (already reduced compared to saline treated animals; FIG. 5E) was not further reduced by treatment with TNFα (FIG. 5G). This suggests that the synaptic depression induced by repeated cocaine injections occludes the TNFα-mediated reduction in AMPA/NMDA ratio. Overall, these data suggest that repeated cocaine treatment is elevating TNFα, which suppresses the synaptic changes being induced by cocaine in the NAc core.

Depressing synaptic strength in the NAc can reduce the behavioral sensitization to cocaine (Pascoli et al., 2012). Given that TNFα is elevated in the NAc by repeated cocaine treatment and can depress glutamatergic synaptic strength, behavioral sensitization in TNFα$^{-/-}$ mice was evaluated. Behavioural sensitization is a simple model of drug-induced behavioural change, which measures the progressive increase in locomotor response to psychostimulants such as cocaine (Robinson and Berridge, 2001). TNFα$^{-/-}$ mice displayed an increased initial locomotor response to cocaine, compared to wildtype mice (FIG. 5H) as well as increased sensitization. This is similar to what has been observed with methamphetamine sensitization in TNFα$^{-/-}$ mice (Nakajima et al., 2004). To exclude compensatory mechanisms resulting from the absence of TNFα during development, the soluble form of TNFα in wildtype mice was pharmacologically blocked using XENP1595 (an engineered dominant negative variant of TNFα (DN-TNF) that rapidly binds with soluble TNFα to form heterotrimers that neither bind to nor stimulate signaling through TNF receptors (Steed et al., 2003). Wildtype mice were administered DN-TNF either during the 5 days of conditioning (to block TNFα signaling during acquisition) or during the abstinence period starting immediately after the last cocaine injection (to test the role of TNFα in the expression of the behaviours). Blocking TNFα signaling only during acquisition was sufficient to increase the amount of sensitization as well as maintain the elevated response on the challenge day, while blocking TNFα signaling during the 10 day period of abstinence had no effect on the response to the challenge dose (FIG. 5I). These results suggest that TNFα is active during acquisition but not during drug abstinence, which is consistent with the increased TNFα expression during this period (FIG. 5C,D). Furthermore, the increased sensitivity observed in the TNFα$^{-/-}$ mice in the first day of cocaine is not due to an acute loss of TNFα signaling and is likely unrelated to the increase in behavioural sensitization.

Activation of Microglia by Cocaine and Release of TNFα

Figure 6:
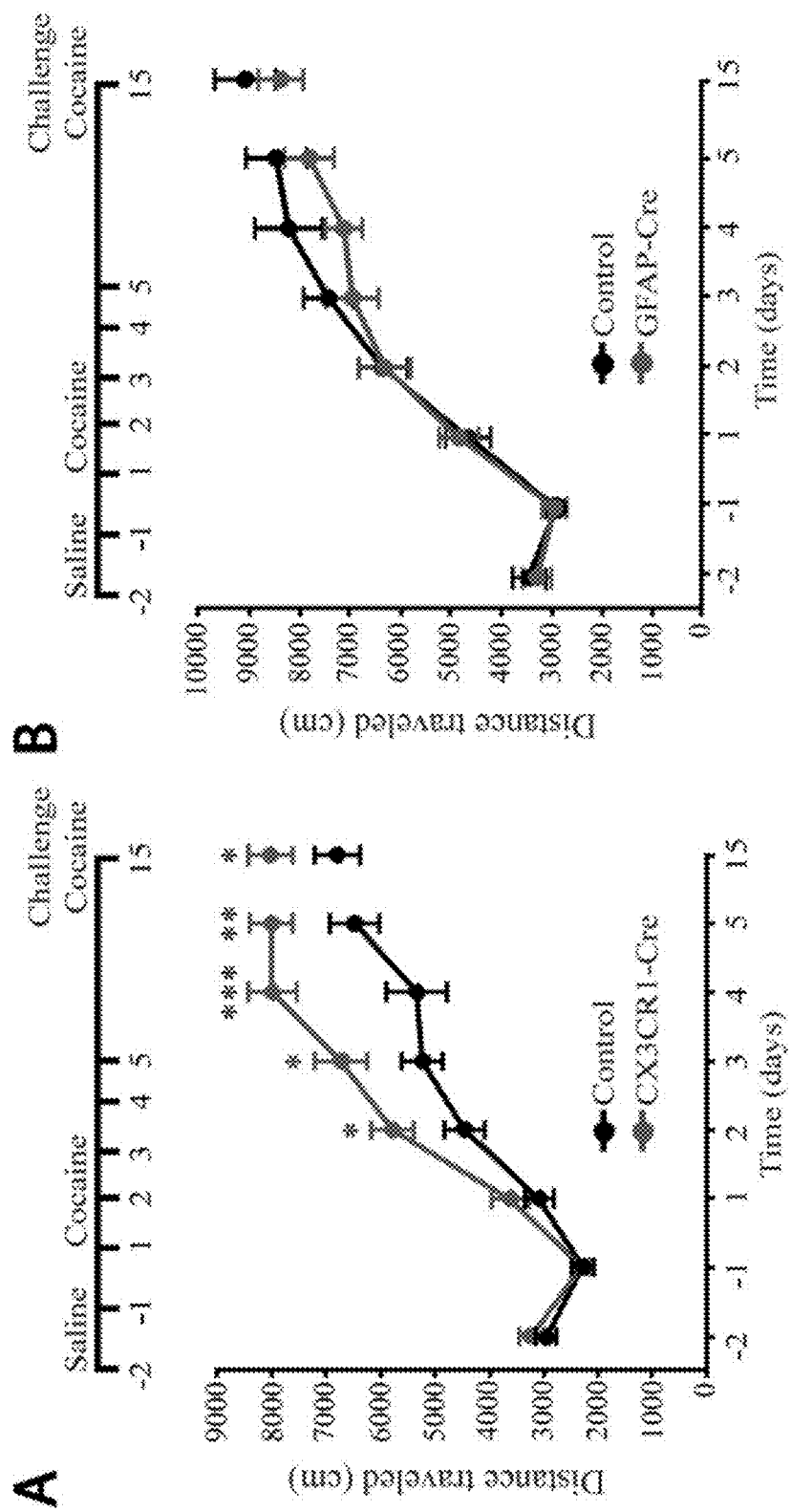
FIG. 6 is a series of charts, graphs and images showing that microglia are activated by cocaine and release TNFα to antagonize cocaine-induced behavioral sensitization.
Figure 6:
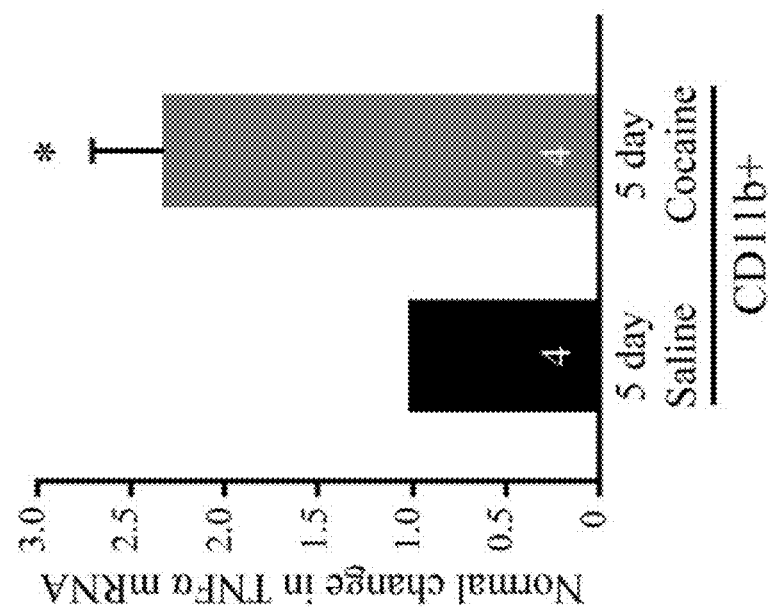
Figure 6:
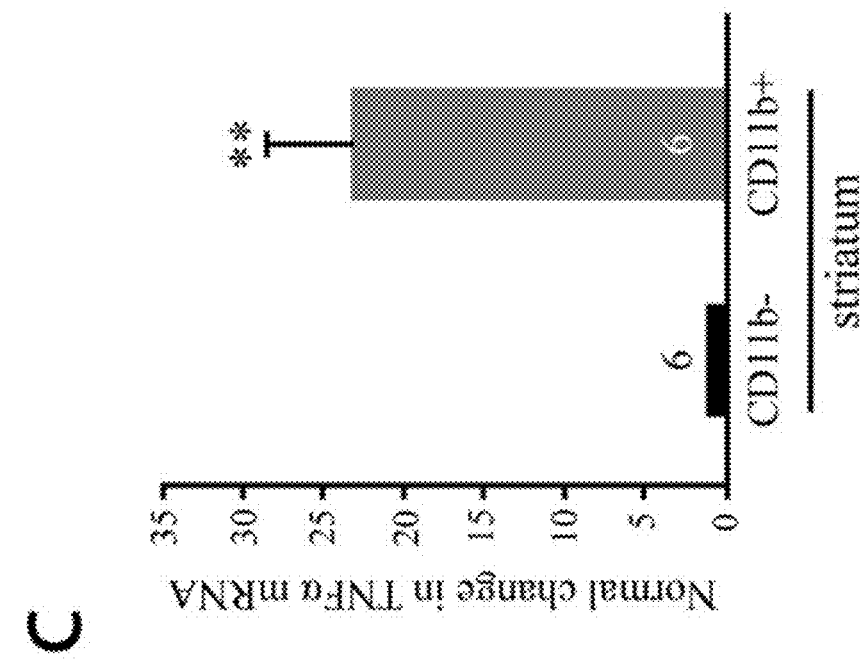
Figure 6:
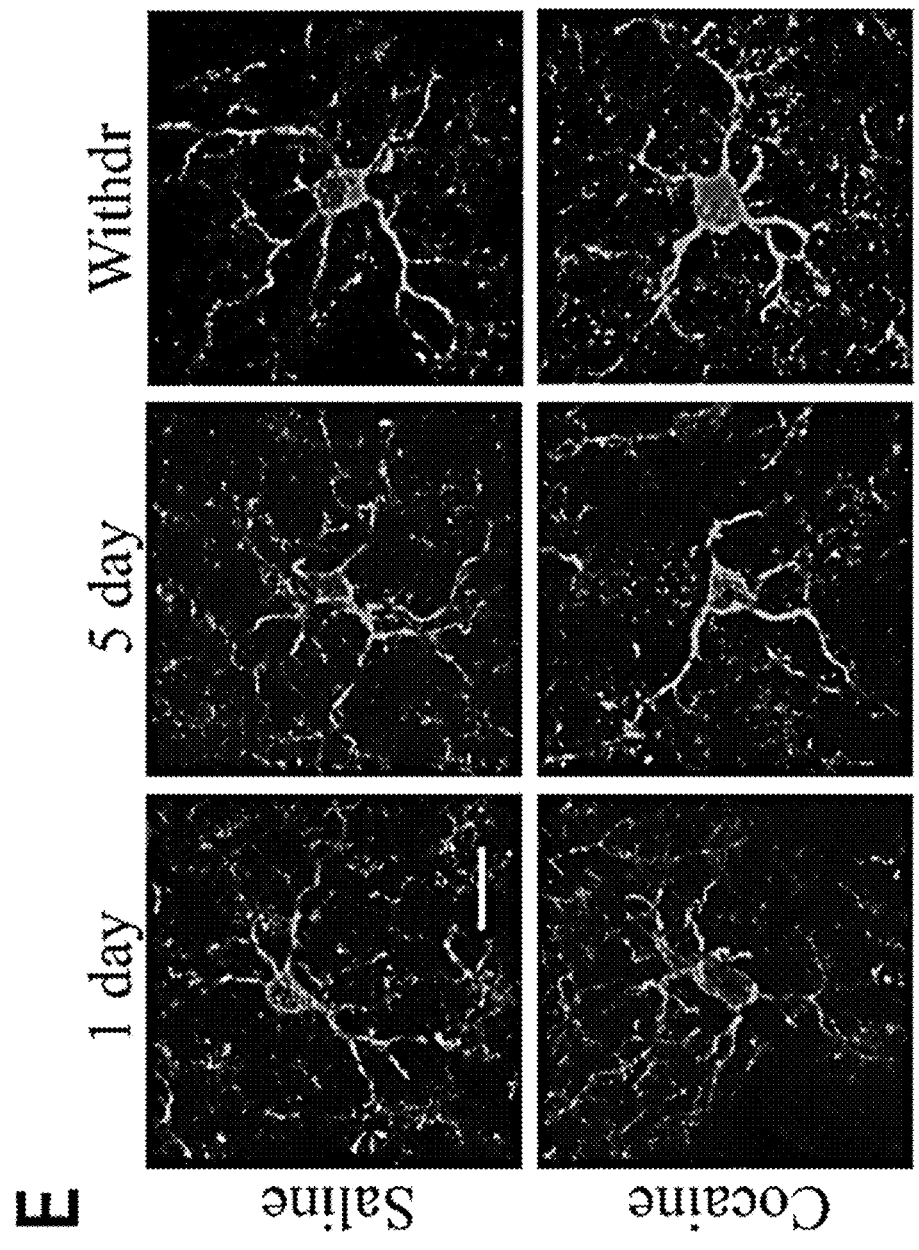
Figure 6:
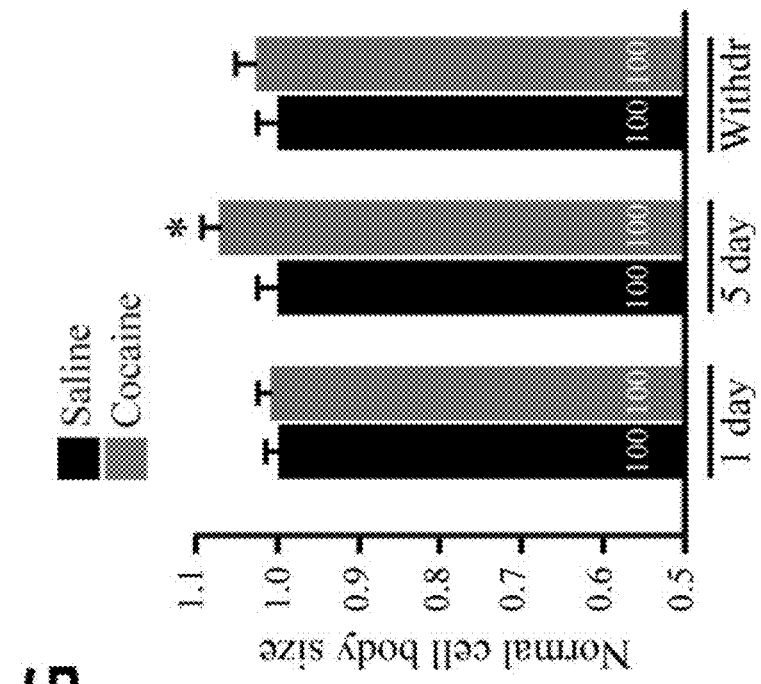
Figure 6:
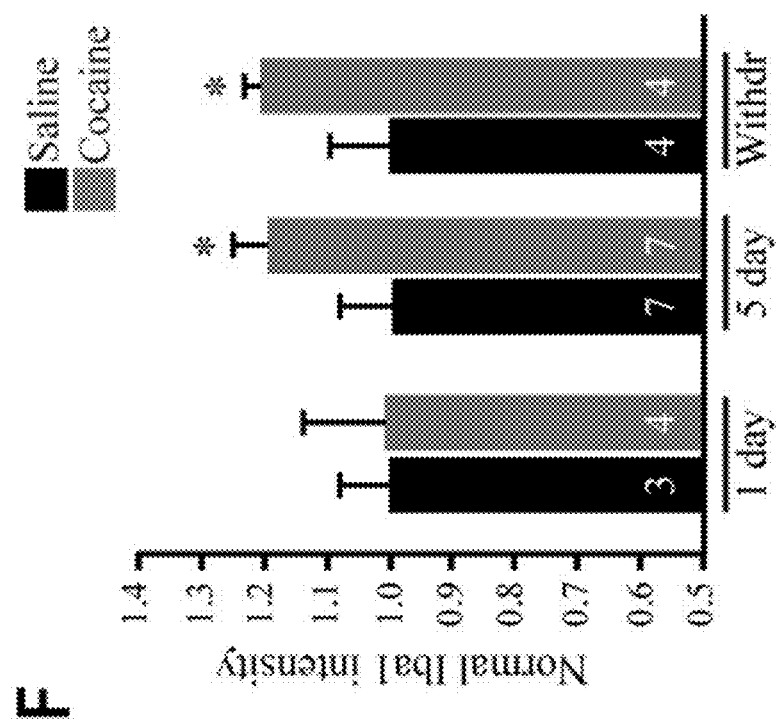
Figure 6:
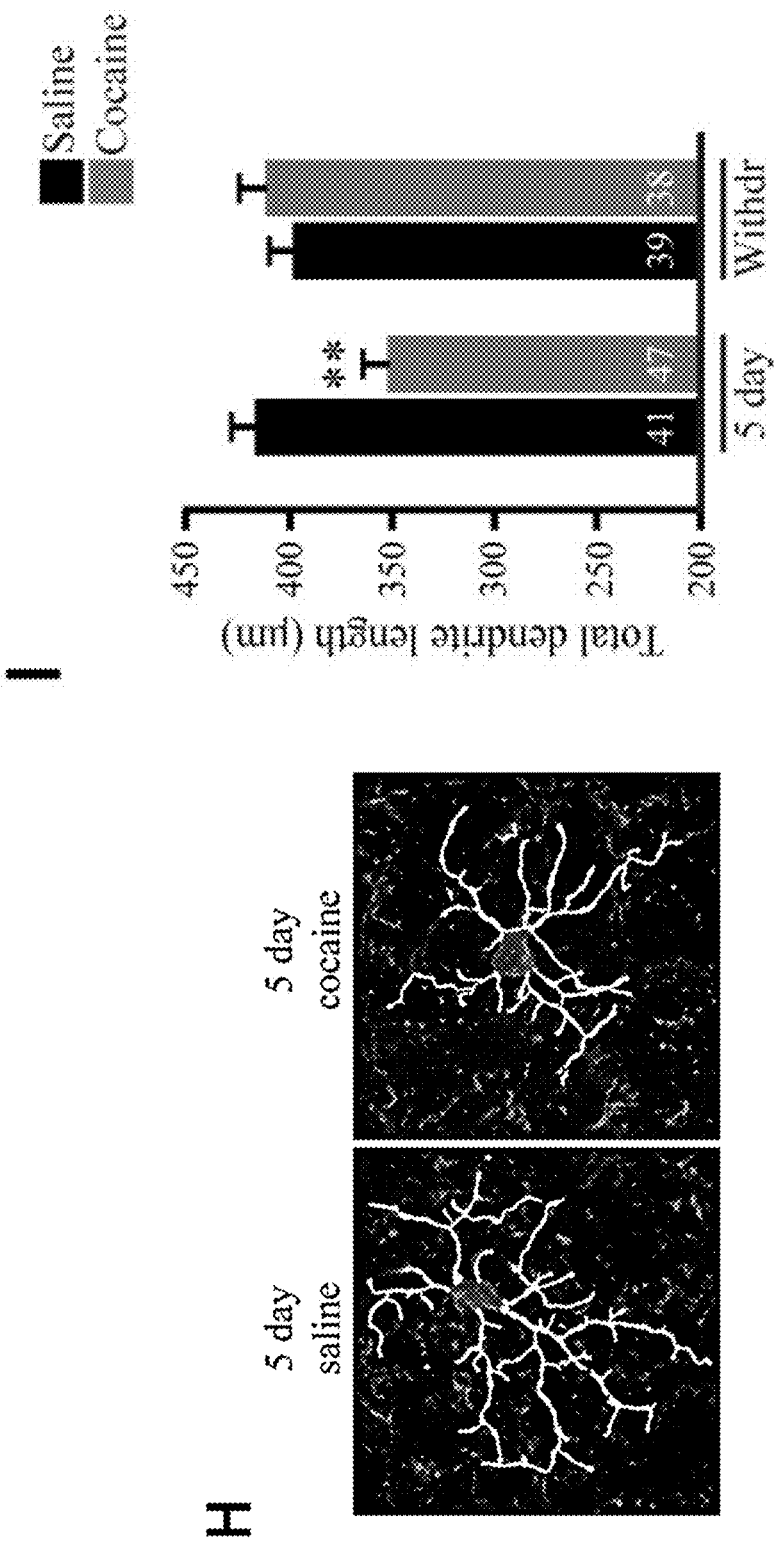
Figure 10:
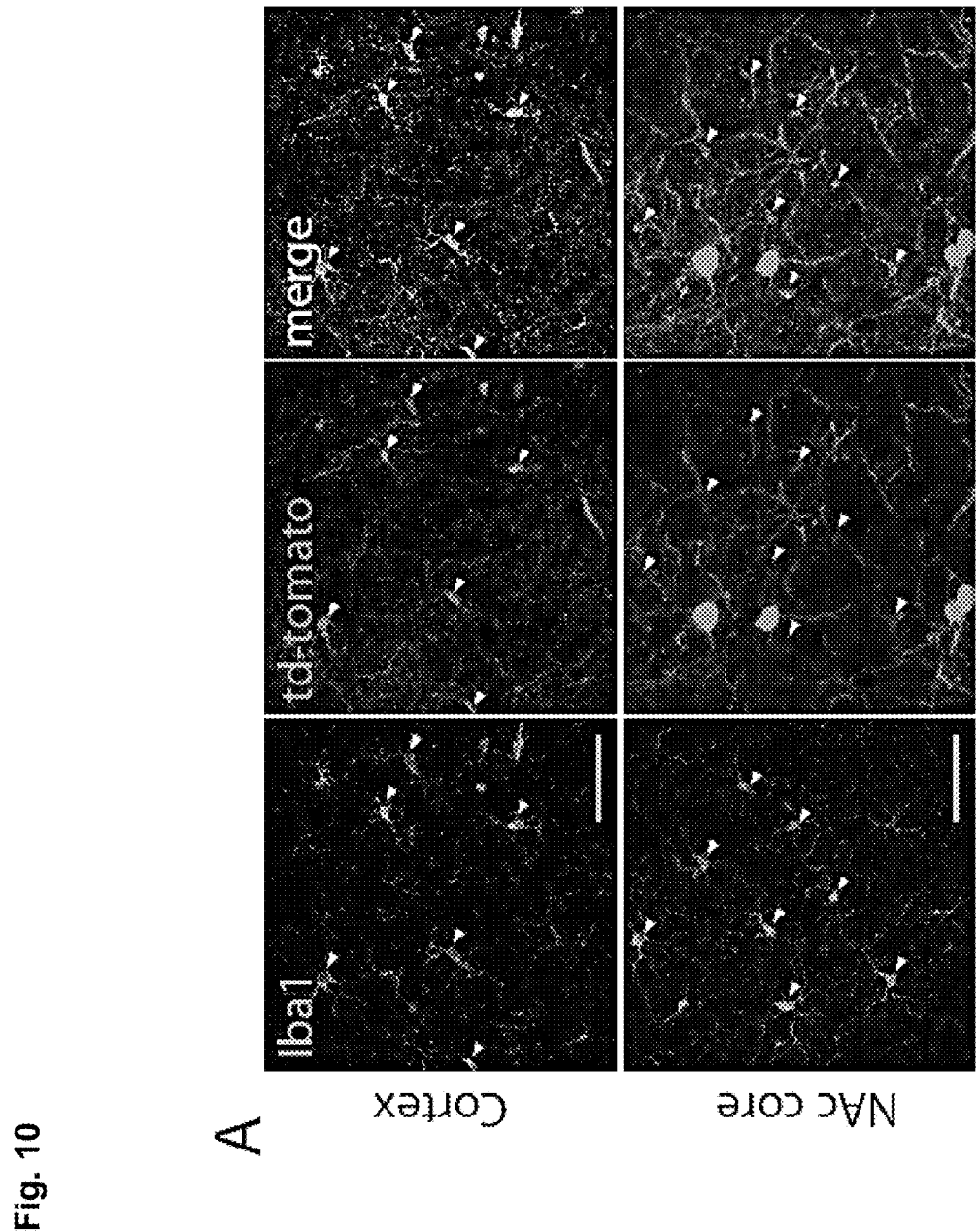
FIG. 10A is a series of images showing that CX3CR1-Cre is preferentially expressed in microglia. Confocal projection images from CX3CR1-Cre×Rosa26-STOP-tdtomato mice immunostained for microglia marker Iba1 (scale bar=40 µm). Cells expressing CX3CR1-Cre-recombinase, which removes the floxed STOP codon allowing for expression of td-tomato, are red. While no fluorescence was observed in Cre negative animals, expression of td-tomato was observed in almost all cells expressing Iba1 (arrowheads). Sections from two Cre positive mice were imaged and while some brain regions (e.g. cortex, top panels) showed almost exclusive expression of td-tomato in Iba1+ microglia, some regions (including the nucleus accumbens, bottom panels) also had expression in a small subset of neurons. This is consistent with the observation that some neurons do express CX3CR1 (Hughes et al., 2002; Meucci et al., 2000). No astrocyte expression of td-tomato was observed.
FIG. 10B is a series of images showing that GFAP-Cre expression in astrocytes and neurons in the striatum. (Top) Confocal projection images from GFAP-Cre×Rosa26-STOP-tdtomato mice immunostained for GFAP. GFAP+ cells reliably express td-tomato in the nucleus accumbens (arrowheads, scale bar=50 µm). However, only low numbers of astrocytes are observed to be GFAP-expressing in the nucleus accumbens, as is typical for grey matter astrocytes. More GFAP+ cells are observed in the white matter of the commissure and also express td-tomato (scale bar=20 µm). (Middle) Representative staining of GFAP and NeuN in GFAP-Cre×Rosa26-STOP-tdtomato mice in the nucleus accumbens (scale bar=30 µm) and dorsal striatum (same scale). Some td-tomato+ cells in the nucleus accumbens are neurons (as neural progenitors typically express GFAP during development). In the nucleus accumbens core, the percent of td-tomato+ cells that are neurons (NeuN+) is approximately 24%. The percent of neurons (NeuN+) that are also td-tomato+ is ~8%. In the dorsal striatum, the percent of td-tomato+ cells that are neurons (NeuN+) is ~47%; the percent of neurons (NeuN+) that also express td-tomato is ~29%. (Bottom) Microglia (labeled with Iba1) never displayed expression of td-tomato. Representative micrographs from the commissure and nucleus accumbens show no overlap between Iba1 staining and td-tomato expression (scale bar=30 µm).
FIG. 10C is a FACS analysis of microglia isolated from adult tissue to assess efficiency of CD11b-positive microglial isolation using magnetic beads. Microglial cells were isolated from striatum and cortex (4-5 animals pooled per n), using CD11b microbeads. Representative flow cytometry plots of CD11b-negative cell fractions (i-iii) and CD11b-positive microglial cell fractions (iv-vi) shows the hierarchical gating strategy (polygons and arrows) to assess microglial cell purity: (i,iv) Pb gates cells on their size (FSC-A; forward scatter area), and granularity (SSC-A; side scatter area); (ii, v) P2 gates live cells (negative for the eFluor780 viability dye; and (iii, vi) P3 gates CD11b-positive cells (i.e. microglia) using CD11b-V450. Note that only CD11b-positive microglial fractions (P3) of >95% were used for qPCR analysis.
FIG. 10D is a bar graph showing that cocaine does not increase TNFα RNA in non-microglial cells. Five daily cocaine treatments actually resulted in a decrease in TNFα mRNA of 3.26±0.21 fold; Wilcoxon rank sum test, p=0.021; n=4 (each n pooled from 5 animals).
FIG. 10E is a bar graph showing that cocaine treatment does not alter the number of microglia in the nucleus accumbens. The number of Iba1-labeled microglia in the nucleus accumbens were counted in each confocal projection image (n=72, 55, 34, 36, 32, 31 images (respectively) from 4 animals) from adult mice 1 day after a single cocaine injection (i.p. 15 mg/kg), after 5 days daily injections, or after 5 injections followed by 10 days of withdrawal. No change in the number of microglia in the NAc was observed at any time point (microglia per image: 1 day saline: 15.5±0.36; 1 day cocaine: 15.7±0.47; 5 days saline: 14.9±0.54; 5 days cocaine: 15.1±0.45; withdrawal saline: 15.5±0.49; withdrawal cocaine: 16.4±0.59; One way ANOVA: F (5,259)=0.986; p>0.43).
FIG. 10F is a series of representative confocal projection images of GFAP immunostaining in the nucleus accumbens from adult mice 1 day after a single cocaine injection (i.p. 15 mg/kg), after 5 days of daily injections, or after 5 injections followed by 10 days of abstinence (scale bar=40 µm).
FIG. 10G is a series of graphs showing that GFAP levels are not altered by cocaine. Quantification of the area and intensity of GFAP immunoreactivity. Values are normalized to the mean saline intensity for each time point (Area: n=24 images from 4 animals (1 day), 24 and 26 images from 4 animals (5 days), and 15 images from 4 animals (withdrawal); Student's t-test: 1 day, p=0.29; 5 days, p=0.14; withdrawal, p=0.77; Intensity: n=22 images from 4 animals (1 day), 29 images from 4 animals (5 days), and 15 images from 4 animals (withdrawal); Student's t-test: 1 day, p=0.37; 5 days, p=0.36; withdrawal, p=0.46).
Figure 10:
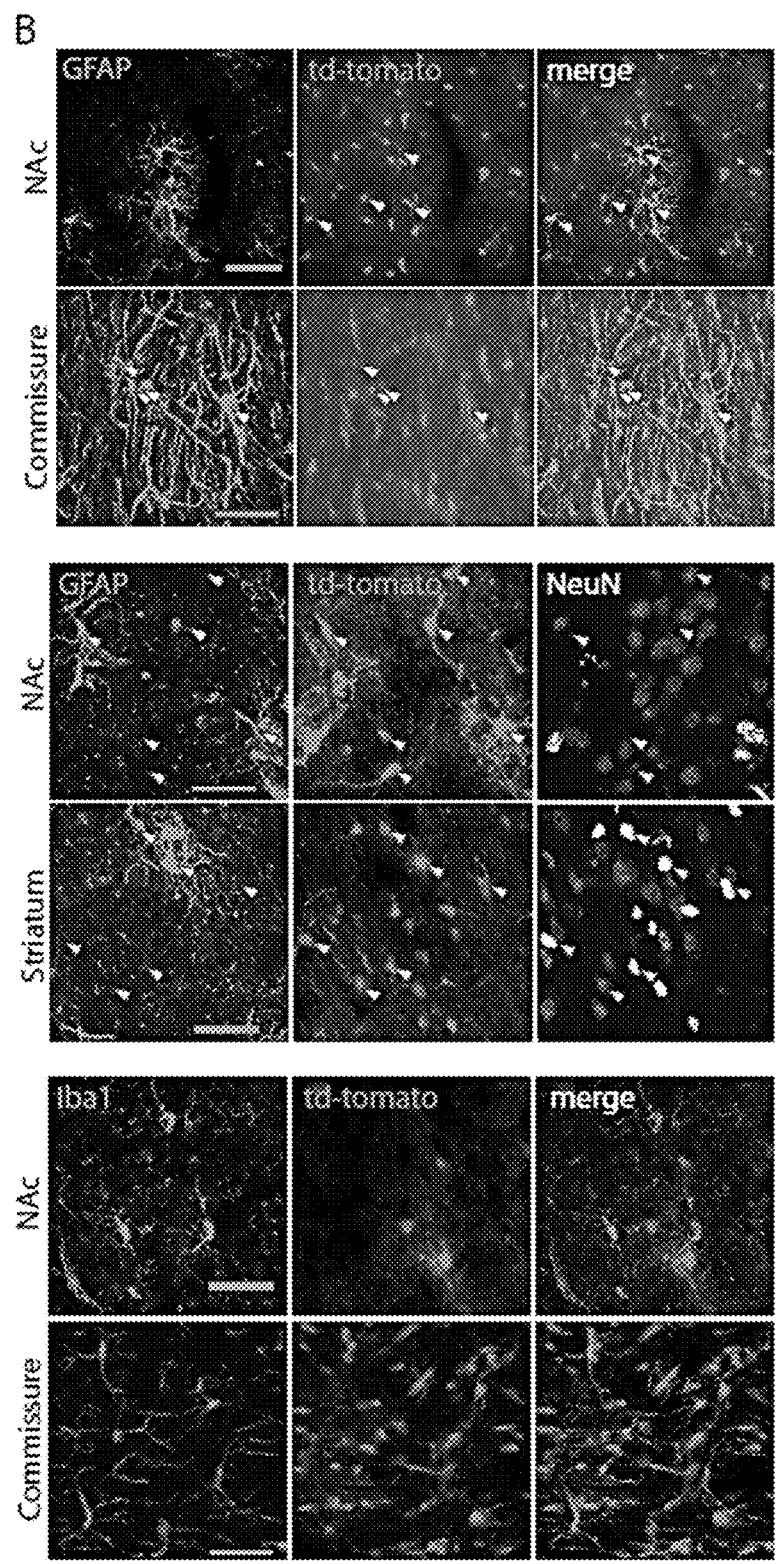
Figure 10:
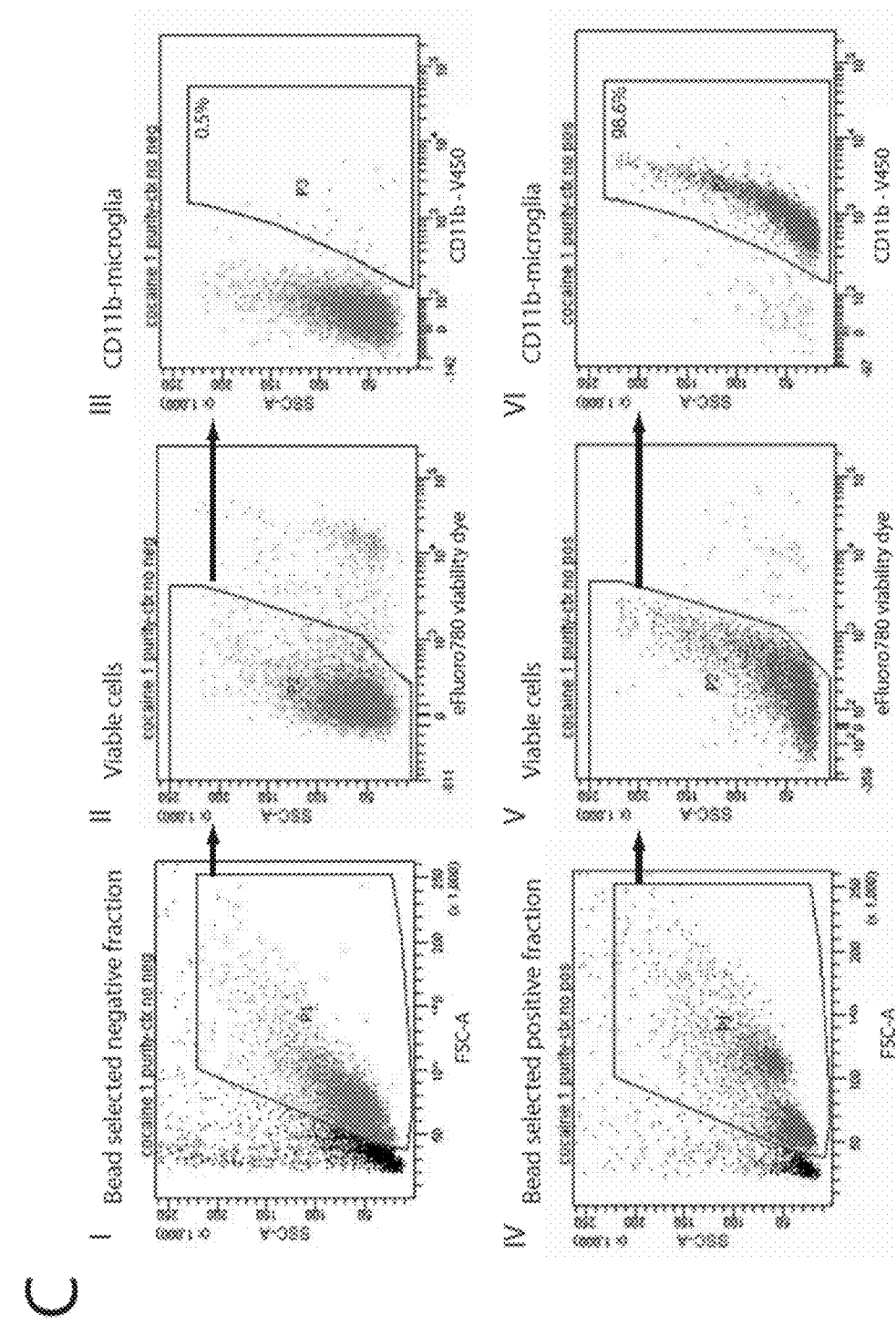
Figure 10:
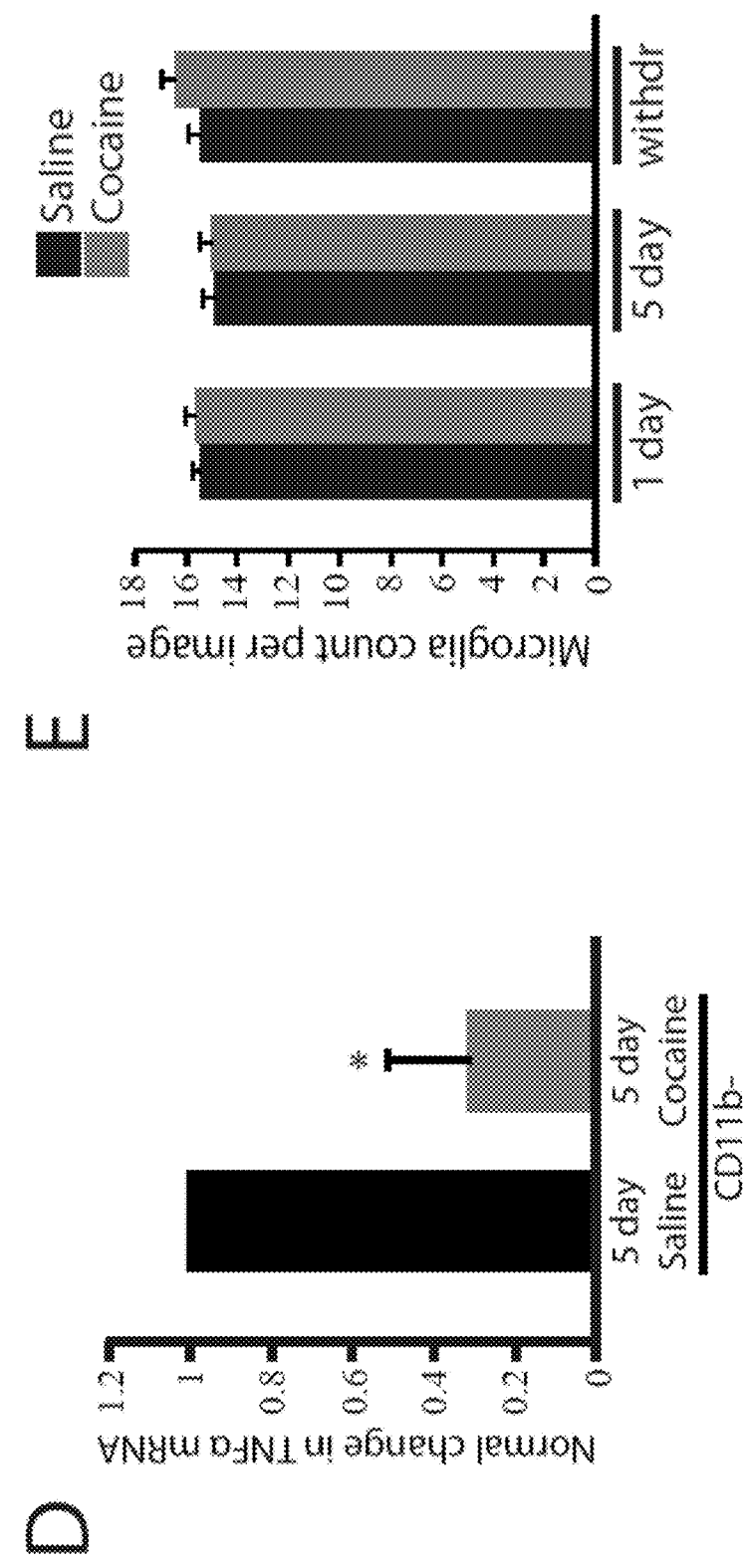
Figure 10:
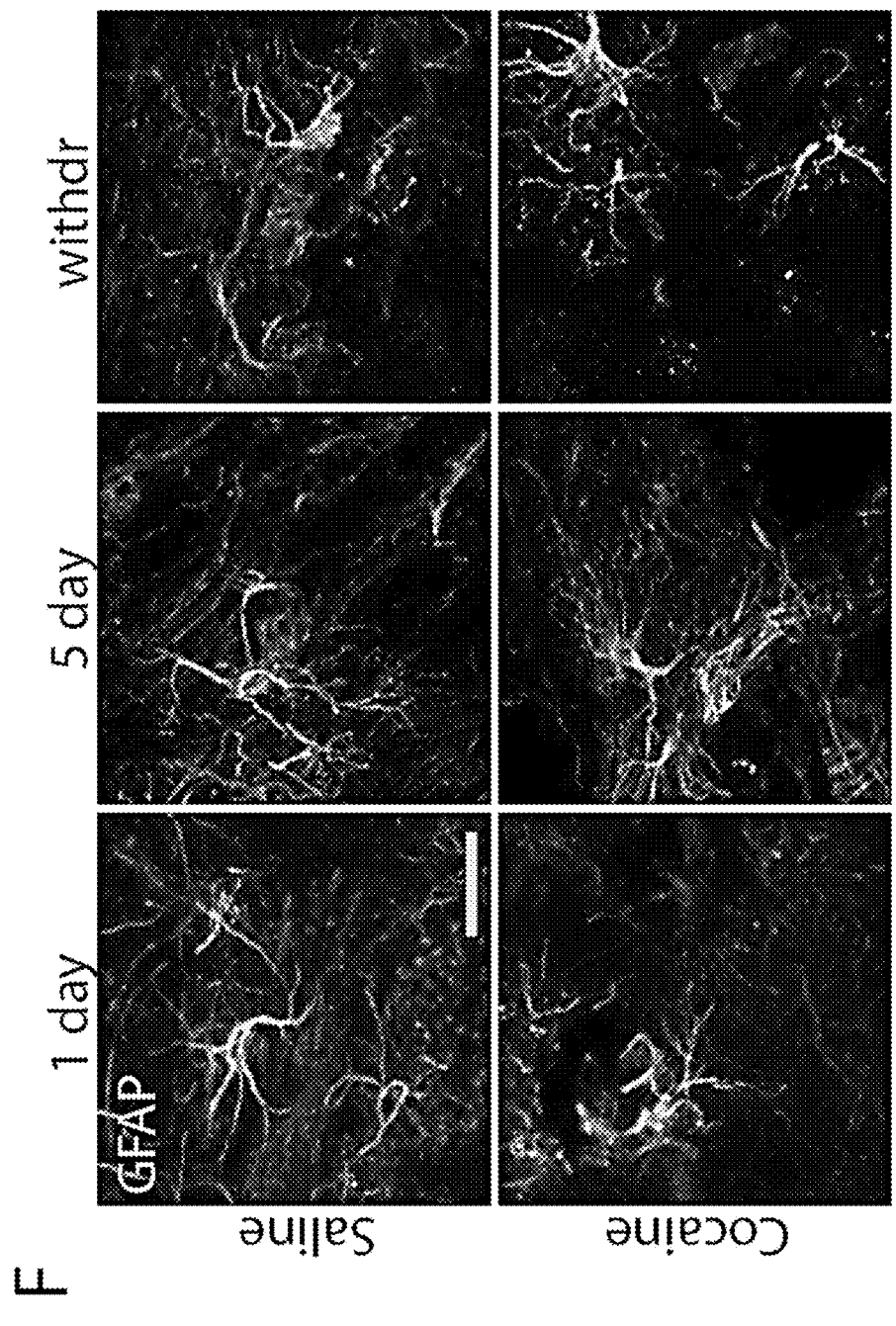
Figure 10:
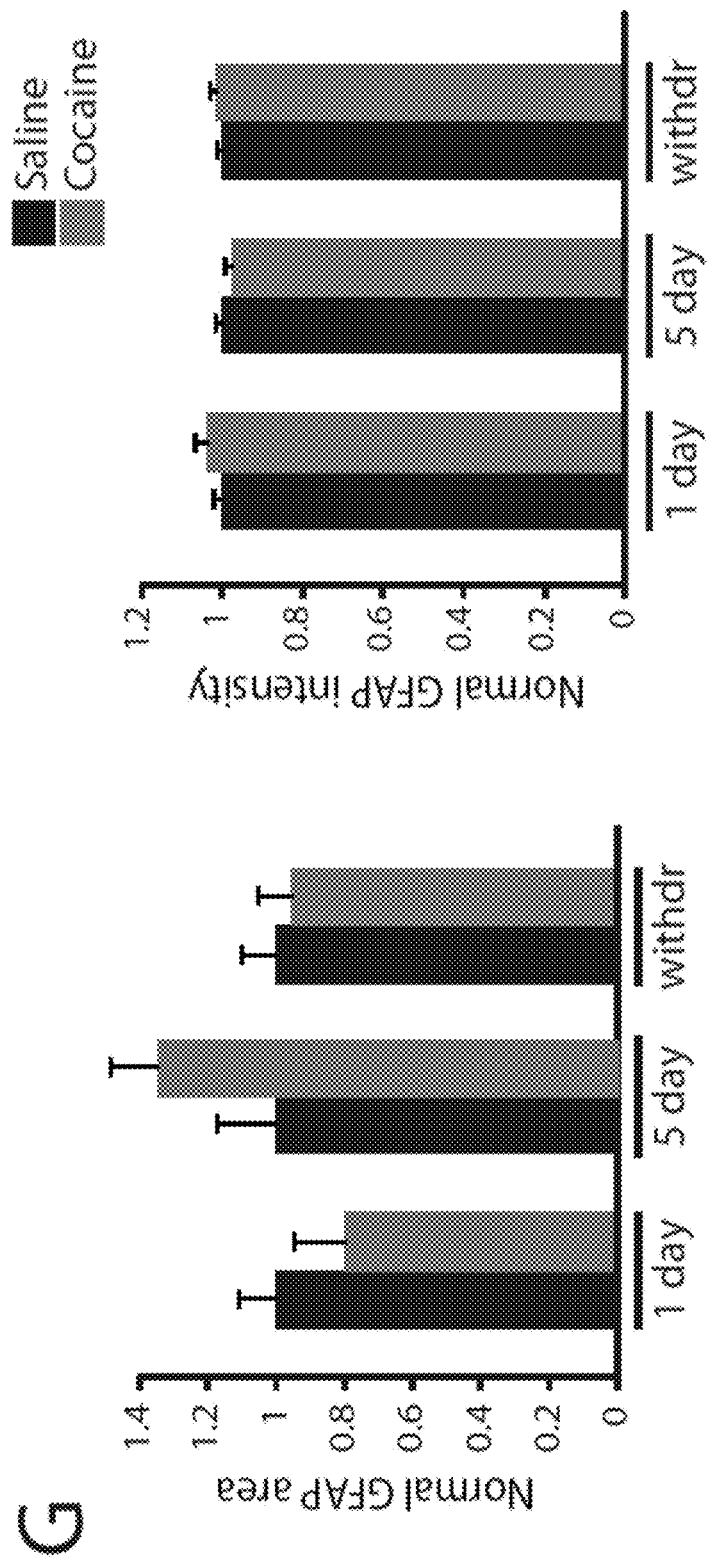

In other brain regions, the TNFα that regulates synaptic function is produced by glia (Beattie et al., 2002; Stellwagen and Malenka, 2006), the principle types of which are astrocytes and microglia. To assess the source of TNFα regulating cocaine-induced behavioral sensitization, a Cre-loxP system was used to selectively delete TNFα from distinct subclasses of glia; CX3CR1-Cre mice for microglia (FIG. 10A) and GFAP-Cre mice for astrocytes (FIG. 10B). Mice that lack microglial TNFα showed a significantly higher level of sensitization to cocaine from the second day of cocaine injection that was maintained through withdrawal (FIG. 6A). Conversely, mice that lack astrocytic TNFα had a slightly lower level of sensitization than control mice, although this was not significant (FIG. 6B). These results suggest that microglia are important to the adaptive TNFα response to repeated cocaine administration. To verify this, microglia were isolated from the striatum of cocaine and saline treated animals by magnetic bead sorting (FIG. 10C; (Butovsky et al., 2014)), and compared TNFα mRNA in the microglial and non-microglial fractions. Firstly, microglia contained the vast majority of TNFα mRNA, showing over a 20-fold enrichment compared with the other striatel cell types (FIG. 6C). Secondly, the TNFα mRNA was increased by cocaine treatment, by almost 2.5 fold, specifically in microglia cells (FIG. 6D) and not the other cell types (where TNFα mRNA actually decreased 3.26±0.21 fold; Wilcoxon rank sum test, p=0.021; n=4).

Resting microglia have a ramified morphology but continuously survey the healthy brain and respond to a variety of activation signals by undergoing progressive morphological and functional changes (Kettenmann et al., 2011). Cocaine administration could activate microglia in the NAc, which could lead to the observed elevation of TNFα. Using the microglia marker Iba1, microglia was labeled in adult mice, 24 hours after a single cocaine injection, 24 hrs after 5 days of daily cocaine injections, or after 10 days of drug abstinence. Although no change was identified in the number of microglia in the NAc at any time point (FIG. 10E), Iba1 intensity was increased in microglia by 5 days of cocaine, and after a period of abstinence (FIG. 6C-D), indicating activation. Further, the microglia cell body area was increased by 5 days of cocaine (FIG. 6E; 5 d saline: 34.7±0.9 μm$^2$; 5 d cocaine: 37.2±0.9 μm$^2$), and more detailed analysis revealed a decrease in process length of microglia (FIG. 6F-G). These changes in microglia morphology are consistent with an activated phenotype, although none of the microglia displayed the amoeboid morphology often observed in highly activated phagocytic microglia. In contrast to the change in microglia, no activation of astrocytes was observed, as judged by GFAP expression. Cocaine did not alter the area or intensity of GFAP immunostaining in the NAc from mice treated with one or five daily injections of cocaine (FIG. 10F-G). This is consistent with the observation that TNFα is derived from microglia and not astrocytes during sensitization. These data strongly suggest that microglia produce the cocaine-induced upregulation of TNFα production in the striatum seen during sensitization.

D2 Agonism Increases Microglial TNFα

Figure 7:
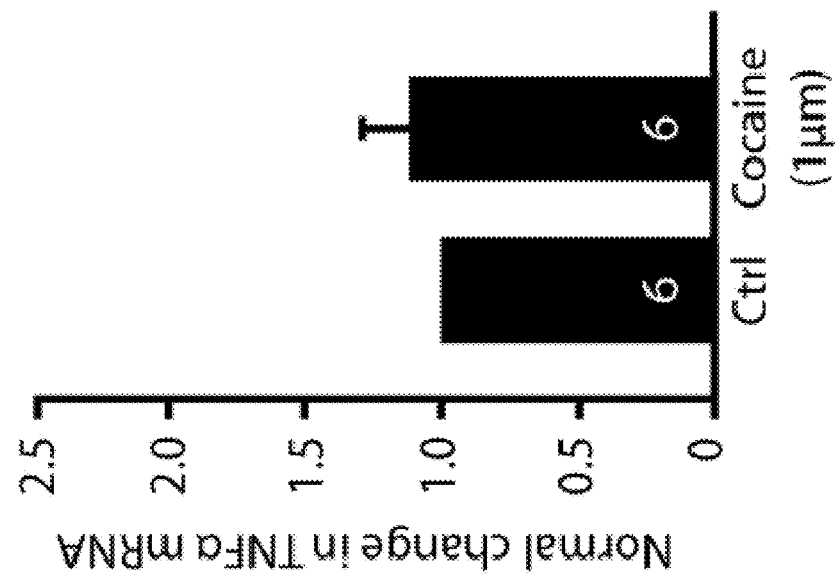
FIG. 7 is a series of charts, graphs and images showing that dopamine increases TNFα mRNA in microglia through D2 receptors.
Figure 7:
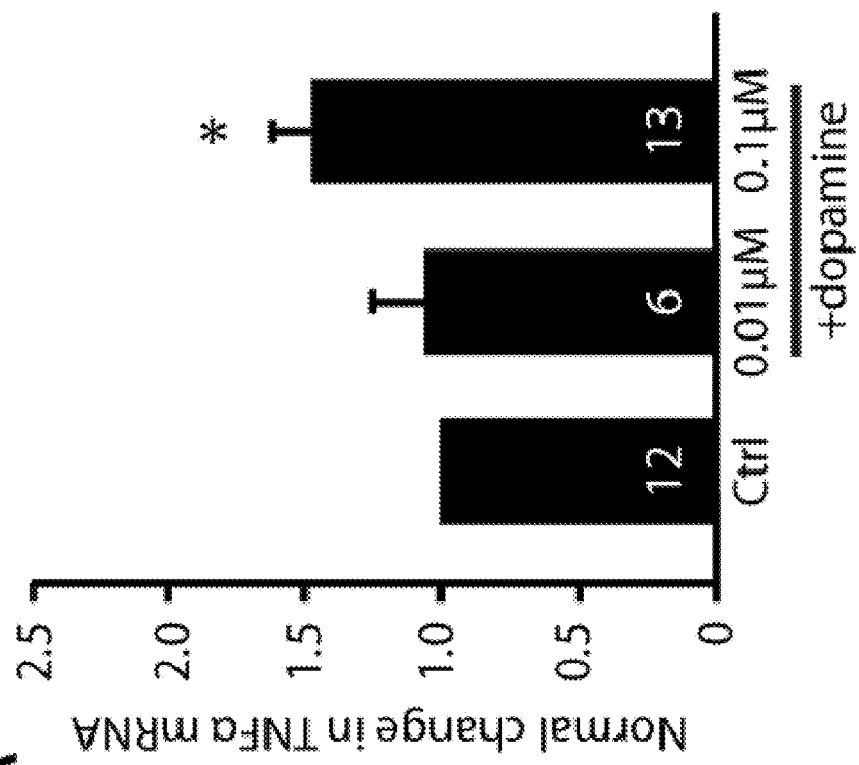
Figure 7:
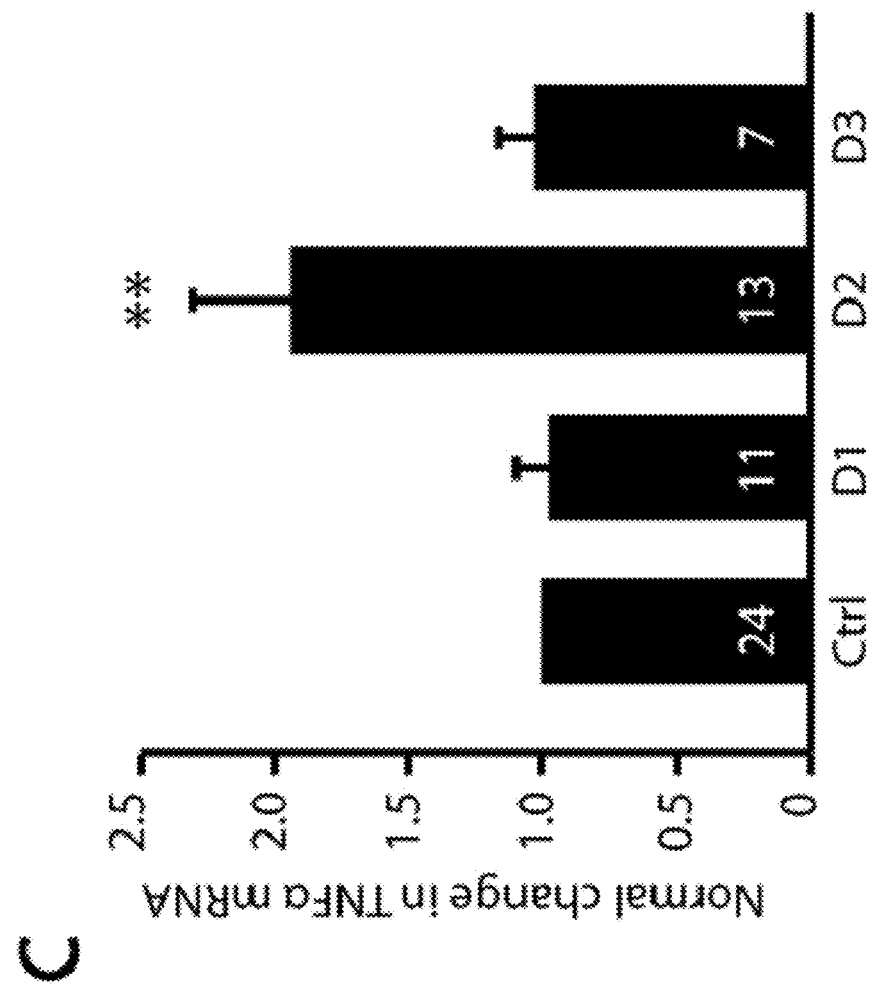
Figure 7:
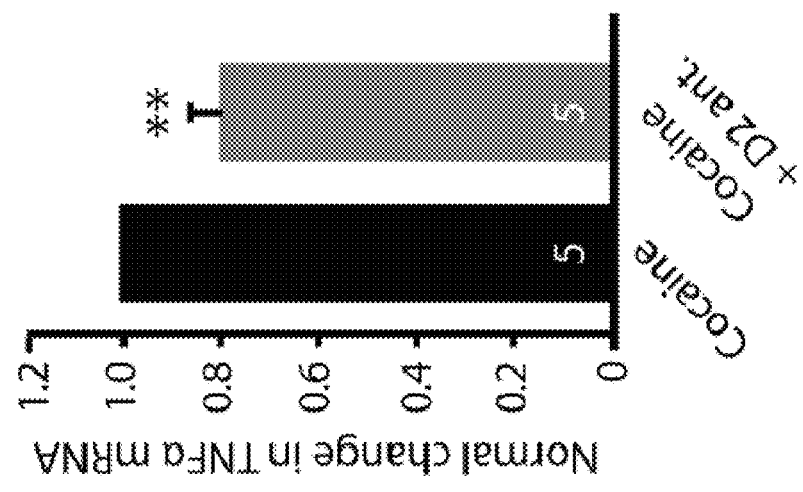
Figure 7:
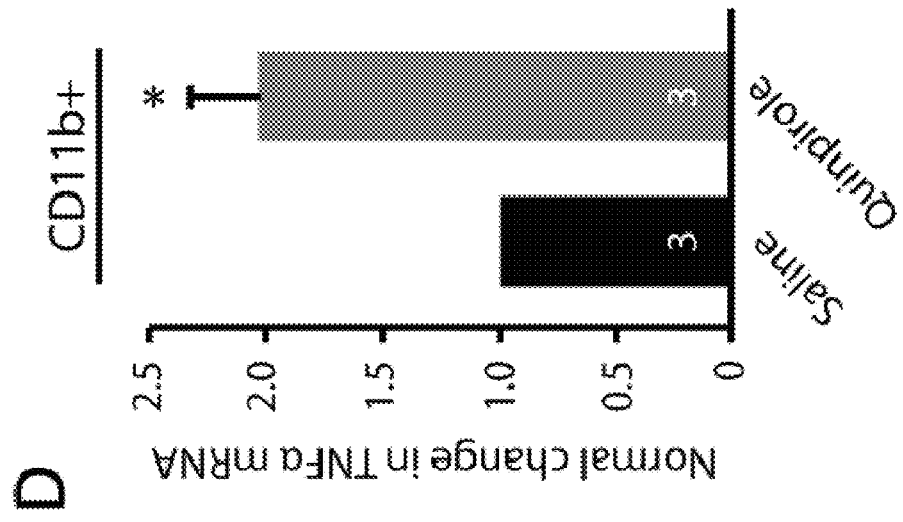

Cocaine could activate microglia either directly by binding the sigma receptor (Navarro et al., 2010) or the Toll-like receptor 4 (TLR4) (Northcutt et al., 2015), or indirectly through the elevation of dopamine. To test this, microglia cultures were treated with either dopamine or cocaine for 3 hours. Treatment of microglia with 1 µM dopamine, but not cocaine, significantly increased TNFα mRNA (FIG. 7A-B). This concentration of dopamine is reflective of the concentration found in the NAc in vivo following cocaine administration in rats (Hooks et al., 1992; Wise et al., 1995). However, the same treatment applied to cultured astrocytes had no effect on TNFα mRNA (FIG. 11A). Multiple dopamine receptors are expressed on microglia (Kettenmann et al., 2011); therefore it was tested whether dopamine acts through D1-like or D2-like receptors. Stimulating microglia with the D2-like agonist quinpirole was effective at increasing TNFα mRNA, while the D1 agonist SKF-38393 had no effect (FIG. 7C). The specific D3 agonist pramipexole also did not affect TNFα mRNA levels, suggesting that dopamine increases TNFα production in microglia through D2 receptors. Microglia transcriptional profiles change substantially during both development and the culturing process (Butovsky et al., 2014; Crain et al., 2013). Microglia were therefore cultured from adult animals, in a manner that preserves an in vivo transcriptional profile (Butovsky et al., 2014). A similar response to dopamine and lack of response to cocaine were seen (FIG. 11B-C). To directly test the response of microglia in vivo, mice were treated with quinpirole (0.5 mg/kg, IP; 24 and 1 hour prior to harvest) and microglia populations were isolated. Quinpirole treatment increased the TNFα mRNA in striatel microglia cells (FIG. 7D), but not in the other striatel cell types (138±72% of control; n=3 (4 mice pooled per experiment); Wilcoxon rank sum test, 1-way, p=0.49) nor in cortical microglia (82±37% of control; p=0.49), indicating that D2-agonism specifically increases microglial TNFα in the striatum in vivo. Further, co-administrating cocaine with the D2 antagonist L741,626 for 5 days reduced the cocaine-induced increase in microglial TNFα production (FIG. 7E). Finally, to verify that D2-like receptor activation was required for the TNFα-dependent decrease in AMPA/NMDA ratio observed on D1-MSNs, animals were treated for 5 d with cocaine and the D2 antagonist. Blocking D2 receptors (and thus preventing the activation of microglia) resulted in a large cocaine-induced increase in AMPA/NMDA ratio on D1-MSNs, similar to what is seen in TNFα$^{-/-}$ animals (FIG. 7F). Overall, this suggests that cocaine elevates dopamine levels, which act on D1 receptors on direct pathway MSNs to increase synaptic strength, and simultaneously activates microglia through D2 receptors and temporarily increases TNFα production.

MPLA Decreases Behavioural Sensitization

It is suggested that the activation of microglia acts to limit the changes induced in NAc circuitry by cocaine, but this activation occurs only during a narrow window following cocaine exposure. Because depotentiation of MSNs reduced cocaine-induced behavioural sensitization (Pascoli et al., 2012), it was tested whether re-activation of microglia would depress NAc synapses and suppress sensitization. To do this, monophosphoryl lipid A (MPLA), a detoxified variant of LPS, was used (Casella and Mitchell, 2008). MPLA acts as a weak TLR4 agonist that is at least 100-fold less pyrogenic than LPS (Cluff, 2010) and is used in humans as an adjuvant for several vaccine formulations. Furthermore, systemic injection of MPLA can improve Alzheimer's-related pathology in a mouse model, through a mild activation of microglia that did not induce extensive neuroinflammation or sickness behavior (Michaud et al., 2013). It was verified that MPLA activates microglia in the striatum, by injecting 10 µg MPLA IP after 10 days withdrawal from cocaine. MPLA treatment significantly increased Iba1 intensity within 4 hours compared to saline treated controls (FIG. 8A). This is consistent with previous observations that MPLA acts as a microglia modulator (Michaud et al., 2013). This activation was associated with an increase in striatal TNFα, as MPLA significantly increased striatal TNFα mRNA levels 4 hours and 24 hours after injection (FIG. 8B). It was next tested if MPLA treatment would depress synaptic strength in the NAc core. After 10 days of withdrawal, animals were injected with MPLA and evaluated 24 hours later for AMPA/NMDA ratios on D1-MSNs. MPLA treatment significantly reduced AMPA/NMDA ratio in D1-MSNs compared to saline treated controls (FIG. 8C). Because artificially reducing synaptic strength in the NAc can reduce behavioural sensitization (Pascoli et al., 2012), these data suggest that MPLA would suppress drug-induced behaviours.

To test this idea, it was first established that MPLA did not alter basal locomotion. No significant differences in locomotion were seen in mice tested 24 hours after an IP injection of 10 µg MPLA compared with saline injected mice (saline: 5752±325 cm; MPLA: 5415±378 cm; n=4 animals per group; Student's t-test, $t_{(6)}$=0.067, p>0.52). To evaluate whether MPLA can reduce the behavioral sensitization following prolonged abstinence from cocaine, wild-type mice were subjected to the standard sensitization protocol. After a period of abstinence, mice were injected with either 10 µg or 50 µg MPLA or saline, and 24 hours later tested for cocaine sensitization. Mice treated with MPLA had significantly reduced locomotor response in a dose dependent manner (FIG. 8D). This did not appear to be due to an increase in sensitivity to cocaine, as no increase in stereotypic behaviours was observed in MPLA treated mice (FIG. 12A-D). The effects of MPLA were dependent on TNFα, as MPLA had no effect on sensitization in TNFα$^{-/-}$ mice (FIG. 8E), which suggests that MPLA is acting through an elevation of TNFα and not other cytokines. Further, MPLA only acts to decrease the sensitized state, as it did not decrease the locomotor response to an initial dose of cocaine (FIG. 8F). However, this effect is temporary, as MPLA had little impact on sensitization when tested 4 d after injection (FIG. 12E). These observations suggest that even after a prolonged period of abstinence from cocaine, increasing TNFα can be effective in reducing the behavioural response to cocaine although it does not revert the system to the pre-sensitized state.

Discussion

Chronic cocaine administration produces long term neuroadaptions of glutamatergic signaling in the NAc that are thought to contribute to addiction-related changes in drug sensitivity and craving. Here it is shown that microglia in the NAc are transiently activated following 5 days of non-contingent cocaine administration, and act to down-regulate AMPARs on MSNs through increased TNFα signaling. Importantly, this limits the development of behavioural sensitization. Furthermore, it has been shown that following a period of abstinence, MPLA can re-activate microglia and decrease both synaptic strength in the NAc and the locomotor response to cocaine. The results suggest that microglia have an adaptive role in the response to cocaine and their modulation could be used as effective treatment against cocaine-induced behavioural changes. While much of the work has focused on changes in the NAc shell (Luscher and Malenka, 2011), alterations in the core may be particularly important for the expression of locomotor sensitization (Kalivas, 2009). Infusion of AMPA into the NAc core enhances locomotion in animals exposed to cocaine 2-3 weeks earlier (Bell and Kalives, 1996), while AMPAR antagonists administered into the NAc core prevent the expression of behavioral sensitization (Bell et al., 2000; Pierce et al., 1996). As the increase in NAc synaptic strength has been hypothesized to correlate with the development of craving (Conrad et al., 2008), and reducing synaptic strength in the NAc reduces cue-induced self-administration (Wisor et al., 2011), it also suggests that increasing TNFα with mild TLR4 activation may help blunt craving or incentive sensitization.

Further, the results explain a perplexing feature of chronic cocaine administration—that synaptic strength on D1-MSNs decreases initially and then slowly increases during withdrawal despite the acute effect of dopamine to increase AMPAR surface expression. While the formation and subsequent unsilencing of silent synapses likely contributes (Huang et al., 2009) to the changes in AMPA/NMDA ratios, the results suggest an additional mechanism. The results support the idea that dopamine does, as predicted by in vitro results, increase AMPA/NMDA ratios while simultaneously activating microglia to release TNFα. This TNFα release causes the decreased AMPA/NMDA ratios observed following repeated non-contingent administration of cocaine. This suppression is temporary as microglia slowly de-activate during withdrawal, revealing the underlying dopamine-induced potentiation. A challenge dose would re-activate the microglia, increase TNFα release, and again suppress AMPA/NMDA ratios, as observed (Boudreau et al., 2007; Thomas et al., 2001). In this model, dopamine acts through PKA to phosphorylate both GluA1 and T34-DARPP32 (Chao et al., 2002; Snyder et al., 2000) to increase AMPAR exocytosis (as does acute cocaine; (Bateup et al., 2008)), but chronic cocaine decreases DARPP32 phosphorylation (Di Benedetto et al., 2007) through TNFα (Lewitus et al., 2014) to endocytose AMPARs on D1-MSNs. Taken together, the data suggest that TNFα has an adaptive role in regulating glutamatergic transmission in the striatum when circuit homeostasis is perturbed.

Moreover, the data also suggest that microglia are adaptive regulators of striatal function. This is not to suggest that astrocytes do not also regulate striatel function; merely that astrocytes do not supply the TNFα that opposes the circuit and behavioural changes induced by cocaine. If astrocytic TNFα has any role, it appears to augment sensitization, as GFAP-Cre animals had slightly less sensitization than control mice. More work will have to be done to address the potential role of astrocytes. However, the results clearly indicate that microglia are the major source of TNFα for the synaptic regulation of the effects of cocaine. Isolation of microglial cells from the striatum after cocaine or quinpirole administration shows microglia are the major cell type to produce TNFα. Targeting these cells with CX3CR1-Cre also indicates a microglial source for the TNFα. It should be noted that CX3CR1 is also expressed in other cell types (including macrophages, other peripheral cells, and a small number of neurons), and a TLR4 agonist like MPLA will act on astrocytes and other cell types. However, the GFAP-Cre is also expressed in a substantial percentage of neurons and TNFα from these cells does not suppress behavioural sensitization, thus making a neuronal contributiquinone unlikely. So while the contribution of other cell types to the TNFα response cannot be excluded, it is difficult to argue that microglia are not the major source of the response. Microglia express a variety of neurotransmitters, neuropeptides, and immune receptors and have the capacity to rapidly respond to physiological changes in the brain (Kettenmann et al., 2011). The results support the idea that microglia have a protective role in maintaining brain homeostasis against perturbations. This cocaine-induced microglia activation is consistent with previous groups that demonstrate microglia activation by other drugs of abuse (Sekine et al., 2008; Zhang et al., 2011). There is likely a continuum of activation, with moderate activation beneficial in different learning and disease paradigms (Cami and Farre, 2003; Kreisel et al., 2014; Parkhurst et al., 2013) and part of a homeostatic-type response to significant deviations from the basal state (Kierdorf and Prinz, 2013). Augmenting the microglial response, through TLR4 or other means, may be used to treat addiction, provided it only moderately activates the microglia. MPLA, a weak TLR4 agonist, has been shown to mildly activate microglia and significantly improve cognitive function in a mouse model of neurodegeneration (Michaud et al., 2013). Here it was found that MPLA can acutely reduce behavioral sensitization even after prolonged abstinence from cocaine. If MPLA is found to similarly diminish reinstatement, it would suggest that MPLA could reduce the motivation to acquire drugs by blunting craving in established addicts and be used to prevent relapse, the most significant problem in the treatment of addiction.

Animals

TNFα−/− (RRID: IMSR_JAX:005540) and strain-matched wildtype mice (C571316/J) were acquired from Jackson Laboratories, and bred with B6.Cg-Tg(Drd1a-tdTomato) 6Calak/J (RRID: IMSR_JAX:016204) to obtain D1-MSN wildtype and D1-MSN TNFα−/− mice. Floxed TNFα mice were obtained from S. Nedospasov (Kuprash et al., 2005) and crossed with GFAP-Cre mice (Bajenaru et al., 2002) from NCI Mouse Repository (RRID: IMSR_NCIMR: 01XN3) or with Tg(Cx3cr1-cre)MW126Gsat mice (Yona et al., 2013) generated by N. Heintz (The Rockefeller University, GENSAT) and purchased from MMRRC (UC Davis; RRID: MMRRC_036395-UCD). GFAP or Cx3Cr1-Cre expressing mice were compared with GFAP or CX3CR1-Cre non-expressing littermates. Floxed TNFα and GFAP-Cre mice were on a C57/Bl6 background; Cx3Cr1-Cre mice were a mix of FVB/B6/129/Swiss/CD1. Behavioural sensitization in littermates only expressing Cre or heterozygous for the floxed allele of TNFα was indistinguishable from non-Cre expressing homozygous floxed animals. Experiments only used male mice at 8-12 weeks of age (electrophysiology) or 8-16 weeks of age (behaviour). Animals were housed 2-5 per cage and maintained on a 12 hour light/dark cycle. All animal procedures were performed in accordance with the guidelines of the Canadian Council for Animal Care and the Montreal General Hospital Facility Animal Care Committee.

Locomotor Activity

Locomotion was monitored in 30×30 cm plexiglass boxes by the EthoVision video-tracking system (Noldus) and performed near the end of the light phase of the light-dark cycle under dim red light. After habituating animals to handling, mice received IP injections of saline or cocaine and their activity was recorded for 15 min. Mice were tested during habituation to injection and the activity boxes (saline; days 1-2) and 5 repeated cocaine injections (15 mg/kg; days 3-7). Following 10 days without injections (withdrawal), mice receive a challenge dose of cocaine (15 mg/kg) and locomotor activity again assessed (day 17). Total distance traveled and stereotypy were evaluated from video by EthoVision. For stereotypy, the frequency of which the mouse stops moving (#pauses/min) was measured using a threshold start velocity of 2.00/second and a threshold stop velocity of 0 cm/s. The number of turns per minute (# turns/min) was measured by calculating the frequency for which the path of the mouse turns over a minimum distance of 3.00 cm. Velocity was assessed as the mean distance traveled (cm) over time (s).

Reagents

Reagents were acquired from Sigma, unless otherwise noted. Cocaine was acquired from Medisca Pharmaceutique, under license from Health Canada. DN-TNF (XENP1595) was a gift from Xencor, and is an engineered dominant negative variant of TNFα that rapidly binds with soluble TNFα to form inactive heterotrimers (Steed et al., 2003) and crosses the blood-brain barrier to affect the CNS (Lewitus et al., 2014).

Electrophysiology Recording

240 μm thick coronal slices containing the nucleus accumbens were prepared from brains of 8-9 week-old mice (with fluorescent D1-MSNs). After a 1 h recovery period, slices were placed in a submersion-type recording chamber and perfused (1.5-2 ml/min) at 30° C. with a bicarbonate-buffered artificial CSF saturated with 95% O2/5% CO2 and containing (in mM): 119 NaCl, 2.5 KCl, 1 NaH2PO4, 1.3 MgCl2, 2.5 CaCl2, 26.2 NaHCO3, 11 glucose, and 0.05 picrotoxin. Whole-cell voltage-clamp recordings from medium spiny neurons in the nucleus accumbens core were obtained under visual control using infrared-differential interference contrast microscopy. Whole-cell electrodes (2-4 MΩ) were filled with internal solution containing the following (in mM): 120 CsMeSO3, 15 CsCl, 8 NaCl, 0.2 EGTA, 10 HEPES, 2 Mg-ATP, 0.3 Na-GTP, 10 tetraethyl-ammonium, and 5 QX-314 [5-N-(2,6-dimethylphenylcarbamoylmethyl)triethylammonium bromide] (308-310 mOsm). pH was adjusted to 7.3 with CsOH. Cells with series resistance above 25 MΩ or a 20% change over time were excluded. Synaptic currents were evoked using stainless-steel bipolar stimulating electrodes placed 100-150 μm rostral to the recorded neurons. EPSCs were acquired with an Axopatch 200B (Molecular Devices), filtered at 2 kHz, and digitized at 10 kHz. Acquisition and analysis was performed using pCLAMP 10.2 (Molecular Devices). To calculate AMPA/NMDA ratios, evoked synaptic responses were collected at −70 mV to measure AMPAR-mediated EPSCs and at +40 mV to measure NMDAR-mediated EPSCs. Typically, 20 responses were averaged to generate an average response. The peak AMPA response was used to calculate the AMPAR component and the amplitude at 40 ms post the AMPAR peak response was used to calculate the slower NMDA component at +40 mV to calculate the AMPA/NMDA ratio.

Immunohistochemistry

Mice (8-10 weeks) were perfused and their brains submerged overnight in 4% PFA, cryoprotected with 30% sucrose, and cut in 30 μm thick coronal slices using a cryostat. The sections were incubated for 4 hours with blocking solution (2% normal goat serum, 3% BSA, 0.2% Triton X-100 in PBS) before incubation overnight at 4 C with primary antibodies in blocking solution (rabbit anti-Iba1 antibody [019-19741, Wako; 1:800; RRID: AB_2566825], chicken anti-GFAP antibody [AB5541, Millipore; 1:500; RRID: AB_177521], rabbit anti-NeuN [ab104225, Abcam, 1:400; RRID: AB_10711153], and rabbit anti-TNFα antibody [ab6671, Abcam, 1:100; RRID: AB_305641] or mouse anti-TNFα antibody [ab1793, Abcam, 1:100; RRID: AB_302615]). Sections were washed (2×15 min with PBST [0.05% Tween20] and 1×15 min with PBS at RT) and incubated for 2 hrs at room temperature in secondary antibodies (anti-rabbit, anti-chicken, or anti-mouse IgG-conjugated Alexa Fluorochrome [Invitrogen; 1:400]). Sections were washed and briefly (<30 seconds) incubated with Hoechst 33342 [H1399, Molecular Probes; 1:10,000] in PBS. The stained sections were imaged using an Olympus FluoView FV1000 confocal microscope with Fluoview imaging software (FV10-ASW). Images of the ventral striatum (nucleus accumbens core and shell) were acquired with a 40× or 60× objective and stacks of 25-30 optical sections (1 μm per section) of depth were Z-projected into a single window and analysed using ImageJ software (NIH).

Image Analysis

The number of Iba1+ microglia were manually counted from 212×212 μm (60× objectives) or 317×317 μm (40× objectives) images. TNFα intensity was measured using the mean grey value of the entire image while Iba1 intensity measurements were obtained using a thresholded area to highlight only the microglia. Cell body area ($\mu m^2$) was measured based on Iba1 staining and using the freehand selection tool. Additional analysis of microglia morphology in saline and cocaine treated mice was done using IMARIS software (Bitplane). Microglia were identified using Iba1 staining from z-stacks generated by confocal microscopy. 3D reconstruction of microglia filaments were generated by the IMARIS tool filament tracer. Tracing was done on representative microglia using the automatic detection mode, no loops allowed, start and end points manually selected. The following parameters were analyzed for 40 microglia per group: total process length (sum of length of all processes), total process volume, process diameter and number of branch points and terminals. All analyses were done blind to treatment or condition.

RNA Isolation and Quantitative PCR

For tissue, total RNA from the ventral striatum was extracted and isolated by RNAqueous-4PCR total RNA isolation kit (Ambion, AM1914), according to manufacturer's instructions. For microglia and astrocyte cultures, total RNA was isolated by RNeasy kit (Qiagen, 74136). For all sample types, 0.5 μg of total RNA was used for cDNA synthesis with Quantitect Reverse Transcription Kit (Qiagen, 205313), and quantitative RT-PCR was performed with Fast SYBR-Green Master Mix (Applied Biosystems) detected by StepOne Plus RealTime PCR system (Applied Biosystems). The sequences of qPCR primers used for mRNA quantification in this study were obtained from Integrated DNA Technologies, and are as follows: mouse TNFα forward, CCAGTGTGGGAAGCTGTCTT (SEQ ID NO: 1) [200 nM]; mouse TNFα reverse, AAGCAAAAGAGGAGGCAACA (SEQ ID NO: 2) [200 nM]; mouse GAPDH forward, ATGTGTCCGTCGTGGATCTGA (SEQ ID NO: 3) [300 nM]; mouse GAPDH reverse, TTGAAGTCGCAGGAGACAACCT (SEQ ID NO: 4) [300 nM]; rat TNFα forward, CCAGTGTGGGAAGCTGTCTT (SEQ ID NO: 1) [600 nM]; rat TNFα reverse, TGGGAGTTGCTGTTGAAGTC (SEQ ID NO: 5) [600 nM]; rat cyclophilin forward, CCGCTGTCTCTTTTCGCC (SEQ ID NO: 6) [500 nM]; rat cyclophilin reverse, GCTGTCTTTGGAACTTTGTCTG (SEQ ID NO: 7) [500 nM]. After 40 cycles, the Ct values were determined. To normalize the samples, ΔCt between TNFα and GADPH or cyclophilin Ct values was calculated. The x-fold difference in expression between the different treatments was then determined by subtraction of the ΔCt values and termed ΔΔCt. Finally, the total change was calculated as 2-ΔΔct and the relative amount compared with control samples was deducted.

Cell Culture

Mixed microglia-astrocyte primary cultures were prepared from the striatum of postnatal rats (day 0), essentially as described (Beattie et al., 2002). Briefly, tissue was dissociated by titration, and cells were seeded in glia media (MEM containing 5% FBS, 1.5% high sucrose MEM and 0.1% glutamax) on culture flasks (Corning) coated with poly-D lysine (Sigma) and placed in a humidified incubator at 37 C with 5% CO2. Neurons were removed by mechanical disruption and the medium was changed at day 1, and every 5-7 days after. Microglia were collected from mixed cultures at DIV 10-13 by moderate shaking (200 rpm) for 4 hrs at 37 C. Freshly collected microglia were plated at a density of approximately $5 \times 10^4$ cells/cm$^2$ in 6 cm dishes (Corning). Drug treatments of microglia were done at DIV 2-3. Pure astrocyte cultures were generated by treating mixed glia cultures with cytosine arabinoside (8 µm) for 5 days, followed by a 45 min treatment with 75 mM of the microglia toxin L-leucine methyl-ester (LME) (Pascual et al., 2012). Microglia and astrocyte cultures were treated for 3 hours with dopamine hydrochloride (Sigma) at 0.01 µM and 0.1 µM together with 0.05 mg/ml ascorbic acid (Fisher Scientific). Microglia cultures were also treated with cocaine (Medisca, 1 µM), D1 agonist SKF-38393 (Sigma, 1 µM), D2/3 agonist quinpirole (Sigma, 1 µM), and D3 agonist pramipexole dihydrochloride (Tocris, 1 µM).

Isolation of Adult Microglia

Adult male C57BL/6 mice (8-12 weeks) underwent cardiac perfusion with Hank's Balanced Salt Solution (HBSS) and whole brains were removed. Cortices and striata were dissected, cut in to small pieces and subjected to enzymatic digestion with the Neural Tissue Dissociation Kit (P) (Miltenyi Biotech, US cat no. 130-092-628), as per manufactures instructions. Tissue was homogenised and resuspended in 35% isotonic Percoll, overlayed with HBSS and spun at 400 g for 45 mins for the removal of myelin. Pure populations of microglial cells were obtained through magnetic bead cell sorting using CD11b microbeads (Miltenyi, cat no. 130-093-634). Aliquots from positive and negative bead selected fractions were removed for cell staining to assess cell purity. For staining, cells were stained with eflouro eFluor0780 viability dye (1:1000; eBioscience), blocked with FC-receptor blocked (1:200; BD Bioscience) and stained with CD11b-V450 (1:100; BD Bioscience). Cells were acquired using a BD FACS Canto II and analyzed using BD FACSDiva software. For RNA extraction, cell fractions were pelleted and lysed with 350 µL of RLT buffer (Qiagen) with 1% β-ME and frozen at −80. For cell culture, pure (>95% CD11b-positive) adult microglia were plated on poly-L-lysine coated plates at a density of 2×105 mL-1 in DMEM F12 with 10% L929-cell conditioned media (rich in M-CSF), 10% FBS, 1% P/S, and 40 ng/ml recombinant human TGF-β1 (Miltenyi, cat no: 130-095-067), to maintain their transcriptional profile, as previously described (Butovsky et al., 2014). Culture media were changed 3 days after plating and cells were used at 7 days.

Statistical Analysis

Statistical analyses were performed using JMP 8 or 11 (SAS Institute). All data are presented as mean±SEM. Data were tested for normality using the Shapiro-Wilk Test, and then compared using the twotailed Student's t-test (unless noted); multiple comparisons were analyzed by one-way ANOVA for independent and/or repeated measures and two-way ANOVA followed by post-hoc Dunnet's or Fisher's least significant difference. For experiments where a low number of samples were compared (n<6), the non-parametric Wilcoxon or Steel multiple comparison with control rank sum test was utilized. In all cases, the significance level was established at $p<0.05$.

Example 6

Decreased Locomotor Response with LPS

Mice were treated for 3 days with saline (1,2), then 5 consecutive days with 15 mg/kg cocaine (3-7). Animals then underwent a 9 day withdrawal period from cocaine. On day 9, they received an injection of saline or 50 µg/kg of LPS. 24 hours later, the mice were retested for the locomotor response in terms of distance (cm) traveled in 15 minutes. Mice treated with LPS had a lower response to cocaine than saline treated controls (p=0.052, one-tailed test). LPS was shown to act in a similar way as MPLA.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

Citations for References Referred to in the Specification

1. Kreitzer, A. C. & Malenka, R. C. Striatal plasticity and basal ganglia circuit function. *Neuron* 60, 543-54 (2008).
2. Luscher, C. & Malenka, R. C. Drug-Evoked Synaptic Plasticity in Addiction: From Molecular Changes to Circuit Remodeling. *Neuron* 69, 650-663 (2011).
3. Murer, M. G., Tseng, K. Y., Kasanetz, F., Belluscio, M. & Riquelme, L. A. Brain oscillations, medium spiny neurons, and dopamine. *Cell Mol Neurobiol* 22, 611-32 (2002).
4. Breakefield, X. O. et al. The pathophysiological basis of dystonias. *Nat Rev Neurosci* 9, 222-34 (2008).
5. Centonze, D. et al. Chronic haloperidol promotes corticostriatal long-term potentiation by targeting dopamine D2L receptors. *J Neurosci* 24, 8214-22 (2004).
6. Pascoli, V., Turiault, M. & Luscher, C. Reversal of cocaine-evoked synaptic potentiation resets drug-induced adaptive behaviour. *Nature* 481, 71-5 (2012).
7. Ogoshi, F. et al. Tumor necrosis-factor-alpha (TNF-alpha) induces rapid insertion of Ca2+-permeable alpha-amino-3-hydroxyl-5-methyl-4-isoxazole-propionate (AMPA)/kainate (Ca-A/K) channels in a subset of hippocampal pyramidal neurons. *Exp Neurol* 193, 384-93 (2005).
8. Zachariou, V. et al. Phosphorylation of DARPP-32 at Threonine-34 is required for cocaine action. *Neuropsychopharmacology* 31, 555-62 (2006).
9. Nakajima, A. et al. Role of tumor necrosis factor-alpha in methamphetamine-induced drug dependence and neurotoxicity. *Journal of Neuroscience* 24, 2212-25 (2004).

10. Goncalves, J. et al. Methamphetamine-induced early increase of IL-6 and TNF-alpha Mrna expression in the mouse brain. *Ann N Y Acad Sci* 1139, 103-11 (2008).
11. Wisor, J. P., Schmidt, M. A. & Clegern, W. C. Cerebral microglia mediate sleep/wake and neuroinflammatory effects of methamphetamine. *Brain Behav Immun* 25, 767-76 (2011).
12. Piechota, M. et al. The dissection of transcriptional modules regulated by various drugs of abuse in the mouse striatum. *Genome Biol* 11, R48 (2010).
13. Wang, X. et al. Morphine activates neuroinflammation in a manner parallel to endotoxin. *Proc Natl Aced Sci USA* 109, 6325-30 (2012).
14. Alfonso-Loeches, S., Pascual-Lucas, M., Blanco, A. M., Sanchez-Vera, I. & Guerri, C. Pivotal role of TLR4 receptors in alcohol-induced neuroinflammation and brain damage. *J Neurosci* 30, 8285-95 (2010).
15. Narita, M. et al. Direct evidence of astrocytic modulation in the development of rewarding effects induced by drugs of abuse. *Neuropsychopharmacology* 31, 2476-88 (2006).
16. Niwa, M. et al. Tumor necrosis factor-alpha and its inducer inhibit morphine-induced rewarding effects and sensitization. *Biological Psychiatry* 62, 658-68 (2007).
17. Niwa, M. et al. An inducer for glial cell line-derived neurotrophic factor and tumor necrosis factor-alpha protects against methamphetamine-induced rewarding effects and sensitization. *Biological Psychiatry* 61, 890-901 (2007).
18. Thomas, M. J., Beurrier, C., Bonci, A. & Malenka, R. C. Long-term depression in the nucleus accumbens: a neural correlate of behavioral sensitization to cocaine. *Nat Neurosci* 4, 1217-23. (2001).
19. Wolf, M. E. The role of excitatory amino acids in behavioral sensitization to psychomotor stimulants. *Prog Neurobiol* 54, 679-720 (1998).
20. Kalivas, P. W. & Stewart, J. Dopamine transmission in the initiation and expression of drug- and stress-induced sensitization of motor activity. *Brain Research—Brain Research Reviews* 16, 223-44 (1991).
21. Steed, P. M. et al. Inactivation of TNF signaling by rationally designed dominant-negative TNF variants. *Science* 301, 1895-8 (2003).
22. Matyas et al. Vaccine (2013) 31: 2804-10.
23. Lewitus, et al., 2014 18:6146-55
24. Abbott, L. F. & Nelson, S. B. Synaptic plasticity: taming the beast. *Nat Neurosci* 3 Suppl, 1178-83 (2000).
Bajenaru, M. L., Zhu, Y., Hedrick, N. M., Donahoe, J., Parada, L. F., and Gutmann, D. H. (2002). Astrocyte-specific inactivation of the neurofibromatosis 1 gene (NF1) is insufficient for astrocytoma formation. Molecular and cellular biology 22, 5100-5113.
Bateup, H. S., Svenningsson, P., Kuroiwa, M., Gong, S., Nishi, A., Heintz, N., and Greengard, P. (2008). Cell type-specific regulation of DARPP-32 phosphorylation by psychostimulant and antipsychotic drugs. Nat Neurosci 11, 932-939.
Beattie, E. C., Stellwagen, D., Morishita, W., Bresnahan, J. C., Ha, B. K., Von Zastrow, M., Beattie, M. S., and Malenka, R. C. (2002). Control of synaptic strength by glial TNFalpha. Science 295, 2282-2285.
Bell, K., Duffy, P., and Kalives, P. W. (2000). Context-specific enhancement of glutamate transmission by cocaine. Neuropsychopharmacology 23, 335-344.
Bell, K., and Kalives, P. W. (1996). Context-specific cross-sensitization between systemic cocaine and intra-accumbens AMPA infusion in the rat. Psychopharmacology (Berl) 127, 377-383.

Boudreau, A. C., Reimers, J. M., Milovanovic, M., and Wolf, M. E. (2007). Cell surface AMPA receptors in the rat nucleus accumbens increase during cocaine withdrawal but internalize after cocaine challenge in association with altered activation of mitogen-activated protein kinases. Journal of Neuroscience 27, 10621-10635.
Boudreau, A. C., and Wolf, M. E. (2005). Behavioral sensitization to cocaine is associated with increased AMPA receptor surface expression in the nucleus accumbens. Journal of Neuroscience 25, 9144-9151.
Bowers, M. S., and Kalives, P. W. (2003). Forebrain astroglial plasticity is induced following withdrawal from repeated cocaine administration. Eur J Neurosci 17, 1273-1278.
Butovsky, O., Jedrychowski, M. P., Moore, C S., Cialic, R., Lanser, A. J., Gabriely, G., Koeglsperger, T., Dake, B., Wu, P. M., Doykan, C. E., et al. (2014). Identification of a unique TGF-beta-dependent molecular and functional signature in microglia. Nat Neurosci 17, 131-143.
Cami, J., and Farre, M. (2003). Drug addiction. The New England journal of medicine 349, 975-986.
Casella, C. R., and Mitchell, T. C. (2008). Putting endotoxin to work for us: monophosphoryl lipid A as a safe and effective vaccine adjuvant. Cellular and molecular life sciences: CMLS 65, 3231-3240.
Cepeda, C., Andre, V. M., Yamazaki, I., Wu, N., Kleiman-Weiner, M., and Levine, M. S. (2008). Differential electrophysiological properties of dopamine D1 and D2 receptor-containing striatel medium-sized spiny neurons. Eur J Neurosci 27, 671-682.
Chao, S. Z., Lu, W., Lee, H. K., Huganir, R. L., and Wolf, M. E. (2002). D(1) dopamine receptor stimulation increases GluR1 phosphorylation in postnatal nucleus accumbens cultures. Journal of Neurochemistry 81, 984-992.
Clem, R. L., and Huganir, R. L. (2010). Calcium-permeable AMPA receptor dynamics mediate fear memory erasure. Science 330, 1108-1112.
Cluff, C. W. (2010). Monophosphoryl lipid A (MPL) as an adjuvant for anti-cancer vaccines: clinical results. Advances in experimental medicine and biology 667, 111-123.
Conrad, K. L., Tseng, K. Y., Uejima, J. L., Reimers, J. M., Heng, L. J., Shaham, Y., Marinelli, M., and Wolf, M. E. (2008). Formation of accumbens GluR2-lacking AMPA receptors mediates incubation of cocaine craving. Nature 454, 118-121.
Crain, J. M., Nikodemova, M., and Watters, J. J. (2013). Microglia express distinct M1 and M2 phenotypic markers in the postnatal and adult central nervous system in male and female mice. J Neurosci Res 91, 1143-1151.
Di Benedetto, M., D'Addario, C., Candeletti, S., and Romualdi, P. (2007). Alterations of CREB and DARPP-32 phosphorylation following cocaine and monoaminergic uptake inhibitors. Brain Res 1128, 33-39.
Dobi, A., Seabold, G. K., Christensen, C. H., Bock, R., and Alvarez, V. A. (2011). Cocaine-Induced Plasticity in the Nucleus Accumbens Is Cell Specific and Develops without Prolonged Withdrawal. Journal of Neuroscience 31, 1895-1904.
Ghasemzadeh, M. B., Vasudevan, P., Mueller, C. R., Seubert, C., and Mantsch, J. R. (2009). Region-specific alterations in glutamate receptor expression and subcellular distribution following extinction of cocaine self-administration. Brain Res 1267, 89-102.
Grabert, K., Michoel, T., Karavolos, M. H., Clohisey, S., Baillie, J. K., Stevens, M. P., Freeman, T. C., Summers, K.

M., and McColl, B. W. (2016). Microglial brain region-dependent diversity and selective regional sensitivities to aging. Nat Neurosci 19, 504-516.

Hooks, M. S., Colvin, A. C., Juncos, J. L., and Justice, J. B., Jr. (1992). Individual differences in basal and cocaine-stimulated extracellular dopamine in the nucleus accumbens using quantitative microdialysis. Brain Res 587, 306-312.

Huang, Y. H., Lin, Y., Mu, P., Lee, B R., Brown, T. E., Wayman, G., Marie, H., Liu, W., Yan, Z., Sorg, B. A., et al. (2009). In vivo cocaine experience generates silent synapses. Neuron 63, 40-47.

Hughes, P. M., Botham, M. S., Frentzel, S., Mir, A., and Perry, V. H. (2002). Expression of fractalkine (CX3CL1) and its receptor, CX3CR1, during acute and chronic inflammation in the rodent CNS. Glia 37, 314-327.

Hutchinson, M R., and Watkins, L. R. (2014). Why is neuroimmunopharmacology crucial for the future of addiction research? Neuropharmacology 76 Pt B, 218-227.

Kalives, P. W. (2009). The glutamate homeostasis hypothesis of addiction. Nat Rev Neurosci 10, 561-572.

Kettenmann, H., Hanisch, U. K., Noda, M., and Verkhratsky, A. (2011). Physiology of microglia. Physiol Rev 91, 461-553.

Kierdorf, K., and Prinz, M. (2013). Factors regulating microglia activation. Frontiers in cellular neuroscience 7, 44.

Kim, J., Park, B. H., Lee, J. H., Park, S. K., and Kim, J. H. (2011). Cell type-specific alterations in the nucleus accumbens by repeated exposures to cocaine. Biol Psychiatry 69, 1026-1034.

Kourrich, S., Rothwell, P. E., Klug, J R., and Thomas, M. J. (2007). Cocaine experience controls bidirectional synaptic plasticity in the nucleus accumbens. Journal of Neuroscience 27, 7921-7928.

Kreisel, T., Frank, M. G., Licht, T., Reshef, R., Ben-Menachem-Zidon, O., Baratta, M V., Maier, S. F., and Yirmiya, R. (2014). Dynamic microglial alterations underlie stress-induced depressive-like behavior and suppressed neurogenesis. Mol Psychiatry 19, 699-709.

Kuprash, D V., Tumanov, A. V., Liepinsh, D. J., Koroleva, E. P., Drutskaya, M. S., Kruglov, A. A., Shakhov, A. N., Southon, E., Murphy, W. J., Tessarollo, L., et al. (2005). Novel tumor necrosis factor-knockout mice that lack Peyer's patches. European journal of immunology 35, 1592-1600.

Lewitus, G. M., Pribiag, H., Duseja, R., St-Hilaire, M., and Stellwagen, D. (2014). An Adaptive Role of TNFalpha in the Regulation of Striatal Synapses. J Neurosci 34, 6146-6155.

Lu, L., Grimm, J. W., Shaham, Y., and Hope, B. T. (2003). Molecular neuroadaptations in the accumbens and ventral tegmental area during the first 90 days of forced abstinence from cocaine self-administration in rats. J Neurochem 85, 1604-1613.

Luscher, C., and Malenka, R. C. (2011). Drug-Evoked Synaptic Plasticity in Addiction: From Molecular Changes to Circuit Remodeling. Neuron 69, 650-663.

Mameli, M., Halbout, B., Creton, C., Engblom, D., Parkitna, J R., Spanagel, R., and Luscher, C. (2009). Cocaine-evoked synaptic plasticity: persistence in the VTA triggers adaptations in the NAc. Nature Neuroscience 12, 1036-U1108.

Mangiavacchi, S., and Wolf, M. E. (2004). D1 dopamine receptor stimulation increases the rate of AMPA receptor insertion onto the surface of cultured nucleus accumbens neurons through a pathway dependent on protein kinase A. Journal of Neurochemistry 88, 1261-1271

Meucci, O., Fatatis, A., Simen, A. A., and Miller, R. J. (2000). Expression of CX3CR1 chemokine receptors on neurons and their role in neuronal survival. Proc Natl Acad Sci USA 97, 8075-8080.

Michaud, J. P., Halle, M., Lampron, A., Theriault, P., Prefontaine, P., Fileli, M., Tribout-Jover, P., Lanteigne, A. M., Jodoin, R., Cluff, C., et al. (2013). Toll-like receptor 4 stimulation with the detoxified ligand monophosphoryl lipid A improves Alzheimer's disease-related pathology. Proc Natl Acad Sci USA 110, 1941-1946.

Miguel-Hidalgo, J. J. (2009). The role of glial cells in drug abuse. Current drug abuse reviews 2, 72-82.

Nakajima, A., Yamada, K., Nagai, T., Uchiyama, T., Miyamoto, Y., Mamiya, T., He, J., Nitta, A., Mizuno, M., Tran, M. H., et al. (2004). Role of tumor necrosis factor-alpha in methamphetamine-induced drug dependence and neurotoxicity. Journal of Neuroscience 24, 2212-2225.

Navarro, G., Moreno, E., Aymerich, M., Marcellino, D., McCormick, P. J., Mellol, J., Cortes, A., Casado, V., Canela, E. I., Ortiz, J., et al. (2010). Direct involvement of sigma-1 receptors in the dopamine D(1) receptor-mediated effects of cocaine. Proceedings of the National Academy of Sciences of the United States of America 107, 18676-18681.

Northcutt, A L., Hutchinson, M R., Wang, X., Baratta, M V., Hiranita, T., Cochran, T A., Pomrenze, M B., Geier, E L., Kopajtic, T A., Li, C. M., et al. (2015). DAT isn't all that: cocaine reward and reinforcement require Toll-like receptor 4 signaling. Mol Psychiatry 20, 1525-1537.

Ortinski, P. I., Vassoler, F. M., Carlson, C C., and Pierce, R. C. (2012). Temporally dependent changes in cocaine-induced synaptic plasticity in the nucleus accumbens shell are reversed by D1-like dopamine receptor stimulation. Neuropsychopharmacology 37, 1671-1682.

Parkhurst, C. N., Yang, G., Ninan, I., Saves, J. N., Yates, J R., 3rd, Lafaille, J. J., Hempstead, B. L., Littman, D R., and Can, W. B. (2013). Microglia promote learning-dependent synapse formation through brain-derived neurotrophic factor. Cell 155, 1596-1609.

Pascoli, V., Turiault, M., and Luscher, C. (2012). Reversal of cocaine-evoked synaptic potentiation resets drug-induced adaptive behaviour. Nature 481, 71-75.

Pascual, O., Ben Achour, S., Rostaing, P., Triller, A., and Bessis, A. (2012). Microglia activation triggers astrocyte-mediated modulation of excitatory neurotransmission. Proc Natl Aced Sci USA 109, E197-205.

Pierce, R. C., Bell, K., Duffy, P., and Kalivas, P. W. (1996). Repeated cocaine augments excitatory amino acid transmission in the nucleus accumbens only in rats having developed behavioral sensitization. J Neurosci 16, 1550-1560.

Robinson, T. E., and Berridge, K. C. (2001). Incentive-sensitization and addiction. Addiction 96, 103-114.

Schramm-Sapyta, N. L., Olsen, C. M., and Winder, D. G. (2006). Cocaine self-administration reduces excitatory responses in the mouse nucleus accumbens shell. Neuropsychopharmacology 31, 1444-1451.

Schumann, J., and Yaka, R. (2009). Prolonged withdrawal from repeated noncontingent cocaine exposure increases NMDA receptor expression and ERK activity in the nucleus accumbens. J Neurosci 29, 6955-6963.

Sekine, Y., Ouchi, Y., Sugihara, G., Takei, N., Yoshikawa, E., Nakamura, K., Iwata, Y., Tsuchiya, K. J., Suda, S., Suzuki, K., et al. (2008). Methamphetamine causes microglial activation in the brains of human abusers. J Neurosci 28, 5756-5761.

Snyder, C L., Allen, P B., Fienberg, A. A., Valle, C C., Huganir, R. L., Nairn, A. C., and Greengard, P. (2000). Regulation of phosphorylation of the GluR1 AMPA receptor in the neostriatum by dopamine and psychostimulants in vivo. J Neurosci 20, 4480-4488.

Steed, P. M., Tansey, M. G., Zalevsky, J., Zhukovsky, E. A., Desjarlais, J. R., Szymkowski, D. E., Abbott, C., Carmichael, D., Chan, C., Cherry, L., et al. (2003). Inactivation of TNF signaling by rationally designed dominant-negative TNF variants. Science 301, 1895-1898.

Stellwagen, D., and Malenka, R. C. (2006). Synaptic scaling mediated by glial TNF-alpha. Nature 440, 1054-1059.

Thomas, D. M., Walker, P. D., Benjamins, J. A., Geddes, T. J., and Kuhn, D. M. (2004). Methamphetamine neurotoxicity in dopamine nerve endings of the striatum is associated with microglial activation. J Pharmacol Exp Ther 311, 1-7.

Thomas, M. J., Beurrier, C., Bonci, A., and Malenka, R. C. (2001). Long-term depression in the nucleus accumbens: a neural correlate of behavioral sensitization to cocaine. Nat Neurosci 4, 1217-1223.

Wise, R. A., Newton, P., Leeb, K., Burnette, B., Pocock, D., and Justice, J. B., Jr. (1995). Fluctuations in nucleus accumbens dopamine concentration during intravenous cocaine self-administration in rats. Psychopharmacology (Berl) 120, 10-20.

Wisor, J. P., Schmidt, M. A., and Clegern, W. C. (2011). Cerebral microglia mediate sleep/wake and neuroinflammatory effects of methamphetamine. Brain, behavior, and immunity 25, 767-776.

Yona, S., Kim, K. W., Wolf, Y., Mildner, A., Varol, D., Braker, M., Strauss-Ayali, D., Viukov, S., Guilliams, M., Misharin, A., et al. (2013). Fate mapping reveals origins and dynamics of monocytes and tissue macrophages under homeostasis. Immunity 38, 79-91.

The invention claimed is:

1. A method of reducing AMPA/NMDA ratio in D1-type medium spiny neurons (MSN) and reducing development of behavioural sensitization or suppressing drug induced behavioural sensitization in a subject, optionally a subject that is afflicted with an addiction, comprising administering to the subject in need thereof an effective amount of a Toll-like receptor 4 (TLR4) agonist as active substance or a composition comprising said TLR4 agonist as active substance.

2. The method of claim 1, wherein amount administered is sufficient to increase Tumor Necrosis Factor alpha (TNFα) mRNA and/or protein levels in the subject.

3. The method of claim 2, wherein amount administered is sufficient to increase Tumor Necrosis Factor alpha (TNFα) mRNA and/or protein levels in the subject by at least 1.5 fold.

4. The method of claim 1, wherein the TLR4 agonist is selected from the group consisting of a monophosphoryl lipid A; a glucopyranosyl lipid (GPL); 3 de-acylated MPL (3D-MPL); a lipopolysaccharide (LPS); amphotericin B; a lipopeptidophosphoglycan; fetuin A; Hsp60; aminoalkyl glucosaminide phosphate (AGP) and/or mixtures thereof.

5. The method of claim 4, wherein the TLR4 agonist is a monophosphoryl lipid A.

6. The method of claim 5, wherein the monophosphoryl lipid A is purified from a bacteria or is synthetic monophosphoryl lipid A.

7. The method of claim 6, wherein the bacteria is *E coli* or a *Salmonella* species.

8. The method of claim 4, wherein the TLR4 agonist is GPL.

9. The method of claim 4, wherein the TLR4 agonist is 3D-MPL.

10. The method of claim 4, wherein the LPS is a detoxified LPS.

11. The method of claim 1, wherein the subject has a substance use disorder; a striatal disorder; or a repetitive motor problem.

12. The method of claim 11, wherein the substance use disorder is a drug addiction, wherein the striatal disorder is dyskinesia or dystonia, and wherein the repetitive motor problem is obsessive compulsive disorder.

13. The method of claim 1, wherein the method is for reducing the likelihood of a subject developing or redeveloping a drug addiction and/or treating a subject afflicted with a drug addiction.

14. The method of claim 13, wherein the drug is selected from group consisting of cocaine, crack, opioids, lysergic acid diethylamide-25 (LSD), ketamine, tobacco, alcohol, caffeine, nicotine, *cannabis* and *cannabis* derivatives, phencyclidine, sedative hypnotics, pain-killers, psychostimulants, amphetamine, methamphetamine and ecstasy or mixtures thereof.

15. The method of claim 14, wherein the drug is selected from cocaine, opioids, amphetamine, methamphetamine, alcohol, and nicotine.

16. The method of claim 15, wherein the drug is selected from cocaine and crack.

17. The method of claim 15, wherein the opioid is selected from morphine and heroin.

18. The method of claim 17, wherein the opioid is morphine.

19. The method of claim 15, wherein the drug is nicotine.

20. The method of claim 15, wherein the drug is methamphetamine or amphetamine.

21. The method of claim 14, wherein the drug is alcohol.

* * * * *